United States Patent
Zhang et al.

(10) Patent No.: US 12,098,119 B2
(45) Date of Patent: Sep. 24, 2024

(54) COMPOUND USED AS SIRT6 SMALL-MOLECULE ALLOSTERIC ACTIVATOR AND PHARMACEUTICAL COMPOSITION THEREOF

(71) Applicant: Nutshell BioTech (Shanghai) Co., Ltd., Shanghai (CN)

(72) Inventors: Jian Zhang, Shanghai (CN); Yinyi Chen, Shanghai (CN); Cong Ruan, Shanghai (CN); Xiuyan Yang, Shanghai (CN); Chengxiang Wang, Shanghai (CN); Qiufen Zhang, Shanghai (CN); Jialin Shang, Shanghai (CN); Xinyuan Xu, Shanghai (CN)

(73) Assignee: Nutshell BioTech (Shanghai) Co., Ltd., Shanghai (CN)

( * ) Notice: Subject to any disclaimer, the term of this patent is extended or adjusted under 35 U.S.C. 154(b) by 930 days.

(21) Appl. No.: 17/293,917

(22) PCT Filed: May 14, 2018

(86) PCT No.: PCT/CN2018/086766
§ 371 (c)(1),
(2) Date: May 14, 2021

(87) PCT Pub. No.: WO2019/029211
PCT Pub. Date: Feb. 14, 2019

(65) Prior Publication Data
US 2022/0220069 A1    Jul. 14, 2022

(30) Foreign Application Priority Data

Aug. 10, 2017 (CN) .......................... 201710681498.6
Feb. 8, 2018 (CN) .......................... 201810126641.X

(51) Int. Cl.
C07C 303/38 (2006.01)
C07C 311/37 (2006.01)
C07C 311/44 (2006.01)

(52) U.S. Cl.
CPC .......... *C07C 303/38* (2013.01); *C07C 311/37* (2013.01); *C07C 311/44* (2013.01)

(58) Field of Classification Search
None
See application file for complete search history.

(56) References Cited

U.S. PATENT DOCUMENTS 7,262,318 B2    8/2007  Pfizer
2005/0228015 A1*  10/2005  Hamanaka ........... C07D 277/24
                                              548/305.7

FOREIGN PATENT DOCUMENTS

CN    1930121 A    3/2007
CN  104161749 A    11/2014

OTHER PUBLICATIONS

Shao ("Discovery of novel DNA methyltransferase 3A inhibitors via structure-based virtual screening and biological assays" Bioorganic and Medicinal Chemistry Letters, 2017, 27, p. 342-346, including Supporting Information (SI) p. S1-S15; first published online on Nov. 11, 2016). (Year: 2016).*

(Continued)

*Primary Examiner* — Amy C Bonaparte
(74) *Attorney, Agent, or Firm* — Houston Beshining Law Office PLLC; Liangang Ye

(57) ABSTRACT

Disclosed by the present invention are an SIRT6 small-molecule allosteric activator and the application thereof and provided is an SIRT6 small-molecule allosteric activator that contains a derivative as shown in formula (1) or a pharmacologically acceptable salt thereof as the active ingredient. The SIRT6 small-molecule allosteric activator designed and synthesized in the present invention has high efficacy and (Continued)

low toxicity, may significantly activate SIRT6 activity during in vitro experiments, and has great importance in the development of pharmaceuticals for relevant diseases.

3 Claims, 23 Drawing Sheets

(56) References Cited

OTHER PUBLICATIONS

National Center for Biotechnology Information (2024). PubChem Substance Record for SID 124602663, CCG-4745, Source: Center for Chemical Genomics, University of Michigan. Retrieved Mar. 29, 2024 from https://pubchem.ncbi.nlm.nih.gov/substance/124602663, publicly available as of Aug. 2, 2011 (Year: 2011).*
Scozzafava ("Carbonic Anhydrase Inhibitors: Perfluoroalkyl/Aryl-Substituted Derivatives of Aromatic/Heterocyclic Sulfonamides as Topical Intraocular Pressure-Lowering Agents with Prolonged Duration of Action" J. Med. Chem. 2000, 43, p. 4542-4551) (Year: 2000).*
Shao, Zhiyuan etc. "Discovery of novel DNA methyltransferase 3A inhibitors via structure-based virtual screening and biological assaya." Bioorganic & Medicinal Chemistry Letters. vol. 27,No. 2, Nov. 11, 2016(Nov. 11, 2016), pp. 342-346, Supporting Information, only abstract provided.
American Chemical Society ACS. "TNext Registry data base" http://next.stn.org, Oct. 20, 2005 (Oct. 20, 2005), see form PCT/ISA/237, Box V for detailed referential portion.
Aug. 21, 2018 International Search Report issued in International Patent Application No. PCT/CN2018/086766.
Aug. 21, 2018 Written Opinion of the International Searching Authority issued in International Patent Application No. PCT/CN2018/086766.
Woolley, D.W.et al, "Synthesis of derivatives of 1,2-dichloro-4-benzenesulfonamido-5-nitrobenzene and their use in the chemotherapy of spontaneous cancers," Canadian Journal of Chemistry, vol. 43(5), pp. 1454-1459, Dec. 31, 1965.
STN Registry Database CAS Number, pp. 1-30, Oct. 10, 2007.
Aug. 28, 2020 First Office Action issued in Chinese Patent Application No. 201710681498.6.
Feb. 2, 2021 Second Office Action issued in Chinese Patent Application No. 201710681498.6.
Aug. 5, 2021 Refusal Decision issued in Chinese Patent Application No. 201710681498.6.
Sep. 3, 2021 First Office Action issued in Chinese Patent Application No. 201810126641.X.

* cited by examiner

COMPOUND USED AS SIRT6 SMALL-MOLECULE ALLOSTERIC ACTIVATOR AND PHARMACEUTICAL COMPOSITION THEREOF

CROSS REFERENCE

The application claims the priorities of Chinese Patent Application No. 201810126641.X, entitled "COMPOUND USED AS SIRT6 SMALL-MOLECULE ALLOSTERIC ACTIVATOR AND PHARMACEUTICAL COMPOSITION THEREOF", filed on Feb. 5, 2018 and Chinese Patent Application No. 201710681498.6, entitled "COMPOUND USED AS SIRT6 SMALL-MOLECULE ALLOSTERIC ACTIVATOR AND PHARMACEUTICAL COMPOSITION THEREOF", filed on Aug. 10, 2017, the disclosure of which is incorporated herein by reference in its entirely.

FIELD OF INVENTION

The present invention relates to the field of pharmaceutical chemotherapy, specifically, relates to SIRT6 small-molecular adjuvant activator and its application as a pharmaceutical compound for preventing or treating related diseases.

BACKGROUND OF INVENTION

The mammalian Sirtuin family contains seven members (SIRT1-SIRT7), generally having enzyme activity for monophosphate-ADP-ribosylation (Mono-ADP-ribosylation) or enzyme activity for deacetylation, which mainly includes deacetylating enzyme activity (Deacetylation) and demyristosis enzyme activity (Demyristoylation), and the like. These members are widely involved in various life activity processes such as energy metabolism, cell pressure stress, genome stability, aging, tumor, etc.

SIRT6 is one of the main members of the Sirtuin family, which has a large Rossmann folding structure domain and a small zinc ion structure domain on the spatial structure, wherein both the auxiliary factor NAD⁺ and the substrate polypeptide of the enzyme are combined in the Rossmann domain, and the zinc ion domain has a conservative zinc ion binding sequence. The SIRT6 can catalyze the deacetylation of substrate proteins or the Mono-ADP-ribosylation by the aid of the auxiliary factor $NAD^+$. The K9 and K56 sites of the histone H3 (hereinafter H3K9, H3K56) and CtIP (C-terminal binding protein interaction protein) are reported deacetylation substrates, while PARP1 [Poly (ADP-RI-BOSE) Polymerase 1] is a currently known monophosphate ribosyl substrate.

In organisms, SIRT6 is mainly deacetylated through H3K9 and H3K56 to regulate some important transcription factors (such as NF-kappa B, HIF 1α, C-Myc, etc.) to participate in various life processes such as genome stability maintenance, DNA repair, inflammation and glucose and lipid metabolism, and is closely related to diseases such as tumor generation, heart disease, aging, diabetes, and aging, which indicates that SIRT6 has a particularly important biological function.

An analysis of SIRT6 expression of 1000 various tumor cell lines in a human Cancer cell line Encyclopedia (CCLE) has been found to find that the SIRT6 is differentially expressed in the tumor, and the tumor cell lines at the near 35% appear different degrees of SIRT6 deletion, wherein the expression quantity of the SIRT6 in the digestive tract tumor cells is almost all reduced. Therefore, up-regulation of SIRT6 activity is believed to be a new strategy for treating a variety of diseases.

Therefore, it has been found that SIRT6 small-molecule activator have become hot spots for various pharmaceutical companies and research units, however, there are no reports of related drugs at present.

SUMMARY OF INVENTION

The purpose of the present invention is to solve the above-mentioned problems, and one object of the present invention is to provide a compound which can be used as a small-molecule allosteric activator capable of regulating the deacetylation activity of the SIRT6, to lay a foundation for the research of chemical biology related to SIRT6 and the exploration of the therapeutic effect of SIRT6 in diseases.

In order to achieve the purpose of the present invention, a compound or a pharmacologically acceptable salt thereof is firstly provided, which can be used as a SIRT6 small-molecule allosteric activator. The compound is represented by the formula (I):

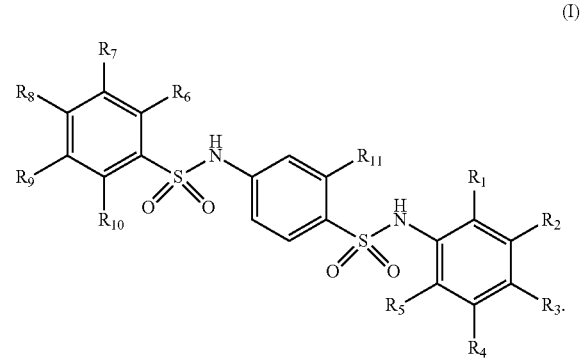

(I)

Wherein $R_1$, $R_2$, $R_3$, $R_4$, $R_5$, $R_6$, $R_7$, $R_8$, $R_9$ and $R_{10}$ are independently selected from a group consisting of H, halogen, hydroxyl, nitro, amino, carboxyl, acid ester group, sulfonamide, mercapto, methoxy, ethoxy, benzyloxy, methyl and cyano; $R_{11}$ is H, Cl, nitro, amino, benzyl alcohol, benzyl chloride, benzylamine, carboxyl,

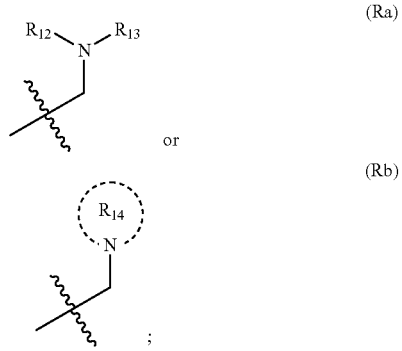

(Ra)

or (Rb)

;

$R_{12}$ and $R_{13}$ are independently substituted or unsubstituted C1-8 alkyl;

represents substituted or unsubstituted nitrogen-containing heterocyclic ring.

It should be noted that the compound of formula (I) has a symmetrical structure. That is, the selection of $R_1$, $R_2$, $R_3$, $R_4$, $R_5$, $R_6$, $R_7$, $R_8$, $R_9$ and $R_{10}$ needs to satisfy the symmetry of the compound of formula (I).

In one embodiment of the invention, when $R_{11}$ is

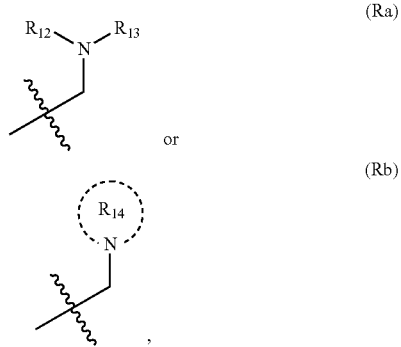

the compound has the structure shown in the formula (I-2) and formula (I-3):

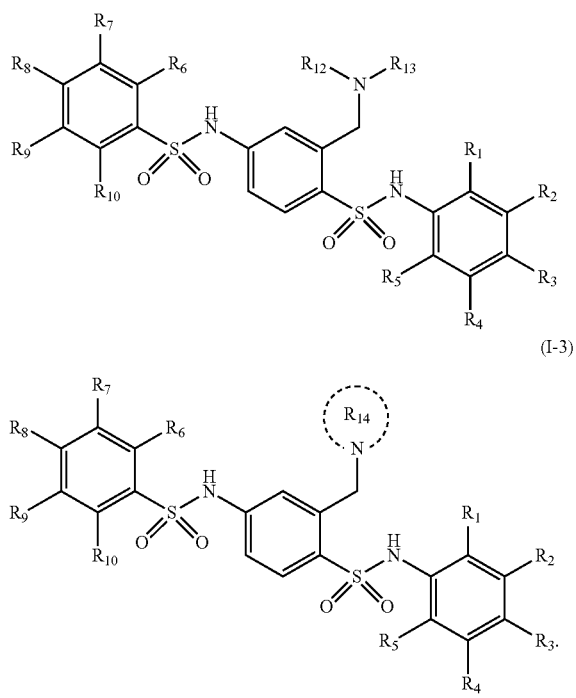

In one embodiment of the present invention, $R_{12}$ and $R_{13}$ are independently selected from a group consisting of methyl, ethyl, propyl, isopropyl, n-butyl, isobutyl, tert-butyl, n-pentyl, 2-methylbutane and hexyl.

In one embodiment of the invention, the nitrogen-containing heterocyclic ring is azacyclopropane, azetidine, pyrazole ring, morpholine ring, piperdine ring, piperazine ring, azacycloheptane or azacyclooctane.

In one embodiment of the present invention, at least one hydrogen atom in the nitrogen-containing heterocyclic ring is substituted by a substituent selected from a group consisting of methyl, ethyl, carboxyl, acid ester, carboxyl, methanol, cyclopropyl, isopropyl, cyclobutyl, cyclohexyl, cyclopentyl, oxy-substituted alkyl, and propenyl.

In one embodiment of the invention, the pharmacologically acceptable salt is sodium salt, hydrochloride, sulfate, oxalate, acetate, trifluoroacetic acid salt or citrate.

The invention also provides a SIRT6 small-molecule allosteric activator which comprises any one of the compounds or a pharmacologically acceptable salt thereof.

The present invention also provides a pharmaceutical composition comprising any of the above compounds or a pharmacologically acceptable salt thereof.

DESCRIPTION OF DRAWINGS

The above and other objects, features and advantages of the present invention will be apparent from the following detailed description and the accompanying drawings, in which.

DETAILED DESCRIPTION OF PREFERRED EMBODIMENTS

Figure 1:
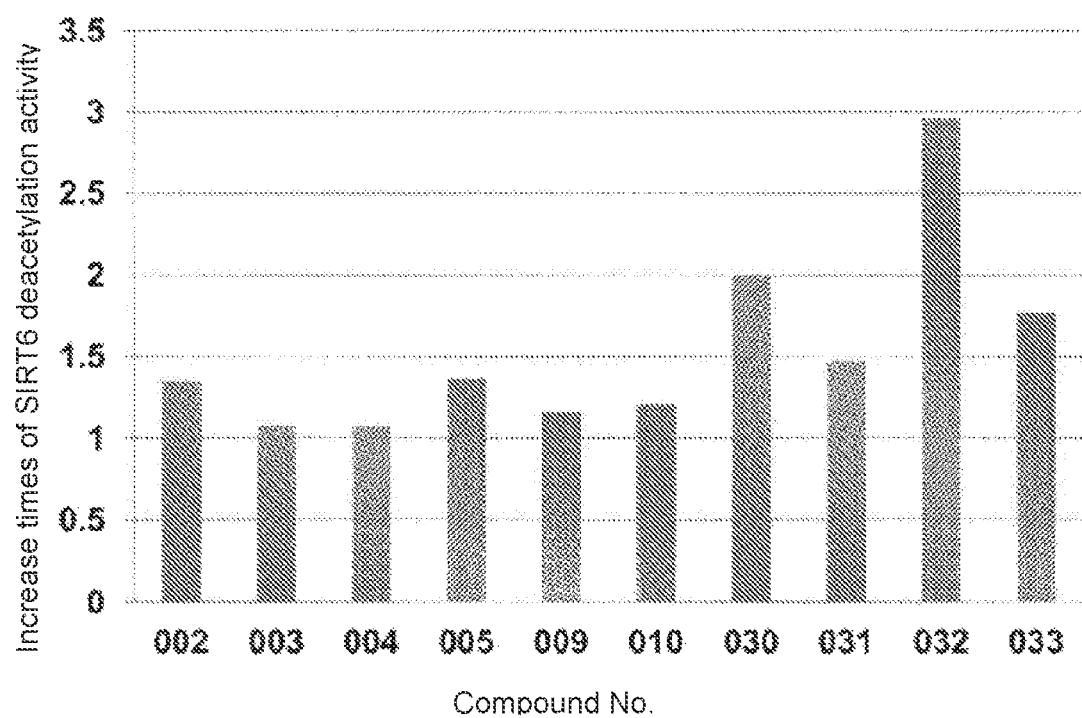
FIG. 1 to FIG. 8 are deacetylation activity data of SIRT6 treated by the SIRT6 small-molecule allosteric activator obtained by an FDL experiment.
Figure 2:
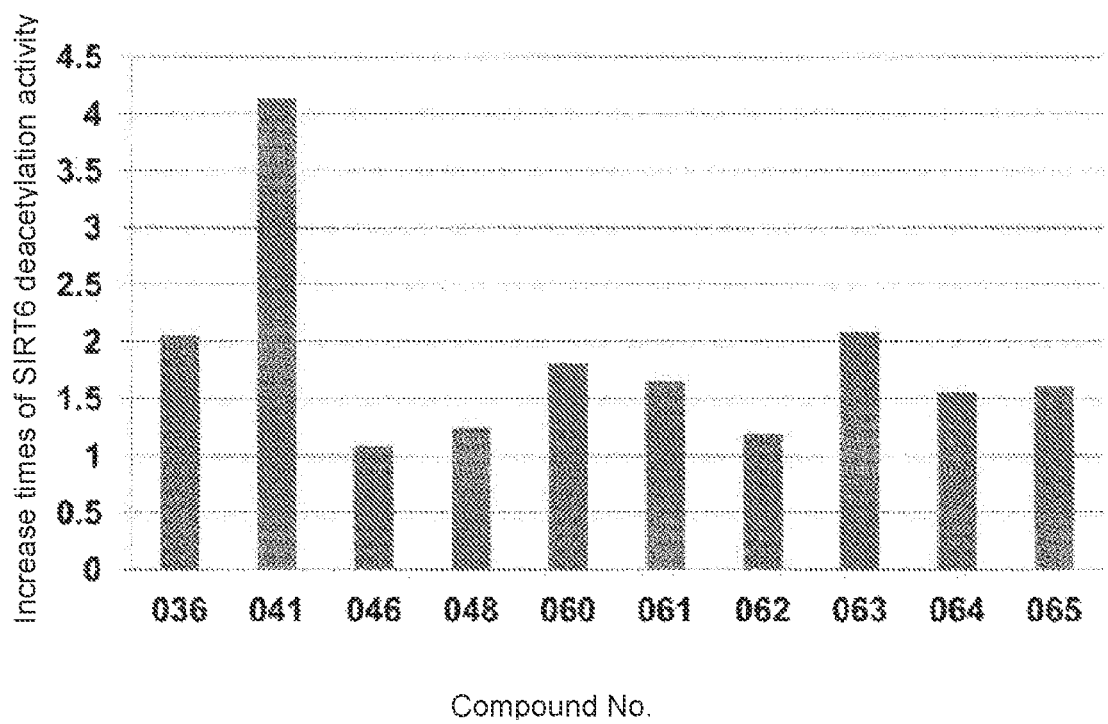
Figure 3:
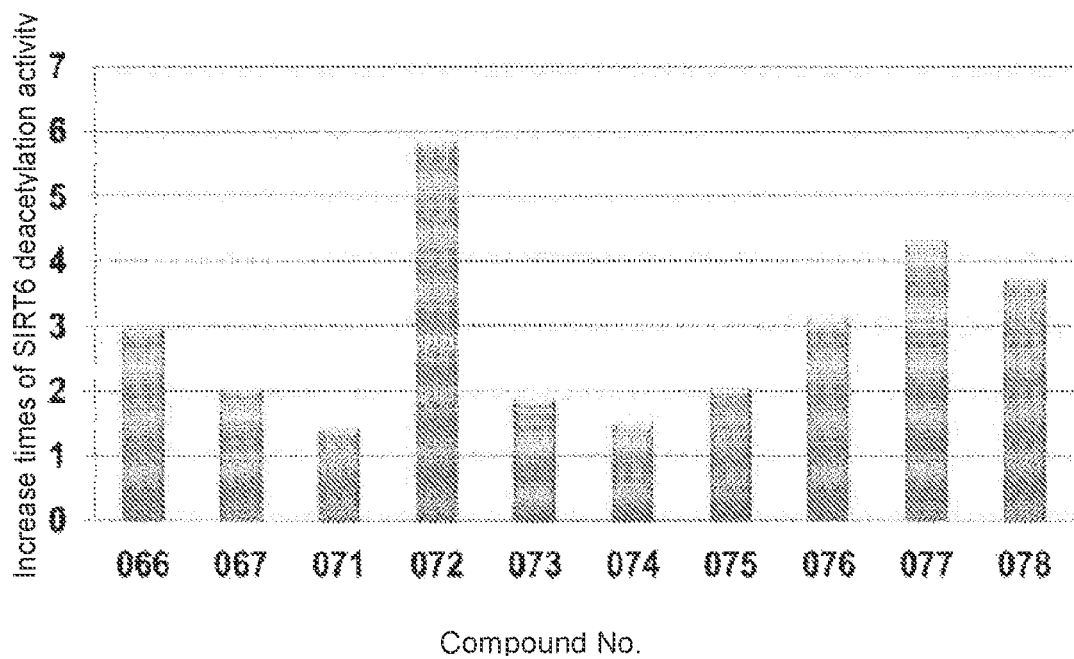
Figure 4:
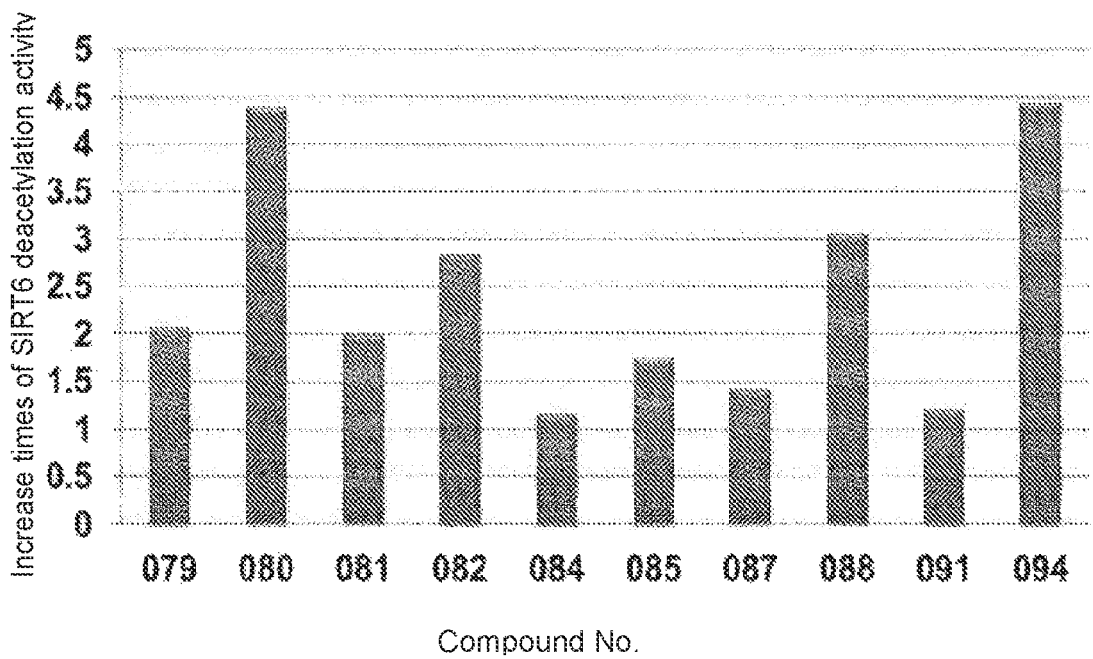
Figure 5:
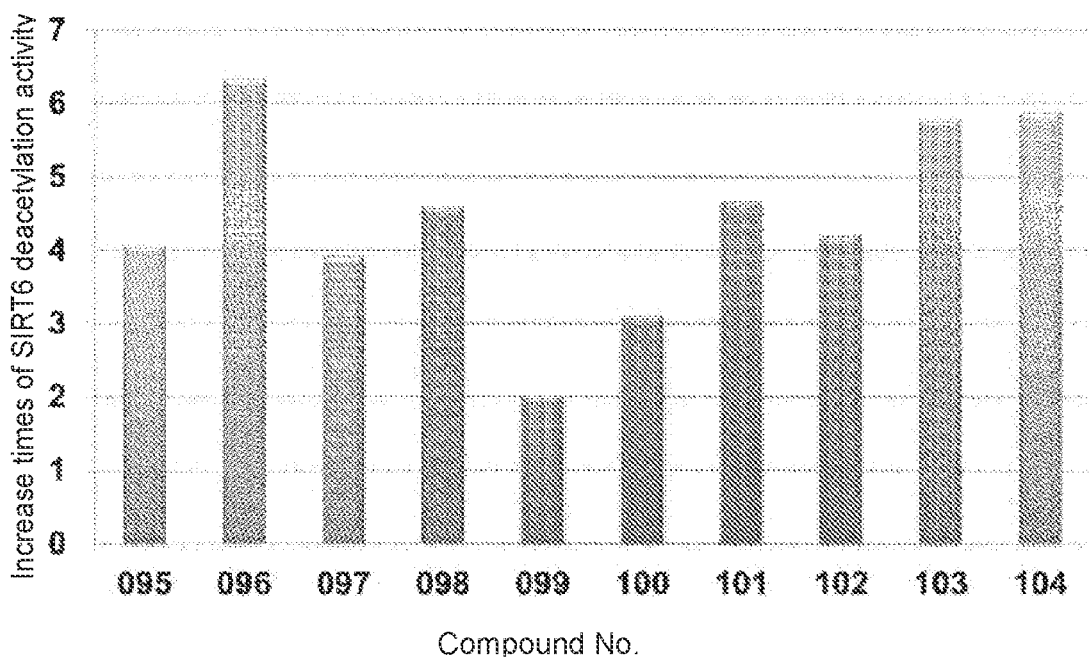
Figure 6:
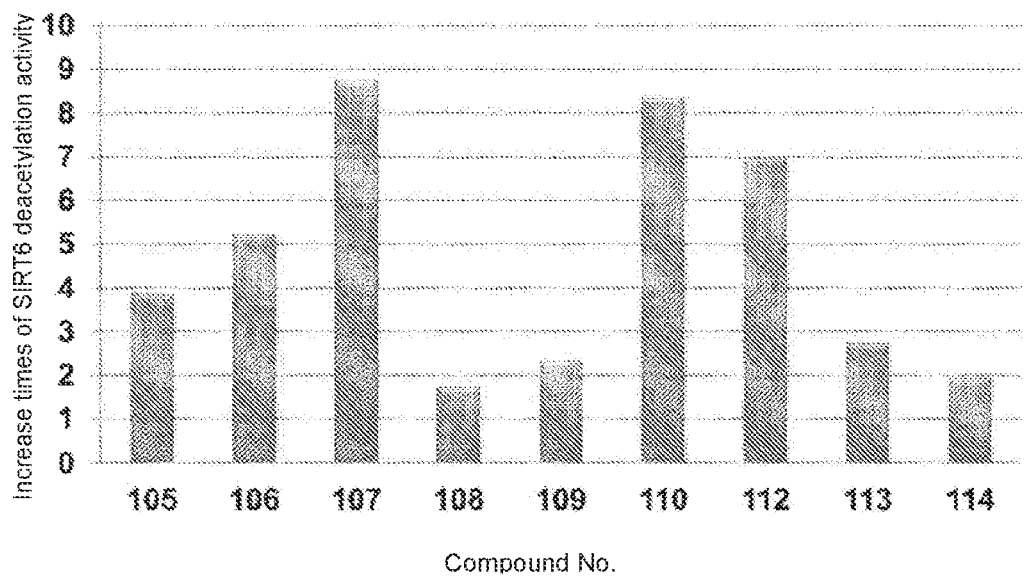
Figure 7:
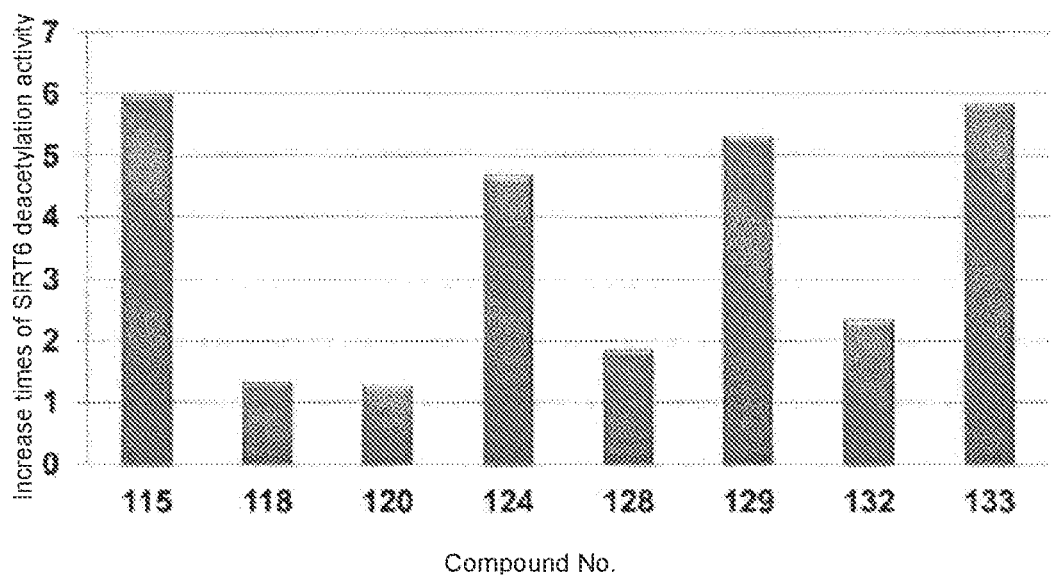
Figure 8:
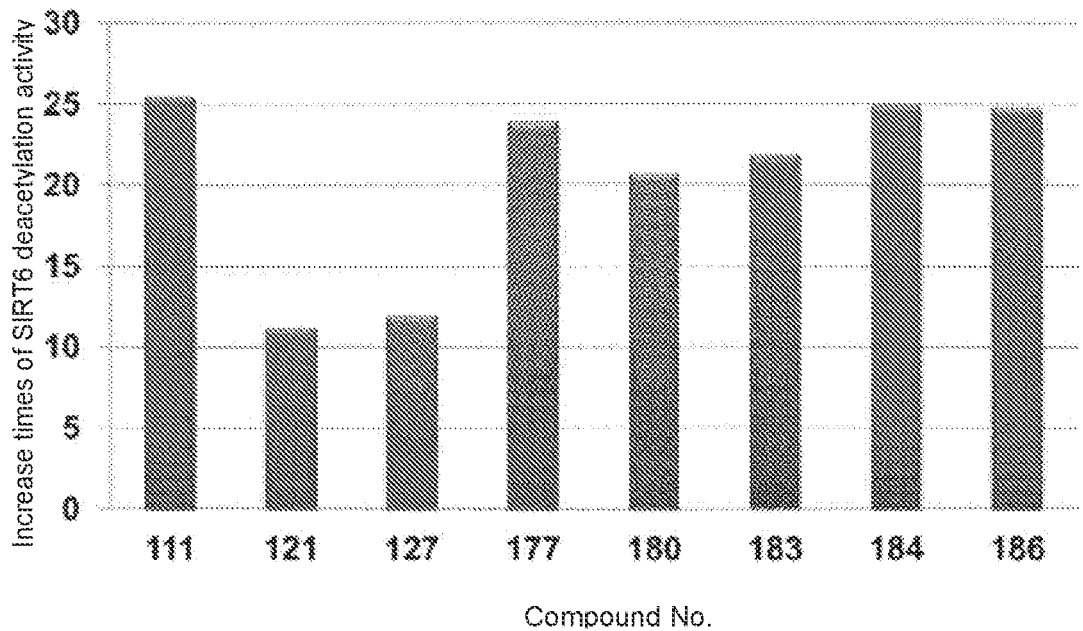

Some exemplary embodiments of the present invention will be described below with reference to the accompanying drawings, which are intended for purposes of illustration only and are not intended to limit the scope of the invention. In the following description, the same elements shown in the different drawings will be labeled with the same reference numerals. In addition, in the following description of the invention, detailed descriptions of the known functions and configurations contained herein will be omitted when the subject matter of the present invention will be rendered unclear.

The experimental methods used in the following examples are conventional methods unless otherwise specified. The materials, reagents, etc. used in the following examples, unless otherwise specified, can be obtained from commercial sources.

The experimental methods without specific conditions in the following examples usually refer to conventional conditions, such as the conditions described in Sambrook et al., Molecular Cloning: Laboratory Manual (New York: Cold Spring Harbor Laboratory Press, 1989), or refer to the conditions recommended by manufacturers.

Example 1. Synthesis of the Compound of Formula (I)

In the present embodiment, a compound of formula (I), or a pharmacologically acceptable salt thereof, is provided as a SIRT6 small molecule allosteric activator.

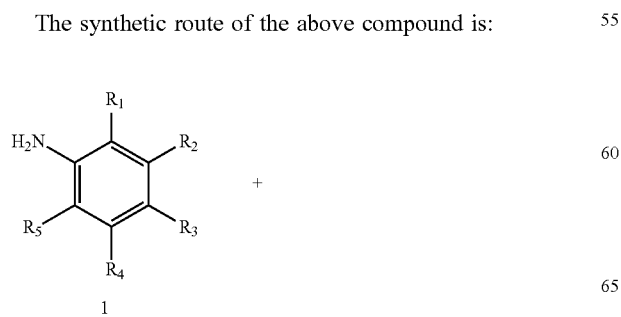

The synthetic route of the above compound is:

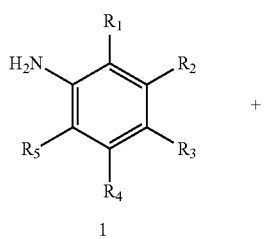

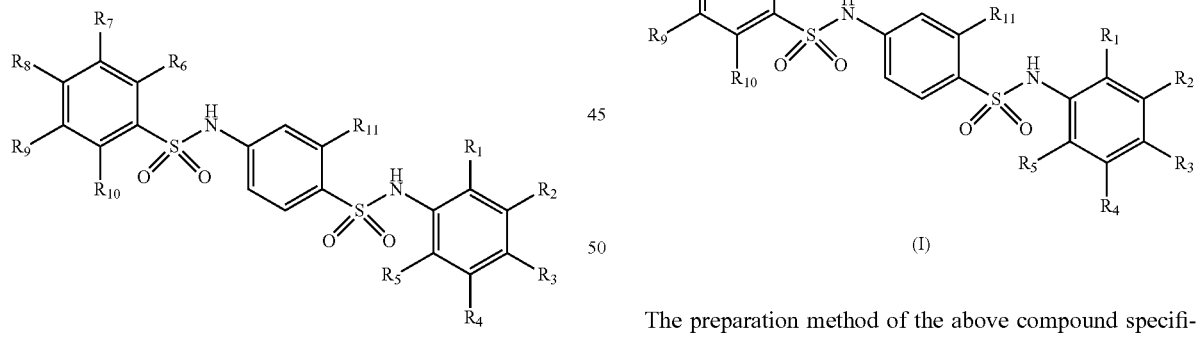

The preparation method of the above compound specifically comprises the following steps.

Step 1

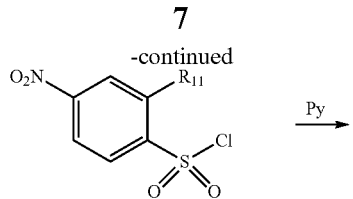

2

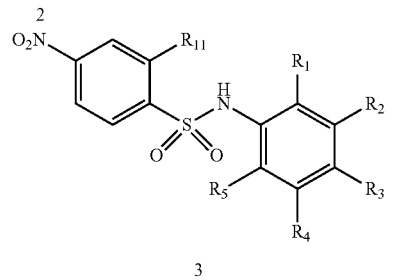

3

Take a round-bottomed flask of appropriate size and dissolve the aniline substituent Compound 1 in an appropriate amount of pyridine solution at room temperature. Then, 1.2 times equivalent of Compound 2 is added at the same temperature and stirred at room temperature for 10 minutes. Subsequently, the reaction temperature is increased to 75° C. to react for more than 8 hours. After the completion of the reaction monitored by TLC, the reaction system is cooled to room temperature, the pH value of the reaction system is adjusted to 3-4 with 2 mol/ml hydrochloric acid, and then ethyl acetate is added to extract for 3 times. After the organic phases is combined and washed with saturated brine for 3 times, the organic phase is dried with anhydrous sodium sulfate. After the ethyl acetate solution is distilled under reduced pressure, the residue obtained is Compound 3, which can be directly used in the next reaction.

Step 2

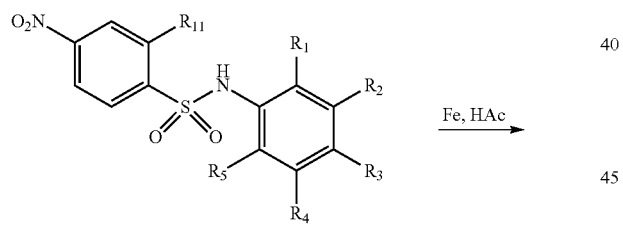

Compound 3 or different substituted compounds is dissolved with acetic acid at room temperature; 6 times equivalent of iron powder is added under the room temperature condition to react overnight at room temperature. The solvent is distilled under reduced pressure, then ethyl acetate is added and ultrasonicated for 10 minutes and then suction filtered. The filtrate is washed for 3 times with saturated sodium bicarbonate, and then washed for 3 times with saturated brine. The organic phase is dried with anhydrous sodium sulfate, separated and purified by column chromatography to obtain Compound 4.

Step 3

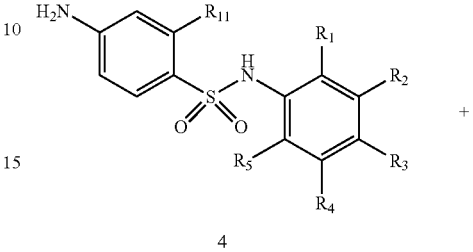

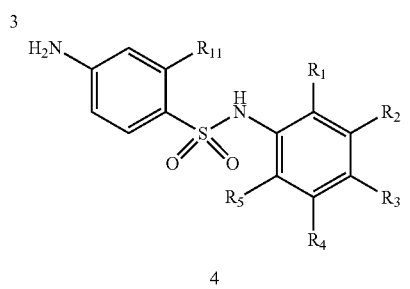

Compound 4 is dissolved in pyridine in a suitable round bottomed flask. 1.2 times equivalent of benzenesulfonyl chloride derivative 5 is added at room temperature, and then the reaction temperature is raised to 75° C. to react for more than 8 hours. After the completion of the reaction monitored by TLC, the reaction system is cooled to room temperature, the pH value of the reaction system is adjusted to 3-4 with 2 mol/ml hydrochloric acid, and then ethyl acetate is added to extract for 3 times. After the organic phase is combined and washed with saturated salt water for 3 times, and the organic phase is dried with anhydrous sodium sulfate. Then, the compound of formula (I) is obtained by column chromatography.

Example 2. Synthesis of the Compound of Formula (I)

In the present embodiment, a compound of formula (I), or a pharmacologically acceptable salt thereof, is provided as a SIRT6 small molecule allosteric activator.

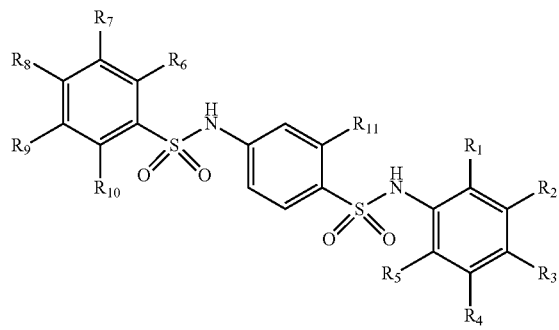

(I)

The synthetic route of the above compound is:

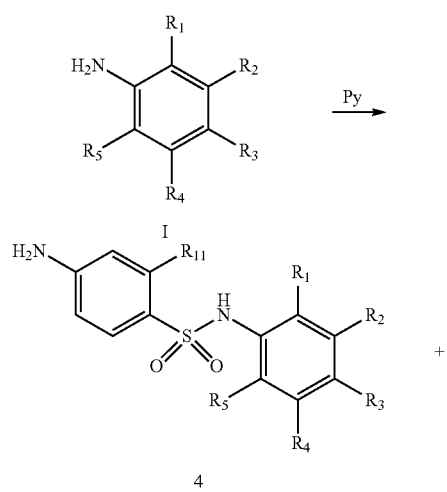

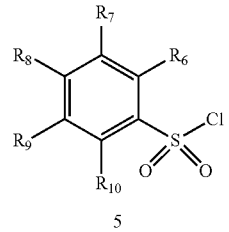

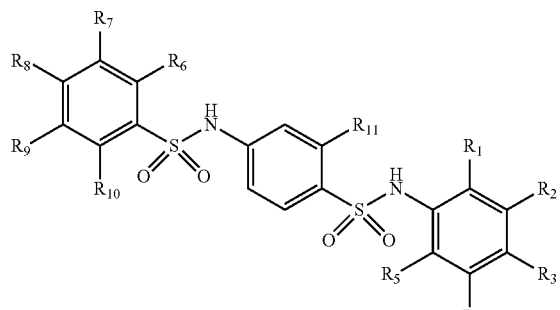

(I)

The preparation method of the above compound specifically comprises the following steps.

Step 1

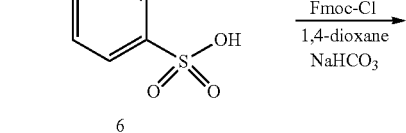

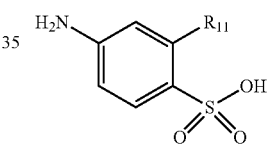

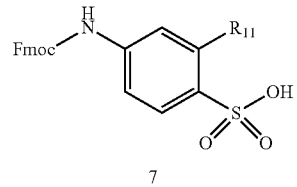

Take a suitable round-bottomed flask, aminobenzenesulfonic acid derivative 6 is added to an appropriate amount of water, 2.01 times equivalent of $NaHCO_3$ is added under the room temperature condition; the reaction is moved to 0° C. after stirring until the solution is clarified, and 1, 4-dioxane solution which dissolves Fmoc-Cl is slowly added into the round-bottomed flask at 0° C. After all the drops are added, stirring is continued for half an hour at 0° C., then the reaction system is moved to room temperature, and then the reaction system is reacted overnight. After the completion of the reaction monitored by TLC, the pH value of the reaction system is adjusted to 2 with 2 mol/ml hydrochloric acid at room temperature, and then under reduced pressure distillation, the solvent in the reaction bottle is completely distilled, dried for use, to obtain Compound 7.

Step 2

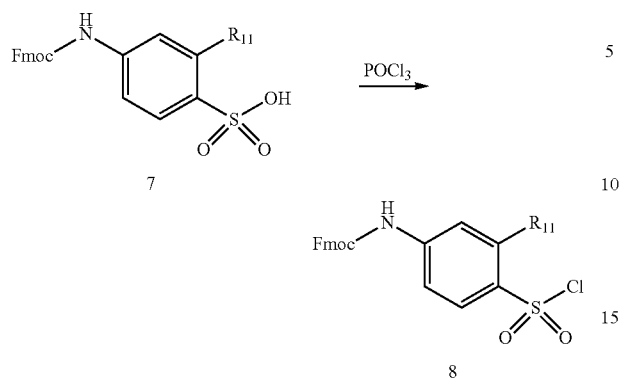

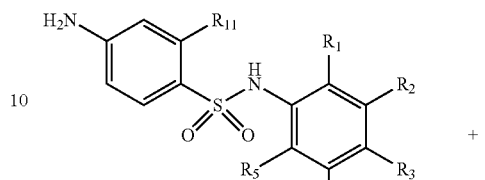

The dried Compound 7 is slowly added to phosphorus oxychloride under room temperature condition, and then reflux reaction is carried out under the protection of nitrogen overnight. After the reaction is completed, the solvent is completely reduced under reduced pressure, and then ethyl acetate and water are added; the organic phase is washed for 3 times with saturated salt water, dried with anhydrous sodium sulfate, and then column chromatography is carried out to obtain Compound 8.

Step 3

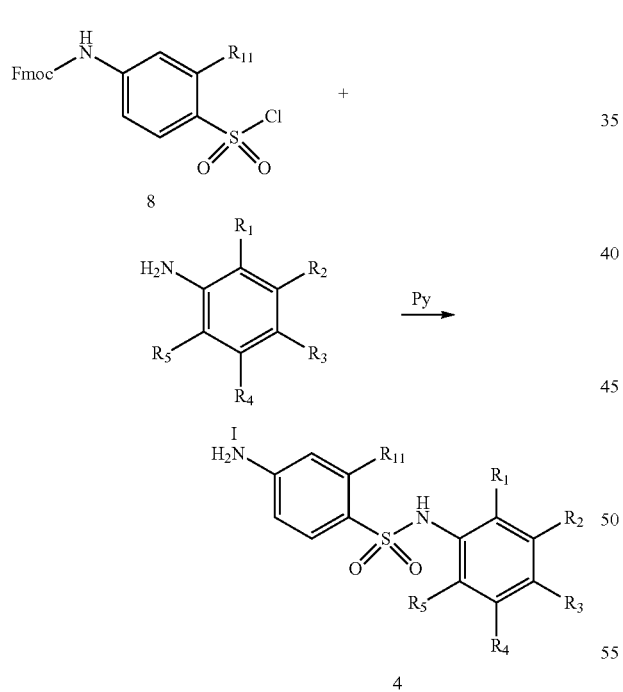

At room temperature, Compound 8 and aniline substituent 1 are dissolved in pyridine solution according to a mass ratio of 1.2:1, and then the reaction temperature is raised to 75° C. to react for more than 8 hours. After the completion of the reaction monitored by TLC, the reaction system is cooled to room temperature, the pH value of the reaction system is adjusted to 3-4 with 2 mol/ml hydrochloric acid, and then ethyl acetate is added to extract for 3 times. The organic phase is combined, washed for 3 times with saturated salt water, and the organic phase is dried by anhydrous sodium sulfate. Compound 4 is obtained by column chromatography separation and purification.

Step 4

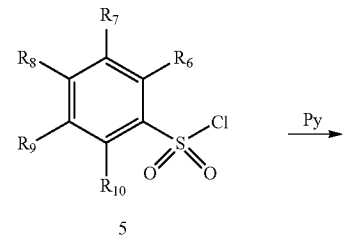

Compound 4 is dissolved in pyridine in a suitable round bottomed flask. 1.2 times equivalent of benzenesulfonyl chloride derivative 5 is added at room temperature, and then the reaction temperature is raised to 75° C. to react for more than 8 hours. After the completion of the reaction monitored by TLC, the reaction system is cooled to room temperature, the pH value of the reaction system is adjusted to 3-4 with 2 mol/ml hydrochloric acid, and then ethyl acetate is added to extract for 3 times. After the organic phase is combined and washed with saturated salt water for 3 times, and the organic phase is dried with anhydrous sodium sulfate. Then, the compound of formula (I) is obtained by column chromatography.

Example 3. Specific Structure of Compound of Formula (I)

Specific structures of compounds of formula (I) are described below in table form. The compound or the pharmacologically acceptable salt thereof for SIRT6 small-molecular aromatic activator of the present invention has any one of the structures listed in Table 1 below.

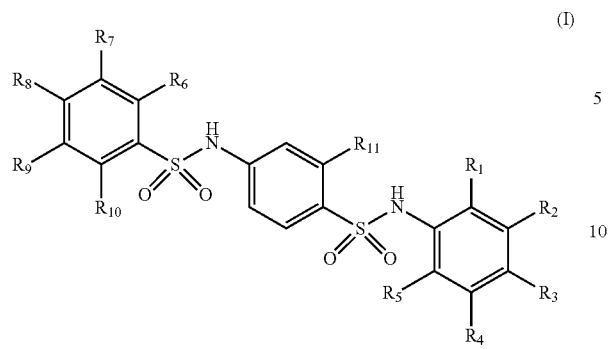

(I)

TABLE 1

Specific structure of compound (I)

| Compound No. | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 001 | Me | Cl | H | H | H | Cl | H | H | H | H | H |
| 002 | Me | Cl | H | H | H | Br | H | H | H | H | H |
| 003 | Me | Cl | H | H | H | F | H | H | H | H | H |
| 004 | Me | Cl | H | H | H | $NO_2$ | H | H | H | H | H |
| 005 | Me | Cl | H | H | H | $OCF_3$ | H | H | H | H | H |
| 006 | Me | Cl | H | H | H | CN | H | H | H | H | H |
| 007 | Me | Cl | H | H | H | NH2 | H | H | H | H | H |
| 008 | Me | Cl | H | H | H | COOH | H | H | H | H | H |
| 009 | Me | Cl | H | H | H | H | Br | H | H | H | H |
| 010 | Me | Cl | H | H | H | H | $CF_3$ | H | H | H | H |
| 011 | Me | Cl | H | H | H | H | F | H | H | H | H |
| 012 | Me | Cl | H | H | H | H | Cl | H | H | H | H |
| 013 | Me | Cl | H | H | H | H | $NO_2$ | H | H | H | H |
| 014 | Me | Cl | H | H | H | H | OMe | H | H | H | H |
| 015 | Me | Cl | H | H | H | H | CN | H | H | H | H |
| 016 | Me | Cl | H | H | H | H | COOH | H | H | H | H |
| 017 | Me | Cl | H | H | H | H | $SO_2Me$ | H | H | H | H |
| 018 | Me | Cl | H | H | H | H | $NH_2$ | H | H | H | H |
| 019 | Me | Cl | H | H | H | H | H | F | H | H | H |
| 020 | Me | Cl | H | H | H | H | H | Cl | H | H | H |
| 021 | Me | Cl | H | H | H | H | H | Br | H | H | H |
| 022 | Me | Cl | H | H | H | H | H | OMe | H | H | H |
| 023 | Me | Cl | H | H | H | H | H | $NH_2$ | H | H | H |
| 024 | Me | Cl | H | H | H | H | H | $CF_3$ | H | H | H |
| 025 | Me | Cl | H | H | H | H | H | $OCF_3$ | H | H | H |
| 026 | Me | Cl | H | H | H | H | H | CN | H | H | H |
| 027 | Me | Cl | H | H | H | H | H | $C(CH_3)_3$ | H | H | H |
| 028 | Me | Cl | H | H | H | H | H | COOH | H | H | H |
| 029 | Me | Cl | H | H | H | Cl | Cl | H | H | H | H |
| 030 | Me | Cl | H | H | H | Cl | H | Cl | H | H | H |
| 031 | Me | Cl | H | H | H | Cl | H | F | H | H | H |
| 032 | Me | Cl | H | H | H | Cl | H | H | Cl | H | H |
| 033 | Me | Cl | H | H | H | Cl | H | H | H | Cl | H |
| 034 | Me | Cl | H | H | H | F | Cl | H | H | H | H |
| 035 | Me | Cl | H | H | H | OMe | H | OMe | H | H | H |
| 036 | Me | Cl | H | H | H | OMe | H | H | Cl | H | H |
| 037 | Me | Cl | H | H | H | H | Me | Br | H | H | H |
| 038 | Me | Cl | H | H | H | H | $CF_3$ | Cl | H | H | H |
| 039 | Me | Cl | H | H | H | H | $CF_3$ | F | H | H | H |
| 040 | Me | Cl | H | H | H | H | Cl | OMe | H | H | H |
| 041 | Me | Cl | H | H | H | H | Cl | H | Cl | H | H |
| 042 | Me | Cl | H | H | H | H | H | Br | F | H | H |
| 043 | Me | Cl | H | H | H | H | H | OMe | F | H | H |
| 044 | Me | Cl | H | H | H | H | OMe | OMe | H | H | H |
| 045 | Me | Cl | H | H | H | H | H | OMe | H | $NO_2$ | H |
| 046 | Me | Cl | H | H | H | OMe | H | H | Br | H | H |
| 047 | Me | Cl | H | H | H | H | H | OMe | H | $NH_2$ | H |
| 048 | Me | Cl | H | H | H | H | H | $NO_2$ | Me | H | H |
| 049 | Me | Cl | H | H | H | H | H | $NO_2$ | H | H | H |
| 050 | H | $CF_3$ | H | H | H | H | H | OMe | Cl | H | H |
| 051 | Br | H | H | H | H | H | H | OMe | F | H | H |
| 052 | Me | H | Me | H | H | H | H | OMe | F | H | H |
| 053 | H | H | Cl | H | H | H | H | OMe | F | H | H |
| 054 | H | H | Cl | H | H | H | H | OMe | Br | H | H |

TABLE 1-continued

Specific structure of compound (I)

| Compound No. | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 055 | H | $CF_3$ | H | H | H | H | H | OMe | Br | H | H |
| 056 | Me | H | Me | H | H | H | H | OMe | Br | H | H |
| 057 | H | Me | H | H | H | H | H | OMe | Br | H | H |
| 058 | H | F | H | H | H | H | H | OMe | Br | H | H |
| 059 | H | OMe | H | H | H | H | H | OMe | Br | H | H |
| 060 | Me | H | H | H | H | H | Cl | H | Cl | H | H |
| 061 | H | Me | H | H | H | H | Cl | H | Cl | H | H |
| 062 | Cl | H | H | H | H | H | Cl | H | Cl | H | H |
| 063 | H | Cl | H | H | H | H | Cl | H | Cl | H | H |
| 064 | H | H | Cl | H | H | H | Cl | H | Cl | H | H |
| 065 | Br | H | H | H | H | H | Cl | H | Cl | H | H |
| 066 | H | Br | H | H | H | H | Cl | H | Cl | H | H |
| 067 | H | H | Br | H | H | H | Cl | H | Cl | H | H |
| 068 | OMe | H | H | H | H | H | Cl | H | Cl | H | H |
| 069 | H | OMe | H | H | H | H | Cl | H | Cl | H | H |
| 070 | H | H | OMe | H | H | H | Cl | H | Cl | H | H |
| 071 | $OCF_3$ | H | H | H | H | H | Cl | H | Cl | H | H |
| 072 | H | $OCF_3$ | H | H | H | H | Cl | H | Cl | H | H |
| 073 | H | H | $OCF_3$ | H | H | H | Cl | H | Cl | H | H |
| 074 | Me | Cl | H | H | H | Br | H | H | $CF_3$ | H | H |
| 075 | Me | Cl | H | H | H | H | $CF_3$ | H | $CF_3$ | H | H |
| 076 | Me | Cl | H | H | H | H | Br | H | $CF_3$ | H | H |
| 077 | Me | Cl | H | H | H | H | Br | H | Cl | H | H |
| 078 | Me | Cl | H | H | H | Br | H | H | Br | H | H |
| 079 | Me | Cl | H | H | H | $CF_3$ | H | H | $CF_3$ | H | H |
| 080 | Me | Cl | H | H | H | H | Br | H | Br | H | H |
| 081 | Me | Cl | H | H | H | Br | H | Br | H | H | H |
| 082 | Me | Cl | H | H | H | H | Cl | H | $CF_3$ | H | H |
| 083 | Me | Cl | H | H | H | H | $OCF_3$ | H | H | H | H |
| 084 | H | H | H | H | H | H | Cl | H | Cl | H | H |
| 085 | H | F | H | H | H | H | Cl | H | Cl | H | H |
| 086 | F | H | H | H | H | H | Cl | H | Cl | H | H |
| 087 | $CF_3$ | H | H | H | H | H | Cl | H | Cl | H | H |
| 088 | H | H | F | H | H | H | Cl | H | Cl | H | H |
| 089 | CN | H | H | H | H | H | Cl | H | Cl | H | H |
| 090 | H | H | CN | H | H | H | Cl | H | Cl | H | H |
| 091 | H | H | $CF_3$ | H | H | H | Cl | H | Cl | H | H |
| 092 | Me | Cl | H | H | H | H | H | OMe | H | H | H |
| 093 | Me | Cl | H | H | H | H | $CF_3$ | H | H | H | H |
| 094 | Me | Cl | H | H | H | H | Cl | H | Cl | H | H |
| 095 | H | $CF_3$ | H | H | H | H | Cl | H | Cl | H | H |
| 096 | Br | H | F | H | H | H | Cl | H | Cl | H | H |
| 097 | Cl | H | F | H | H | H | Cl | H | Cl | H | H |
| 098 | $CF_3$ | H | F | H | H | H | Cl | H | Cl | H | H |
| 099 | F | H | F | H | H | H | Cl | H | Cl | H | H |
| 100 | H | F | F | H | H | H | Cl | H | Cl | H | H |
| 101 | H | Br | H | Br | H | H | Cl | H | Cl | H | H |
| 102 | Cl | H | H | Br | H | H | Cl | H | Cl | H | H |
| 103 | H | Br | H | Cl | H | H | Cl | H | Cl | H | H |
| 104 | Me | Br | H | Cl | H | H | Cl | H | Cl | H | H |
| 105 | Me | Br | H | F | H | H | Cl | H | Cl | H | H |
| 106 | H | $CF_3$ | F | H | H | H | Cl | H | Cl | H | H |
| 107 | H | Cl | F | H | H | H | Cl | H | Cl | H | H |
| 108 | H | F | F | F | H | H | Cl | H | Cl | H | H |
| 109 | F | H | H | F | F | H | Cl | H | Cl | H | H |
| 110 | H | Me | F | H | H | H | Cl | H | Cl | H | H |
| 111 | Me | H | F | H | Br | H | Cl | H | Cl | H | H |
| 112 | H | $CF_3$ | H | Br | H | H | Cl | H | Cl | H | H |
| 113 | H | Br | Me | H | H | H | Cl | H | Cl | H | H |
| 114 | H | Br | CN | H | H | H | Cl | H | Cl | H | H |
| 115 | CN | Br | H | H | H | H | Cl | H | Cl | H | H |
| 116 | H | OH | H | H | H | H | Cl | H | Cl | H | H |
| 117 | OH | H | H | H | H | H | Cl | H | Cl | H | H |
| 118 | COOMe | H | H | H | H | H | Cl | H | Cl | H | H |
| 119 | H | H | OBn | H | H | H | Cl | H | Cl | H | H |
| 120 | H | H | Me | H | H | H | Cl | H | Cl | H | H |
| 121 | Me | H | H | Br | H | H | Cl | H | Cl | H | H |
| 122 | COOH | H | H | H | H | H | Cl | H | Cl | H | H |
| 123 | H | COOMe | H | H | H | H | Cl | H | Cl | H | H |
| 124 | Me | Br | H | H | H | H | Cl | H | Cl | H | H |
| 125 | H | H | COOMe | H | H | H | Cl | H | Cl | H | H |
| 126 | H | COOH | H | H | H | H | Cl | H | Cl | H | H |
| 127 | Me | H | F | H | H | H | Cl | H | Cl | H | H |
| 128 | F | H | H | Br | H | H | Cl | H | Cl | H | H |
| 129 | H | OBn | H | H | H | H | Cl | H | Cl | H | H |

TABLE 1-continued

Specific structure of compound (I)

| Compound No. | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 130 | H | H | COOH | H | H | H | Cl | H | Cl | H | H |
| 131 | H | CN | H | H | H | H | Cl | H | Cl | H | H |
| 132 | OBn | H | H | H | H | H | Cl | H | Cl | H | H |
| 133 | H | OCF$_3$ | H | H | H | H | Cl | H | Cl | H | H |
| 134 | H | H | F | H | H | H | H | Me | H | H | H |
| 135 | H | CF$_3$ | Cl | H | H | H | Br | OMe | H | H | H |
| 136 | Me | Cl | H | H | H | H | Br | OMe | H | H | H |
| 137 | H | H | Cl | H | H | H | OMe | OMe | H | H | H |
| 138 | H | CF$_3$ | H | H | H | H | OMe | OMe | H | H | H |
| 139 | H | H | Cl | H | H | H | Br | OMe | H | H | H |
| 140 | H | Me | H | H | H | Cl | Cl | OMe | H | H | H |
| 141 | H | Me | H | H | H | Cl | H | H | Cl | H | H |
| 142 | H | CF$_3$ | H | Cl | H | H | Cl | H | Cl | H | H |
| 143 | H | Br | H | F | H | H | Cl | H | Cl | H | H |
| 144 | Me | H | Me | H | H | Cl | H | Cl | H | H | H |
| 145 | H | H | OMe | H | H | Cl | H | H | Cl | H | H |
| 146 | H | H | OMe | H | H | NO$_2$ | H | H | H | H | H |
| 147 | Me | Cl | H | H | H | NO$_2$ | H | H | H | H | H |
| 148 | Me | Cl | H | H | H | H | NO$_2$ | Me | H | H | H |
| 149 | H | Me | H | Me | H | H | H | Cl | H | H | H |
| 150 | Me | H | Me | H | H | H | H | Me | H | H | H |
| 151 | H | Me | H | Me | H | H | H | Me | H | H | H |
| 152 | H | H | F | H | H | H | H | Cl | H | H | H |
| 153 | H | H | Cl | H | H | H | H | OEt | H | H | H |
| 154 | H | H | OMe | H | H | Cl | Cl | OMe | H | H | H |
| 155 | OMe | H | H | Me | H | H | H | OEt | H | H | H |
| 156 | H | H | Me | H | H | H | H | OEt | H | H | H |
| 157 | H | H | H | H | H | H | H | OEt | H | H | H |
| 158 | Cl | H | Cl | H | H | Cl | Cl | OMe | H | H | H |
| 159 | Me | H | Me | H | H | Cl | Cl | OMe | H | H | H |
| 160 | Me | H | H | H | H | Me | H | Me | H | Me | H |
| 161 | H | Cl | H | Cl | H | H | Me | OMe | H | H | H |
| 162 | H | CF$_3$ | Cl | H | H | H | Me | OMe | H | H | H |
| 163 | Cl | H | H | H | H | Me | H | Me | H | Me | H |
| 164 | H | H | F | H | H | H | Me | OMe | H | H | H |
| 165 | H | H | Cl | H | H | H | Me | OMe | H | H | H |
| 166 | H | CF$_3$ | H | H | H | H | Me | OMe | H | H | H |
| 167 | H | H | OEt | H | H | Me | H | Me | H | Me | H |
| 168 | H | H | Br | H | H | H | Me | OMe | H | H | H |
| 169 | Me | H | H | Cl | H | Cl | Cl | OMe | H | H | H |
| 170 | H | H | H | H | H | Cl | H | H | Cl | H | H |
| 171 | H | CF$_3$ | H | H | H | Cl | Cl | OMe | H | H | H |
| 172 | Br | H | F | OBn | H | H | Cl | H | Cl | H | H |
| 173 | Me | Cl | H | H | H | Br | Cl | H | Cl | H | H |
| 174 | Me | H | F | H | Br | Cl | Cl | H | Cl | H | H |
| 175 | Me | H | F | H | Br | Br | Cl | H | Cl | H | H |
| 176 | Me | Cl | H | H | H | Cl | Cl | H | Cl | H | H |
| 177 | Me | H | F | Br | H | H | Cl | H | Cl | H | H |
| 178 | H | OH | F | H | H | H | Cl | H | Cl | H | H |
| 179 | F | H | F | H | Br | H | Cl | H | Cl | H | H |
| 180 | Me | H | F | Br | H | H | Cl | H | Cl | H | Cl |
| 181 | Me | H | F | Br | H | H | Cl | H | Cl | H | NO$_2$ |
| 182 | Me | H | F | Br | H | H | Cl | H | Cl | H | NH$_2$ |
| 183 | Me | H | F | Br | H | H | Cl | H | Cl | H | COOMe |
| 184 | Me | H | F | Br | H | H | Cl | H | Cl | H | COOH |
| 185 | Me | H | F | Br | H | H | Cl | H | Cl | H | CH$_2$Cl |
| 186 | Me | H | F | Br | H | H | Cl | H | Cl | H | CH$_2$OH |
| 187 | Me | H | F | Br | H | H | Cl | H | Cl | H | CH$_2$NH$_2$ |

Example 4. Synthesis of the Compound of Formula (I-2) or Formula (I-3)
In the present embodiment, a compound of formula (I-2) or formula (I-3), or a pharmacologically acceptable salt thereof, is provided as a SIRT6 small molecule allosteric activator.
The synthetic route of the above compound is:
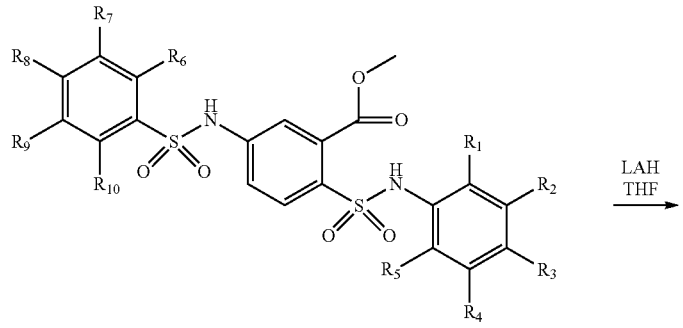
(a4)
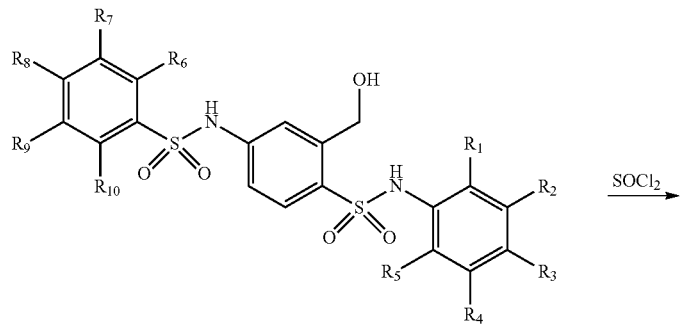
(a5)
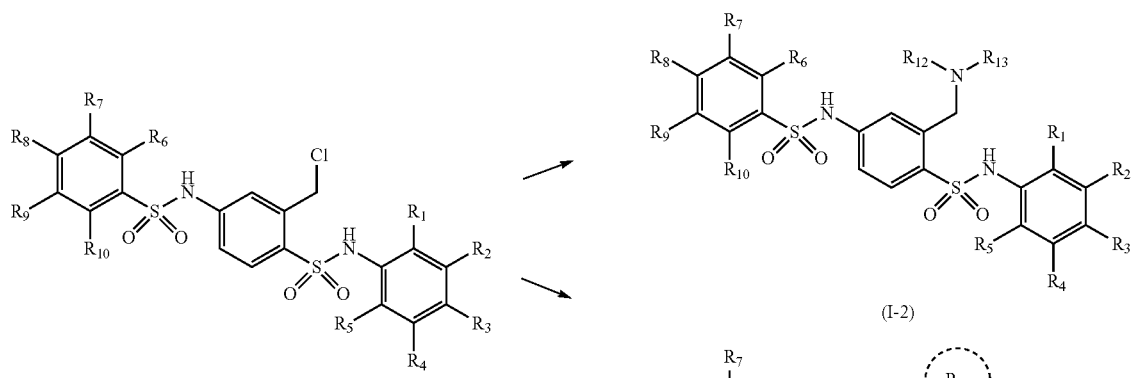
(a6)
(I-2)
(I-3)

The preparation method of the above compound specifically comprises the following steps.

Step 1

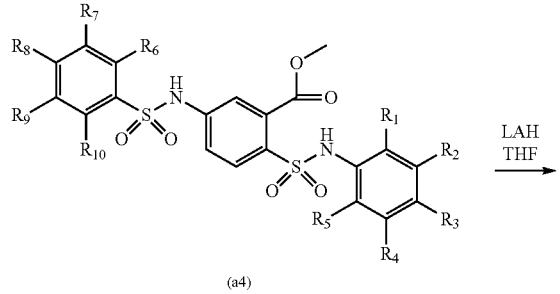

(a4)

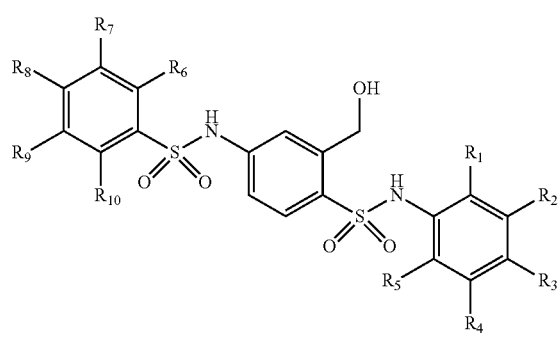

(a5)

In a reaction bottle, different substituted compounds containing the formula a4 are dissolved by anhydrous tetrahydrofuran, and 3 times equivalent of tetrahydrofuran solution of lithium tetrahydrate is slowly added in an ice bath. After all the ingredients are added, continue to stir in ice bath for 0.5 to 1 hour. The reaction system is moved to room temperature, and the reaction is heated to 70° C. for 4 hours. After the reaction is completed, the reaction system is firstly moved to room temperature, then the reaction liquid is slowly added into dilute hydrochloric acid with the pH value of 0° C., stirring continues until the solid is sufficiently precipitated. The liquid is filtered, a white solid is obtained and dried, and a benzyl alcohol compound containing the formula a5 is obtained. The crude product does not need to be purified and is directly used for the next reaction.

Step 2

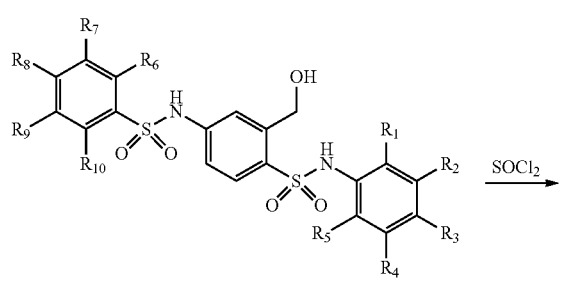

(a5)

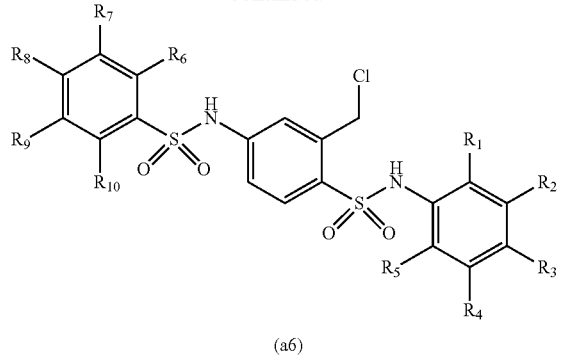

(a6)

In the ice bath, the benzyl alcohol compound of the formula a5 is slowly added into the dichlorosulfoxide in a reaction bottle, after the addition is completed, the benzyl alcohol compound is continuously stirred in an ice bath for half an hour and then rises to the room temperature. The reaction system is heated to 75° C. to react for 24 hours. After the reaction is completed, the reaction system is firstly moved to the room temperature, and then the reaction liquid is slowly added into an ice-water mixed aqueous solution. Continue to stir until the solid precipitates completely, then filter, dry and recrystallize to obtain the benzyl chloride compound of formula a6.

Step 3-1

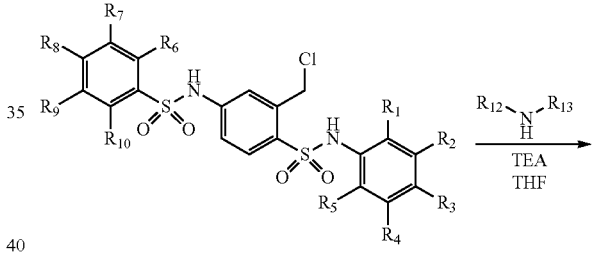

(a6)

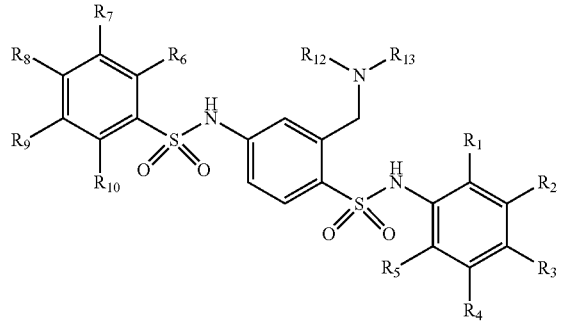

(I-2)

Under the condition of temperature, the benzyl chloride compound of the formula a6 is dissolved with tetrahydrofuran, then 1.5 times equivalent of substituted or different substituted aliphatic branched secondary amine is added, and then 2 times equivalent of triethylamine is added. The reaction is heated to 60° C. to react for 10 hours. After the reaction is completed, the reaction system is moved to room temperature, then water is added to extract with ethyl acetate for 3 times; the organic phase is combined and washed with saturated salt water for 3 times, and the compound of formula (I-2) is obtained by column chromatography.

Step 3-2

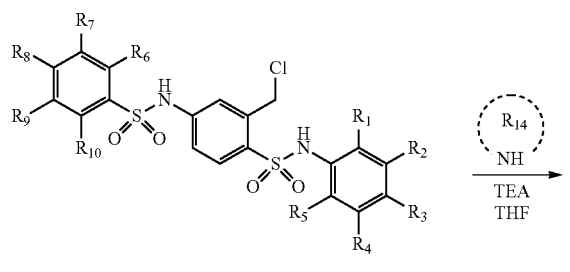

(a6)

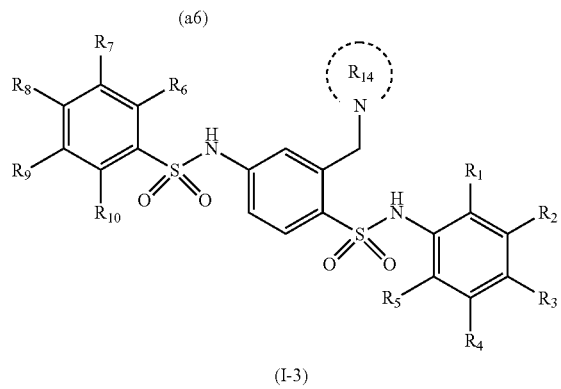

(I-3)

Under the room temperature condition, the benzyl chloride compound of formula 6 is dissolved by tetrahydrofuran in a reaction bottle, then 1.5 times equivalent of fat ring containing secondary amine and various substituents thereof are added, and then 2 times equivalent of triethylamine is added. The reaction is heated to 60° C. to react for 10 hours. After the reaction is completed, the reaction system is moved to room temperature, then water is added to extract with ethyl acetate for 3 times; the organic phase is combined and washed with saturated salt water for 3 times, and the compound of formula (I-3) is obtained by column chromatography.

Example 5. Synthesis of the Compound of Formula (I-2) or Formula (I-3)

In the present embodiment, a compound of formula (I-2) or formula (I-3), or a pharmacologically acceptable salt thereof, is provided as a SIRT6 small molecule allosteric activator.

The synthetic route of the above compound is:

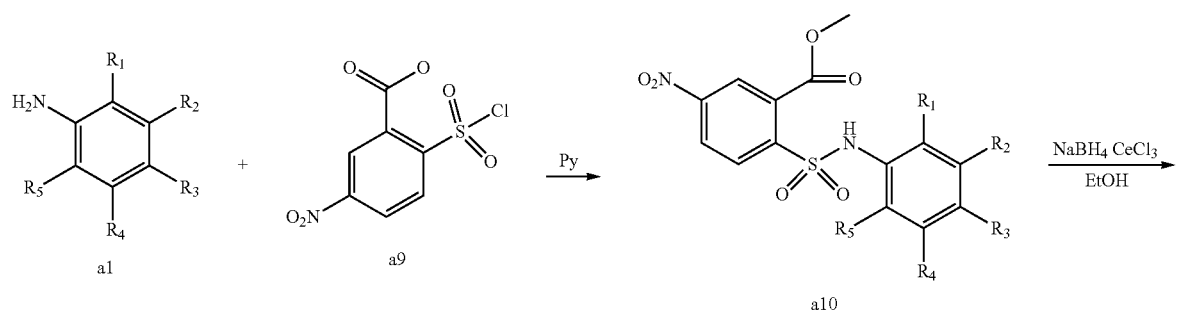

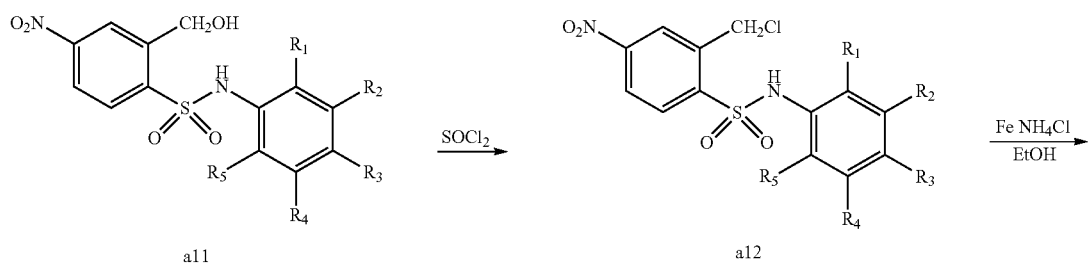

-continued
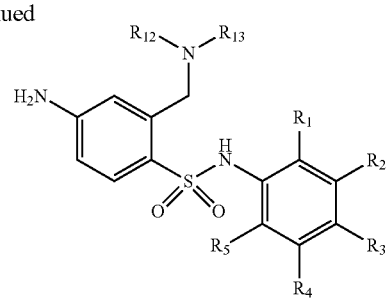
(a14)
or
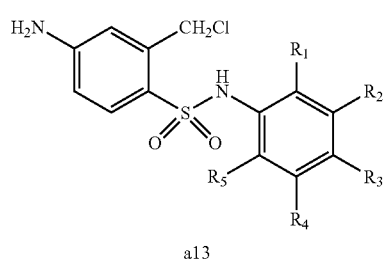  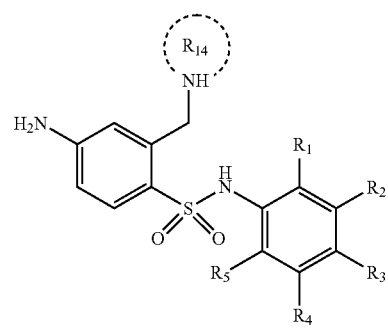 
a13
(a15)
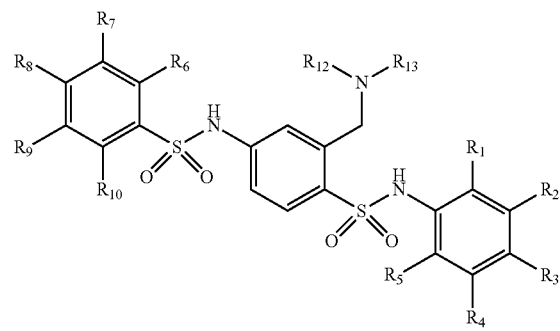
(I-2) or
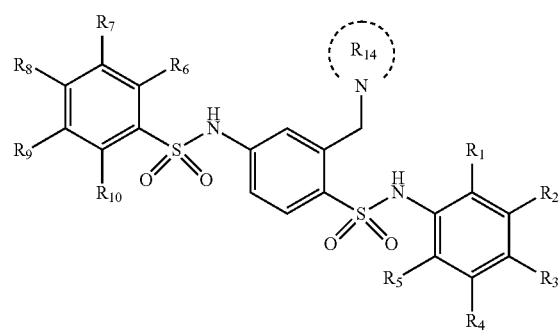
(I-3)

The preparation method of the above compound specifically comprises the following steps.

Step 1

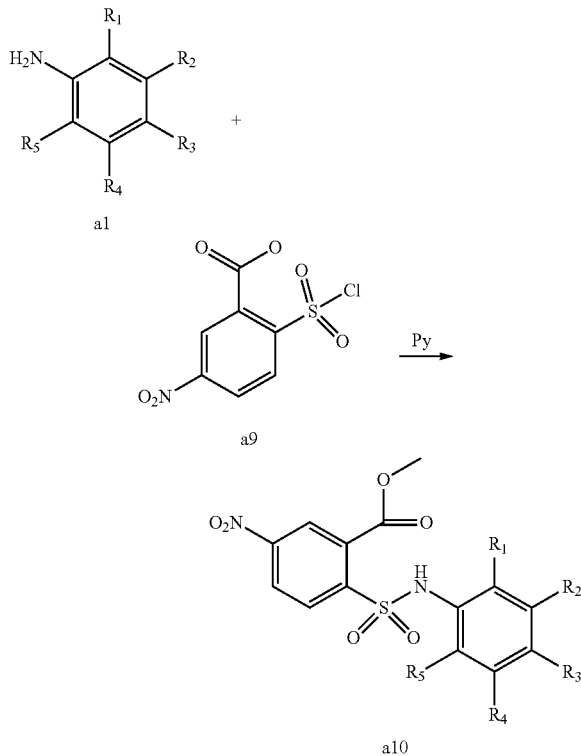

Take a round-bottomed flask of appropriate size and dissolve the aniline Compound a1 in an appropriate amount of pyridine solution at room temperature. Then, 1.2 times equivalent of Compound a9 is added at the same temperature and stirred at room temperature for 10 minutes. Subsequently, the reaction temperature is increased to 75° C. to react for more than 8 hours. After the completion of the reaction monitored by TLC, the reaction system is cooled to room temperature, the pH value of the reaction system is adjusted to 3-4 with 2 mol/ml hydrochloric acid, and then ethyl acetate is added to extract for 3 times. After the organic phases is combined and washed with saturated brine for 3 times, the organic phase is dried with anhydrous sodium sulfate. After the ethyl acetate solution is distilled under reduced pressure, the residue obtained is Compound a10, which can be directly used in the next reaction.

Step 2

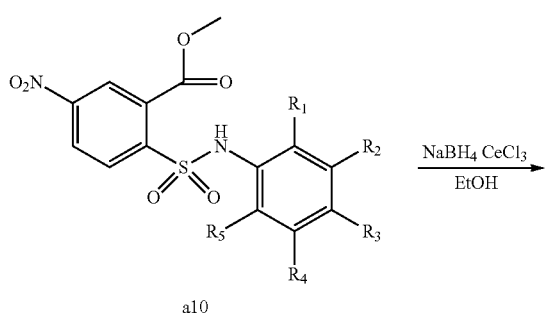

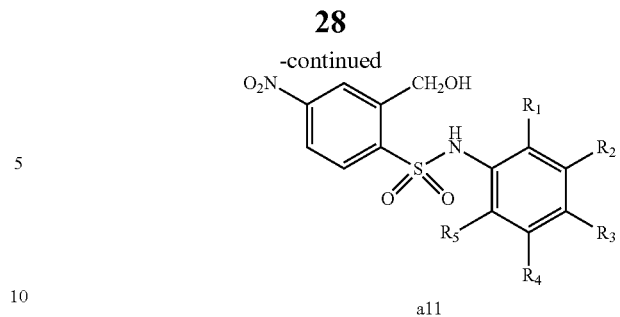

Compound a10 and absolute ethyl alcohol is added into the reaction bottle, adding cerium chloride into the ice bath, and slowly adding sodium borohydride in batches. Continuously reacting for 30 minutes at the same temperature after all the sodium borohydride is added, and then transferring to room temperature. Then heating to 50° C. to react for 4 hours. After the reaction is completed, the reaction system is cooled to room temperature, then 3 moL/L dilute hydrochloric acid is slowly added under the ice bath condition to adjust the pH value to 3, and the color of the solution is changed from orange-yellow to purple. After the ethanol solvent is concentrated under reduced pressure, the ethyl acetate is extracted for 3 times, and the organic phase is dried by anhydrous sodium sulfate. Column chromatography is then carried out to obtain white solids, namely the Compound a11.

Step 3

The Compound a11 is added into the reaction bottle, and after the thionyl chloride is slowly added in the ice bath, the reaction is moved to room temperature and then heated to 80° C. for reflux. After 4 hours of reaction, the reaction system is moved to room temperature. After the reaction liquid is quenched with ice and the reaction liquid is extracted for 3 times with ethyl acetate, the organic phase is washed for 3 times with saturated salt water, the organic phase is dried by anhydrous sodium sulfate, the organic phase is completely removed. Recrystallization is then carried out to obtain a white solid, namely the Compound a12.

Step 4

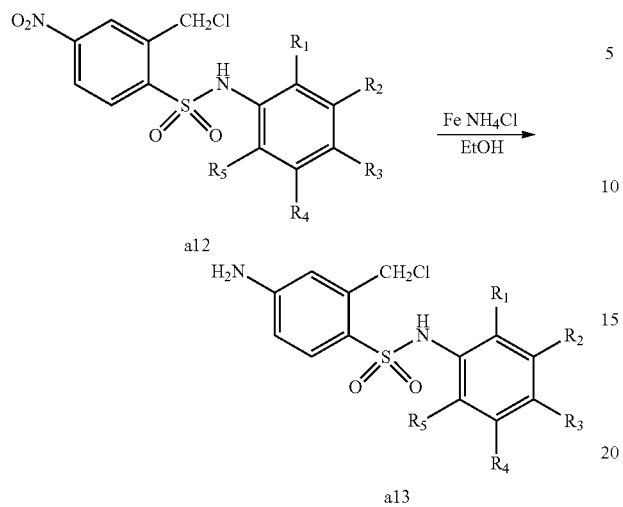

Compound a12 is dissolved in the reaction bottle with ethanol, a proper amount of saturated ammonium chloride solution is then added to stir evenly. 5 times equivalent of reduced iron powder is added in batches. Then the reaction is heated to 70° C. for reaction for 8 hours, and suction filtration is carried out while the filtrate is hot. After the filtrate is distilled under reduced pressure, ethyl acetate is added, and washed with saturated brine for 3 times. After the organic phase is dried with anhydrous sodium sulfate, column chromatography is performed to obtain a white solid, namely Compound a13.

Step 5-1

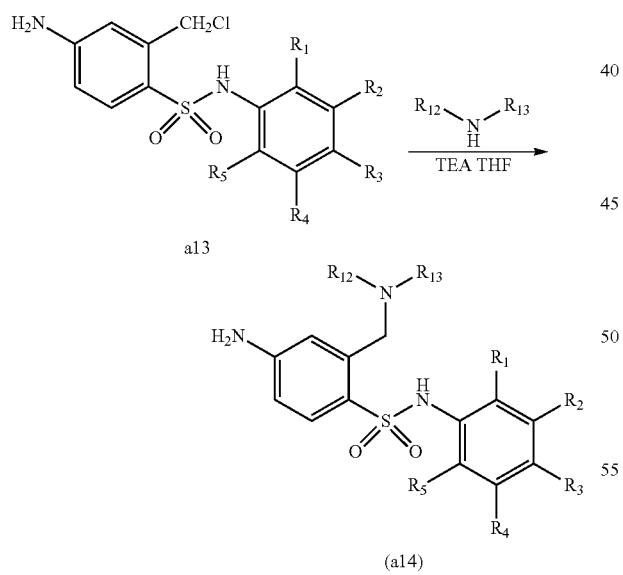

At room temperature, the Compound a13 in the reaction flask is dissolved in tetrahydrofuran, and then 1.5 times equivalent of aliphatic branch containing the same or differently substituted secondary amine is added. And then, 2 times equivalent of triethylamine is added. The reaction is heated to 60° C. to react for 10 hours. After the reaction is completed, the reaction system is moved to room tempera- ture, then water is added to extract with ethyl acetate for 3 times; the organic phase is combined and washed with saturated salt water for 3 times, and Compound 14 is obtained by column chromatography.

Step 6-1

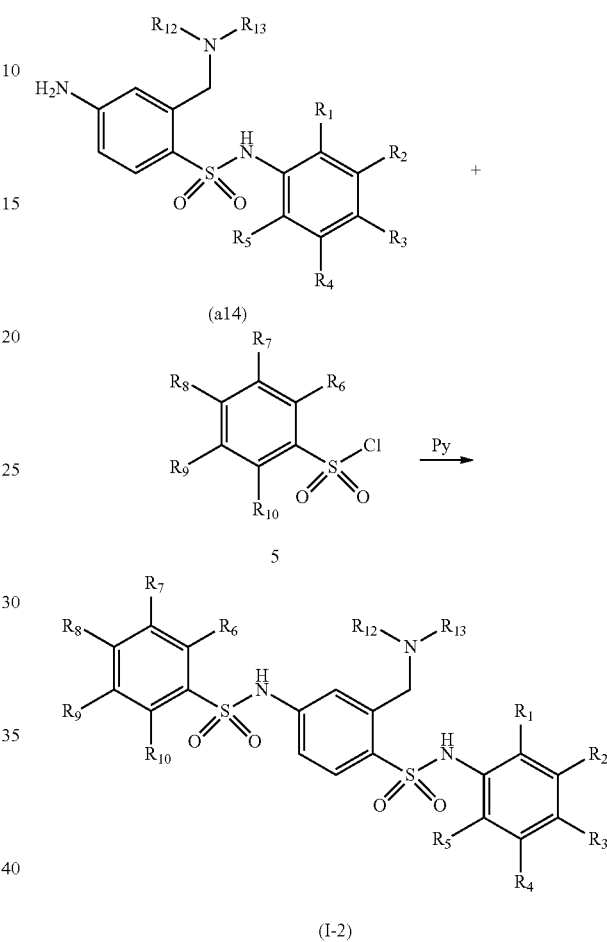

After the Compound a14 is dissolved with pyridine at room temperature, 1.5 times equivalent of the Compound 5 is added. After stirring for 4 hours at room temperature, the reaction system is moved to an ice bath, 2 mol/L dilute hydrochloric acid is slowly dropped to adjust the pH value to 3. After separating out solids, suction filtration is performed, and the obtained solids is dissolved with ethyl acetate. Column chromatography is then performed to obtain the compound of formula (I-2).

Step 5-2

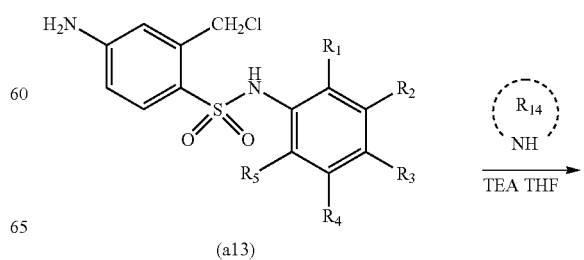

-continued

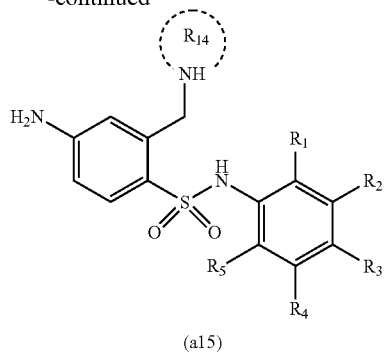

(a15)

At room temperature, the Compound a13 in the reaction flask is dissolved in tetrahydrofuran, then 1.5 times equivalent of aliphatic ring containing secondary amine and its various substitutes are added. And then 2 times equivalent of triethylamine is added. The reaction is heated to 60° C. to react for 10 hours. After the reaction is completed, the reaction system is moved to room temperature, then water is added to extract with ethyl acetate for 3 times; the organic phase is combined and washed with saturated salt water for 3 times, and Compound 15 is obtained by column chromatography.

Step 6-2

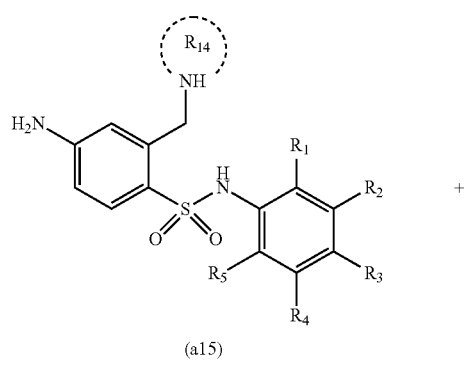

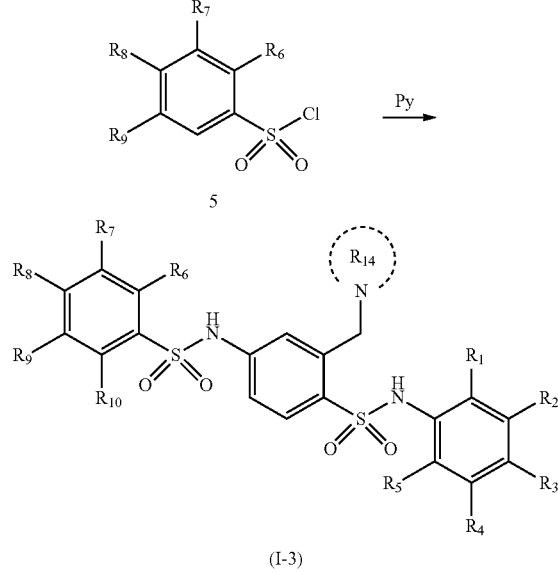

After the Compound a15 is dissolved with pyridine at room temperature, 1.5 times equivalent of the Compound 5 is added. After stirring for 2 hours at room temperature, the reaction system is moved to an ice bath. 2 mol/L dilute hydrochloric acid is slowly dropped to adjust the pH value to 3. After separating out solids, suction filtration is performed, and the obtained solids is dissolved with ethyl acetate. Column chromatography is then performed to obtain the compound of formula (I-3).

Example 6. Specific Structure of Compound of Formula (I-2) and (I-3)

Specific structures of compounds of formula (I-2) and (I-3) are described below in table form. The compound or the pharmacologically acceptable salt thereof for SIRT6 small-molecular aromatic activator of the present invention has any one of the structures listed in Table 2 below.

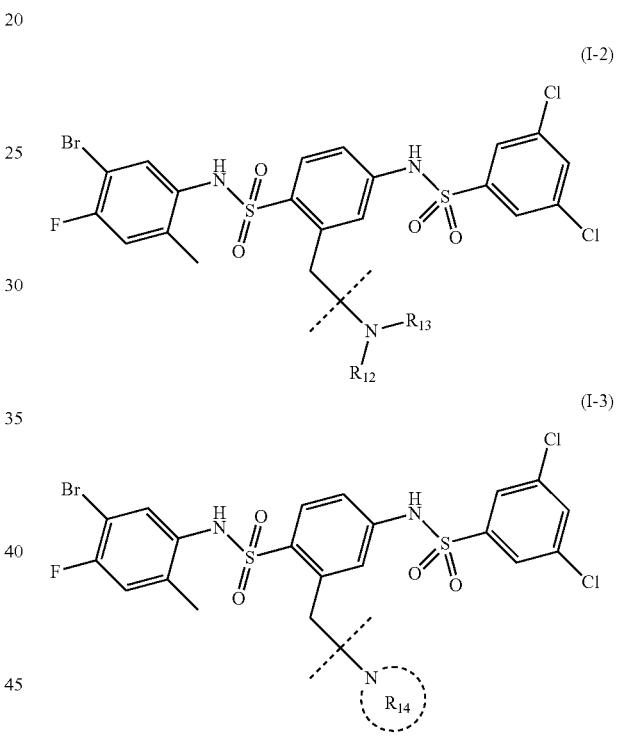

TABLE 2

| Specific structure of compound (I-2) and (I-3) | |
|---|---|
| Serial No. | Structure |
| SOL001 | |
| SOL002 | |
| SOL003 | |

TABLE 2-continued

Specific structure of compound (I-2) and (I-3)

| Serial No. | Structure |
|---|---|
| SOL004 | piperazine with N-methyl |
| SOL005 | piperidine |
| SOL006 | piperazine with N-Boc |
| SOL007 | piperazine with NH |
| SOL008 | N,N-dimethyl |
| SOL009 | N-methyl, N-ethyl |
| SOL010 | (S)-3-hydroxypyrrolidine |
| SOL011 | (R)-3-methylmorpholine |
| SOL012 | (S)-3-methylmorpholine |
| SOL013 | N,N-diethyl |
| SOL014 | 4-(dimethylamino)piperidine |
| SOL015 | N-isopropyl, N-ethyl |
| SOL016 | N,N-dipropyl |
| SOL017 | N,N-diisopropyl |
| SOL018 | N-propyl, N-ethyl |
| SOL019 | N-benzylpiperazine |
| SOL020 | N-methyl, N-propyl |
| SOL021 | N-ethynylpiperazine |
| SOL022 | piperazinyl-triazole-methyl acetate |
| SOL023 | piperazinyl-triazole-acetic acid |
| SOL024 | (R)-3-methylpiperazine-N-Boc |
| SOL025 | (S)-3-methylpiperazine-N-Boc |
| SOL026 | azetidine |
| SOL027 | N-(2-ethoxyethyl)piperazine |

TABLE 2-continued
Specific structure of compound (I-2) and (I-3)
| Serial No. | Structure |
|---|---|
| SOL028 | 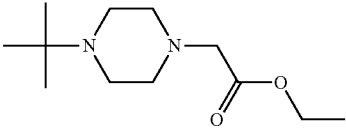 |
| SOL029 | 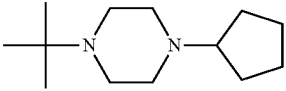 |
| SOL030 | 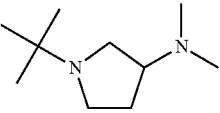 |
| SOL031 | 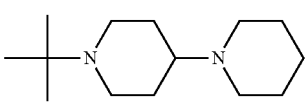 [SMILES: CC(C)(C)N1CCC(N2CCCCC2)CC1] |
| SOL032 | 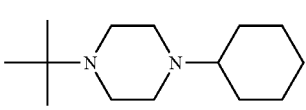 |
| SOL033 | 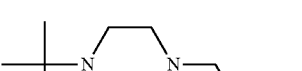 |
| SOL034 | 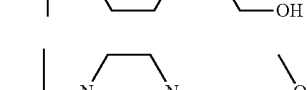 |
| SOL035 | 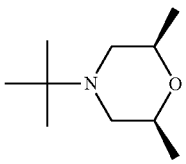 |
| SOL036 | 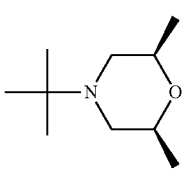 |
| SOL037 | 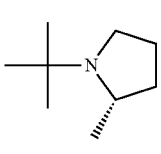 |
| SOL038 | 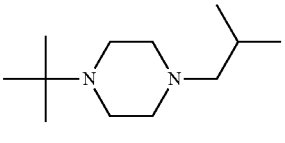 |
| SOL039 | 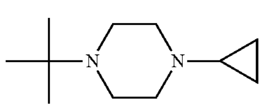 |
| SOL040 | 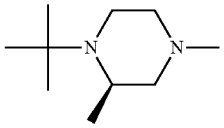 |
| SOL041 | 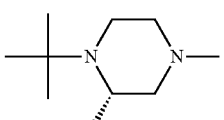 |
| SOL042 | 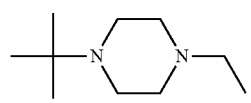 |
| SOL043 | 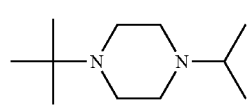 |
| SOL044 | 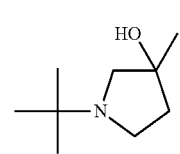 |
| SOL045 | 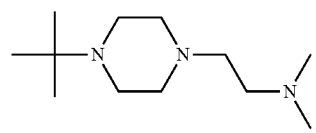 |
| SOL046 | 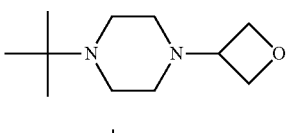 |
| SOL047 | 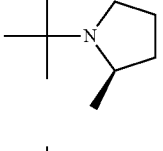 |
| SOL048 | 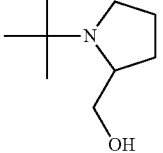 |
| SOL049 | 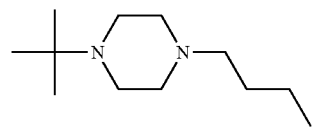 |
| SOL050 | 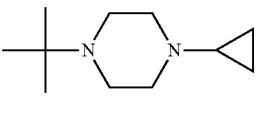 |

TABLE 2-continued

Specific structure of compound (I-2) and (I-3)

| Serial No. | Structure |
|---|---|
| SOL051 | (piperazine with t-Bu and phenyl) |
| SOL052 | (piperazine with t-Bu and propanol) |
| SOL053 | (pyrrolidine with t-Bu and CH2OH) |
| SOL054 | (2-methylpiperazine with t-Bu and N-methyl) |
| SOL055 | (azepane with t-Bu) |
| SOL056 | (azocane with t-Bu) |
| SOL057 | (pyrrolidine with t-Bu) |
| SOL058 | (piperazine with t-Bu and methyl, wedge bond) |
| SOL059 | (piperazine with t-Bu and methyl, dashed wedge) |
| SOL060 | (N,N-substituted with t-Bu) |
| SOL061 | (2-hydroxymethyl piperidine with t-Bu) |
| SOL062 | (2-carboxyl piperidine with t-Bu) |
| SOL063 | (N-methyl piperidine-2-carboxylate methyl ester) |
| SOL064 | (N-methyl piperidine-2-carboxylate methyl ester) |
| SOL065 | (N-methyl piperidine-2-carboxylic acid) |
| SOL066 | (2-hydroxymethyl piperidine with t-Bu) |

Example 7. Specific Compounds and Verification Data for SIRT6 Small-Molecule Allosteric Activator In the present embodiment, the specific compounds and their verification data for SIRT6 small-molecular electronic activator according to the present invention are listed in detail. It can be understood that all the following examples of compounds are the specific structures of compounds of formula (I). The compound of formula (I) has any structure of all the following compound examples.

Compound Example 1

2-Chloro-nitrogen-(4-(nitrogen-(3-chloro-2-methylphenyl) sulfamoyl) phenyl) benzenesulfonamide $^1$H NMR (400 MHz, DMSO-d6) δ11.27 (s, 1H), 9.68 (s, 1H), 8.12-8.10 (m, 1H), 7.70-7.64 (m, 2H), 7.58-7.54 (m, 1H), 7.47-7.45 (d, J=8 Hz, 2H), 7.30-7.21 (m, 3H), 7.09-7.05 (m, 1H), 6.81-6.79 (d, J=8.0 Hz, 1H), 1.78 (s, 3H) LCMS (ESI) m/z: 471.0 (M+H)$^+$

Compound Example 2

2-Bromo-nitrogen-(4-(nitrogen-(3-chloro-2-methylphenyl) sulfamoyl) phenyl) benzenesulfonamide $^1$H NMR (400 MHz, DMSO-d6) δ11.29 (s, 1H), 9.68 (s, 1H), 8.15-8.13 (m, 1H), 7.85-7.83 (m, 2H), 7.61-7.45 (m, 4H), 7.30-7.20 (m, 3H), 7.09-7.05 (m, 1H), 6.82-6.80 (d, J=8.0 Hz, 1H), 1.79 (s, 3H) LCMS (ESI) m/z: 514.9 (M+H)$^+$

Compound Example 3

2-Fluoro-nitrogen-(4-(nitrogen-(3-chloro-2-methylphenyl) sulfamoyl) phenyl) benzenesulfonamide $^1$H NMR (400 MHz, DMSO-d6) δ11.28 (s, 1H), 9.71 (s, 1H), 7.92 (s, 1H), 7.74 (m, 2H), 7.48-7.08 (m, 9H), 6.82 (m, 1H), 1.82 (s, 3H) LCMS (ESI) m/z: 455.0 (M+H)$^+$.

Compound Example 4

2-nitro-nitrogen-(4-(nitrogen-(3-chloro-2-methylphenyl) sulfamoyl) phenyl) benzenesulfonamide $^1$H NMR (400 MHz, DMSO-d6) δ10.85 (s, 1H), 9.67 (s, 1H), 7.57-7.47 (m, 3H), 7.28-7.07 (m, 5H), 6.78-6.58 (m, 3H), 7.30-7.26 (m, 3H), 7.10-7.06 (m, 1H), 6.83-6.81 (d, J=8.0 Hz, 1H), 1.87 (s, 3H) LCMS (ESI) m/z: 482.0 (M+H)$^+$.

Compound Example 5

2-Amino-nitrogen-(4-(nitrogen-(3-chloro-2-methylphenyl) sulfamoyl) phenyl) benzenesulfonamide $^1$H NMR (400 MHz, DMSO-d6) δ10.85 (s, 1H), 9.57 (s, 1H), 7.57-7.47 (m, 3H), 7.28-7.07 (m, 5H), 6.78-6.58 (m, 3H), 6.06 (s, 1H), 1.88 (s, 3H) LCMS (ESI) m/z: 452.0 (M+H)$^+$.

Compound Example 6

3-Bromo-nitrogen-(4-(nitrogen-(3-chloro-2-methylphenyl) sulfamoyl) phenyl) benzenesulfonamide $^1$H NMR (400 MHz, DMSO-d6) δ11.03 (s, 1H), 9.73 (s, 1H), 7.95-7.94 (t, 1H), 7.91-7.88 (m, 1H), 7.81-7.79 (m, 1H), 7.57-7.49 (m, 3H), 7.30-7.25 (m, 3H), 7.11-7.07 (t, 1H), 6.84-6.82 (d, J=8.0 Hz, 1H), 1.81 (s, 3H) LCMS (ESI) m/z: 514.9 (M+H)$^+$.

Compound Example 7

3-Trifluoromethyl-nitrogen-(4-(nitrogen-(3-chloro-2-methylphenyl) sulfamoyl) phenyl) benzenesulfonamide $^1$H NMR (400 MHz, DMSO-d6) δ11.10 (s, 1H), 9.73 (s, 1H), 8.10-8.08 (m, 3H), 7.87-7.83 (t, 1H), 7.51-7.48 (d, J=12 Hz, 2H), 7.29-7.26 (m, 3H), 7.08-7.04 (t, 1H), 6.84-6.82 (d, J=8.0 Hz, 1H), 1.77 (s, 3H) LCMS (ESI) m/z: 505.0 (M+H)$^+$.

Compound Example 8

3-Fluoro-nitrogen-(4-(nitrogen-(3-chloro-2-methylphenyl) sulfamoyl) phenyl) benzenesulfonamide $^1$H NMR (400 MHz, DMSO-d6) δ11.03 (s, 1H), 9.73 (s, 1H), 7.67-7.53 (m, 4H), 7.51-7.48 (d, J=12 Hz, 2H), 7.30-7.25 (m, 3H), 7.10-7.06 (t, 1H), 6.84-6.82 (d, J=8.0 Hz, 1H), 1.81 (s, 3H) LCMS (ESI) m/z: 455.0 (M+H)$^+$.

Compound Example 9

3-Chloro-nitrogen-(4-(nitrogen-(3-chloro-2-methylphenyl) sulfamoyl) phenyl) benzenesulfonamide $^1$H NMR (400 MHz, DMSO-d6) δ11.03 (s, 1H), 9.73 (s, 1H), 7.82-7.81 (m, 1H), 7.78-7.75 (m, 2H), 7.65-7.61 (t, 1H), 7.51-7.49 (d, J=8 Hz, 2H), 7.30-7.25 (m, 3H), 7.10-7.06 (t, 1H), 6.84-6.82 (d, J=8.0 Hz, 1H), 1.81 (s, 3H) LCMS (ESI) m/z: 471.0 (M+H)$^+$.

Compound Example 10

3-nitro-nitrogen-(4-(nitrogen-(3-chloro-2-methylphenyl) sulfamoyl) phenyl) benzenesulfonamide 1H NMR (400 MHz, DMSO-d6) δ11.21 (s, 1H), 9.74 (s, 1H), 8.56-8.50 (m, 2H), 8.23-8.21 (d, J=8.0 Hz, 2H), 7.92-7.88 (t, 1H), 7.51-7.49 (d, J=8 Hz, 2H), 7.29-7.28 (m, 3H), 7.10-7.06 (t, 1H), 6.86-6.84 (d, J=8.0 Hz, 1H), 1.76 (s, 3H) LCMS (ESI) m/z: 482.0 (M+H)$^+$.

Compound Example 11

3-methoxy-nitrogen-(4-(nitrogen-(3-chloro-2-methylphenyl) sulfamoyl) phenyl) benzenesulfonamide $^1$H NMR (400 MHz, DMSO-d6) δ10.91 (s, 1H), 9.71 (s, 1H), 7.51-7.47 (m, 3H), 7.38-7.36 (d, J=8.0 Hz, 2H), 7.65-7.61 (t, 1H), 7.51-7.49 (d, J=8.0 Hz, 2H), 7.38-7.21 (m, 5H), 7.09-7.05 (t, 1H), 6.83-6.81 (d, J=8.0 Hz, 1H), 3.79 (s, 3H), 1.84 (s, 3H) LCMS (ESI) m/z: 467.0 (M+H)$^+$.

Compound Example 12

3-Cyano-nitrogen-(4-(nitrogen-(3-chloro-2-methylphenyl) sulfamoyl) phenyl) benzenesulfonamide $^1$H NMR (400 MHz, DMSO-d6) δ11.13 (s, 1H), 9.73 (s, 1H), 8.27 (s, 1H), 8.19-8.17 (d, J=8.0 Hz, 1H), 8.11-8.09 (d, J=8.0 Hz, 1H), 7.84-7.80 (t, 1H), 7.50-7.48 (d, J=8.0 Hz, 2H), 7.30-7.25 (m, 3H), 7.11-7.07 (t, 1H), 6.85-6.83 (d, J=8.0 Hz, 1H), 1.78 (s, 3H) LCMS (ESI) m/z: 462.0 (M+H)$^+$.

Compound Example 13

3-Amino-nitrogen-(4-(nitrogen-(3-chloro-2-methylphenyl) sulfamoyl) phenyl) benzenesulfonamide $^1$H NMR (400 MHz, DMSO-d6) δ10.73 (s, 1H), 9.75 (s, 1H), 7.50-7.48 (d, J=8.0 Hz, 2H), 7.30-7.06 (m, 5H), 7.01 (s, 1H), 6.88-6.86 (d, J=8.0 Hz, 1H), 6.80-6.74 (m, 2H), 5.66 (s, 2H), 1.93 (s, 3H) LCMS (ESI) m/z: 452.1 (M+H)$^+$.

Compound Example 14

4-Fluoro-nitrogen-(4-(nitrogen-(3-chloro-2-methylphenyl) sulfamoyl) phenyl) benzenesulfonamide $^1$H NMR (400 MHz, DMSO-d6) δ10.96 (s, 1H), 9.72 (s, 1H), 7.90-7.86 (m, 2H), 7.49-7.41 (m, 4H), 7.30-7.23 (m, 3H), 7.11-7.07 (t, 1H), 6.86-6.84 (d, J=8.0 Hz, 1H), 1.79 (s, 3H) LCMS (ESI) m/z: 455.01 (M+H)⁺.

Compound Example 15

4-Chloro-nitrogen-(4-(nitrogen-(3-chloro-2-methylphenyl) sulfamoyl) phenyl) benzenesulfonamide ¹H NMR (400 MHz, DMSO-d6) δ10.98 (s, 1H), 9.73 (s, 1H), 7.90-7.86 (m, 2H), 7.49-7.42 (m, 4H), 7.31-7.24 (m, 3H), 7.10-7.06 (t, 1H), 6.86-6.84 (d, J=8.0 Hz, 1H), 1.81 (s, 3H) LCMS (ESI) m/z: 471.0 (M+H)⁺.

Compound Example 16

4-Bromo-nitrogen-(4-(nitrogen-(3-chloro-2-methylphenyl) sulfamoyl) phenyl) benzenesulfonamide 1H NMR (400 MHz, DMSO-d6) δ11.02 (s, 1H), 9.73 (s, 1H), 7.80-7.74 (m, 4H), 7.50-7.48 (d, J=8.0 Hz, 2H), 7.27-7.25 (m, 3H), 7.09-7.08 (t, 1H), 6.88-6.86 (d, J=8.0 Hz, 1H), 1.80 (s, 3H) LCMS (ESI) m/z: 514.9 (M+H)⁺.

Compound Example 17

4-methoxy-nitrogen-(4-(nitrogen-(3-chloro-2-methylphenyl) sulfamoyl) phenyl) benzenesulfonamide ¹H NMR (400 MHz, DMSO-d6) δ10.79 (s, 1H), 9.70 (s, 1H), 7.76-7.74 (d, J=8.0 Hz, 2H), 7.49-7.47 (d, J=8.0 Hz, 2H), 7.30-7.23 (m, 3H), 7.10-7.08 (t, 3H), 6.85-6.83 (d, J=8.0 Hz, 1H), 3.81 (s, 3H), 1.83 (s, 3H) LCMS (ESI) m/z: 467.0 (M+H)⁺.

Compound Example 18

4-Trifluoromethyl-nitrogen-(4-(nitrogen-(3-chloro-2-methylphenyl) sulfamoyl) phenyl) benzenesulfonamide ¹H NMR (400 MHz, DMSO-d6) δ11.21 (s, 1H), 9.78 (s, 1H), 8.22-8.10 (m, 6H), 7.56-6.62 (m, 8H), 1.77 (s, 3H) LCMS (ESI) m/z: 505.0 (M+H)⁺.

Compound Example 19

4-Trifluoromethoxy-nitrogen-(4-(nitrogen-(3-chloro-2-methylphenyl) sulfamoyl) phenyl) benzenesulfonamide ¹H NMR (400 MHz, DMSO-d6) δ11.20 (s, 1H), 9.76 (s, 1H), 8.10-8.00 (m, 6H), 7.53-6.89 (m, 8H), 1.76 (s, 3H) LCMS (ESI) m/z: 521.0 (M+H)⁺.

Compound Example 20

4-Cyano-nitrogen-(4-(nitrogen-(3-chloro-2-methylphenyl) sulfamoyl) phenyl) benzenesulfonamide ¹H NMR (400 MHz, DMSO-d6) δ10.87 (s, 1H), 9.73 (s, 1H), 7.79-7.77 (d, J=8.0 Hz, 2H), 7.52-7.50 (d, J=8.0 Hz, 2H), 7.30-7.23 (m, 3H), 7.10-7.08 (t, 3H), 6.85-6.83 (d, J=8.0 Hz, 1H), 1.79 (s, 3H) LCMS (ESI) m/z: 462.0 (M+H)⁺.

Compound Example 21

2,3-Dichloro-nitrogen-(4-(nitrogen-(3-chloro-2-methylphenyl) sulfamoyl) phenyl) benzenesulfonamide 1H NMR (400 MHz, DMSO-d6) δ11.44 (s, 1H), 9.70 (s, 1H), 7.60-7.56 (m, 1H), 7.48-7.46 (d, J=8.0 Hz, 2H), 7.29-7.22 (m, 3H), 7.10-7.06 (t, 1H), 6.84-6.82 (d, J=8.0 Hz, 1H), 1.74 (s, 3H) LCMS (ESI) m/z: 506.9 (M+H)⁺.

Compound Example 22

2,4-Dichloro-nitrogen-(4-(nitrogen-(3-chloro-2-methylphenyl) sulfamoyl) phenyl) benzenesulfonamide ¹H NMR (400 MHz, DMSO-d6) δ11.37 (s, 1H), 9.70 (s, 1H), 8.11-8.09 (d, J=8.0 Hz, 1H), 7.88-7.87 (d, J=4.0 Hz, 1H), 7.48-7.46 (d, J=8.0 Hz, 2H), 7.30-7.21 (m, 3H), 7.10-7.06 (t, 1H), 6.85-6.83 (d, J=8.0 Hz, 1H), 1.73 (s, 3H) LCMS (ESI) m/z: 506.9 (M+H)⁺.

Compound Example 23

2-chloro-4-fluoro-nitrogen-(4-(nitrogen-(3-chloro-2-methylphenyl) sulfamoyl) phenyl) benzenesulfonamide ¹H NMR (400 MHz, DMSO-d6) δ11.32 (s, 1H), 9.70 (s, 1H), 8.20-8.16 (m, 1H), 7.75-7.72 (m, 1H), 7.47-7.42 (m, 3H), 7.30-7.28 (d, J=8.0 Hz, 2H), 7.23-7.20 (d, J=12.0 Hz, 2H), 7.11-7.07 (t, 1H), 6.85-6.83 (d, J=8.0 Hz, 1H), 1.74 (s, 3H) LCMS (ESI) m/z: 489.0 (M+H)⁺.

Compound Example 24

3,6-Dichloro-nitrogen-(4-(nitrogen-(3-chloro-2-methylphenyl) sulfamoyl) phenyl) benzenesulfonamide ¹H NMR (400 MHz, DMSO-d6) δ11.42 (s, 1H), 8.07 (s, 1H), 7.80-7.69 (m, 2H), 7.50-7.48 (d, J=8.0 Hz, 2H), 7.30-7.24 (m, 3H), 7.10-7.06 (t, 1H), 6.84-6.82 (d, J=8.0 Hz, 1H), 1.77 (s, 3H) LCMS (ESI) m/z: 506.9 (M+H)⁺.

Compound Example 25

2,6-Dichloro-nitrogen-(4-(nitrogen-(3-chloro-2-methylphenyl) sulfamoyl) phenyl) benzenesulfonamide ¹H NMR (400 MHz, DMSO-d6) δ11.47 (s, 1H), 9.70 (s, 1H), 7.67-7.57 (m, 3H), 7.51-7.49 (d, J=8.0 Hz, 2H), 7.30-7.21 (m, 3H), 7.10-7.06 (t, 1H), 6.82-6.80 (d, J=8.0 Hz, 1H), 1.79 (s, 3H) LCMS (ESI) m/z: 506.9 (M+H)⁺.

Compound Example 26

2,4-Dimethoxy-nitrogen-(4-(nitrogen-(3-chloro-2-methylphenyl) sulfamoyl) phenyl) benzenesulfonamide ¹H NMR (400 MHz, DMSO-d6) δ10.56 (s, 1H), 9.64 (s, 1H), 7.77-7.75 (d, J=8.0 Hz, 2H), 7.43-7.41 (d, J=8.0 Hz, 2H), 7.29-7.27 (d, J=8.0 Hz, 1H), 7.19-7.17 (d, J=8.0 Hz, 1H), 7.09-7.05 (t, 1H), 6.65-6.61 (m, 2H), 3.82-3.81 (d, J 4.0 Hz, 6H), 1.78 (s, 3H) LCMS (ESI) m/z: 497.0 (M+H)+.

Compound Example 27

3-trifluoromethyl-4-chloro-nitrogen-(4-(nitrogen-(3-chloro-2-methylphenyl) sulfamoyl) phenyl) benzenesulfonamide ¹H NMR (400 MHz, DMSO-d6) δ11.15 (s, 1H), 9.75 (s, 1H), 8.18 (s, 1H), 8.09-8.07 (d, J=8.0 Hz, 1H), 7.99-7.97 (d, J=8.0 Hz, 1H), 7.51-7.49 (d, J=8.0 Hz, 2H), 7.29-7.27 (m, 3H), 7.10-7.06 (t, 1H), 6.89-6.87 (d, J=8.0 Hz, 1H), 1.72 (s, 3H) LCMS (ESI) m/z: 539.0 (M+H)+.

Compound Example 28

4-methoxy-3-chloro-nitrogen-(4-(nitrogen-(3-chloro-2-methylphenyl) sulfamoyl) phenyl) benzenesulfonamide ¹H NMR (400 MHz, DMSO-d6) δ10.88 (s, 1H), 9.73 (s, 1H), 7.82-7.74 (m, 2H), 7.51-7.49 (d, J=8.0 Hz, 2H), 7.32-7.25 (m, 4H), 7.10-7.06 (t, 1H), 6.87-6.85 (d, J=8.0 Hz, 1H), 3.92 (s, 3H), 1.72 (s, 3H) LCMS (ESI) m/z: 501.0 (M+H)+.

Compound Example 29

3,5-Dichloro-nitrogen-(4-(nitrogen-(3-chloro-2-methylphenyl) sulfamoyl) phenyl) benzenesulfonamide ¹H NMR (400 MHz, DMSO-d6) δ11.11 (s, 1H), 9.76 (s, 1H), 7.99 (s, 1H), 7.79 (s, 2H), 7.53-7.51 (d, J=8.0 Hz, 2H), 7.30-7.28 (m, 3H), 7.11-7.07 (t, 1H), 6.88-6.86 (d, J=8.0 Hz, 1H), 1.79 (s, 3H). LCMS (ESI) m/z: 506.9 (M+H)+.

Compound Example 30

4-Bromo-3-fluoro-nitrogen-(4-(nitrogen-(3-chloro-2-methylphenyl) sulfamoyl) phenyl) benzenesulfonamide ¹H NMR (400 MHz, DMSO-d6) δ11.09 (s, 1H), 9.74 (s, 1H), 8.00-7.96 (t, 1H), 7.78-7.76 (m, 1H), 7.58-7.48 (m, 3H), 7.30-7.26 (t, 3H), 7.11-7.07 (t, 1H), 6.88-6.86 (d, J=8.0 Hz, 1H), 1.74 (s, 3H). LCMS (ESI) m/z: 532.9 (M+H)+.

Compound Example 31

3,4-Dimethoxy-nitrogen-(4-(nitrogen-(3-chloro-2-methylphenyl) sulfamoyl) phenyl) benzenesulfonamide ¹H NMR (400 MHz, DMSO-d6) δ10.74 (s, 1H), 9.69 (s, 1H), 7.49-7.47 (d, J=8.0 Hz, 2H), 7.40-7.37 (m, 1H), 7.32-7.25 (m, 4H), 7.09-7.07 (m, 2H), 6.83-6.81 (d, J=8.0 Hz, 1H), 3.80-3.78 (d, J=4.0 Hz, 6H), 1.82 (s, 3H) LCMS (ESI) m/z: 497.0 (M+H)+.

Compound Example 32

3-Chloro-4-methoxy-nitrogen-(4-(nitrogen-(3-(trifluoromethyl) phenyl) sulfamoyl) phenyl) benzenesulfonamide ¹H NMR (400 MHz, DMSO-d6) δ10.45 (s, 1H), 9.79 (s, 1H), 7.58-7.56 (d, J=8.0 Hz, 2H), 7.35-7.13 (m, 10H), 6.94-6.92 (d, J=8.0 Hz, 1H), 4.61 (s, 3H), 2.08 (s, 3H) LCMS (ESI) m/z: 521.0 (M+H)+.

Compound Example 33

Nitrogen-(4-(Nitrogen-(3-trifluoromethylphenyl) sulfamoyl) phenyl)-3-bromo-4-methoxybenzenesulfonamide ¹H NMR (400 MHz, DMSO-d6) δ11.26 (s, 1H), 9.75 (s, 1H), 8.42-8.40 (d, J=8.0 Hz, 2H), 8.07-8.05 (d, J=8.0 Hz, 2H), 7.51-7.49 (d, J=8.0 Hz, 2H), 7.28-7.26 (d, J=8.0 Hz, 2H), 7.12-7.08 (t, 1H), 6.89-6.87 (d, J=8.0 Hz, 1H), 1.75 (s, 3H). LCMS (ESI) m/z: 565.0 (M+H)+.

Compound Example 34

Nitrogen-(4-(Nitrogen-(3-fluorophenyl) sulfamoyl) phenyl)-3-bromo-4-methoxybenzenesulfonamide ¹H NMR (400 MHz, DMSO-d6) δ10.86 (s, 1H), 10.17 (s, 1H), 7.63-7.59 (m, 4H), 7.32-7.28 (t, 1H), 7.22-7.17 (m, 4H), 7.02-6.99 (m, 3H), 3.89 (s, 3H). LCMS (ESI) m/z: 514.9 (M+H)+.

Compound Example 35

Nitrogen-(4-(Nitrogen-(3-methoxyphenyl) sulfamoyl) phenyl)-3-bromo-4-methoxybenzenesulfonamide ¹H NMR (400 MHz, DMSO-d6) δ10.82 (s, 1H), 9.32 (s, 1H), 7.64-7.59 (m, 2H), 7.48-7.46 (d, J=8.0 Hz, 2H), 7.38-7.34 (t, 1H), 7.24-7.21 (d, J=12.0 Hz, 2H), 6.85-6.81 (m, 2H), 6.72-6.70 (d, J=8.0 Hz, 2H), 3.91 (s, 3H), 2.19 (s, 3H), 1.75 (s, 3H). LCMS (ESI) m/z: 528.0 (M+H)+

Compound Example 36

3,5-Dichloro-nitrogen-(4-(nitrogen-(2-methylphenyl) sulfamoyl) phenyl) benzenesulfonamide ¹H NMR (400 MHz, DMSO-d6) δ10.90 (s, 1H), 10.34 (s, 1H), 7.64-7.60 (m, 2H), 7.33-7.22 (m, 5H), 7.04-7.02 (d, J=8.0 Hz, 2H), 3.89 (s, 3H). LCMS (ESI) m/z: 471.0 (M+H)+.

Compound Example 37

3,5-Dichloro-nitrogen-(4-(nitrogen-(3-methylphenyl) sulfamoyl) phenyl) benzenesulfonamide ¹H NMR (400 MHz, DMSO-d6) δ10.88 (s, 1H), 10.34 (s, 1H), 7.93 (s, 1H), 7.79-7.76d, J=12.0 Hz, 1H), 7.64-7.62 (d, J=8.0 Hz, 2H), 7.28-7.22 (m, 5H), 7.04-7.02 (d, J=8.0 Hz, 2H), 3.91 (s, 3H). LCMS (ESI) m/z: 471.0 (M+H)+.

Compound Example 38

3,5-Dichloro-nitrogen-(4-(nitrogen-(2-chlorophenyl) sulfamoyl) phenyl) benzenesulfonamide ¹H NMR (400 MHz, DMSO-d6) δ8.53-8.50 (d, J=12.0 Hz, 2H), 8.21-8.19 (d, J=8.0 Hz, 2H), 8.01-7.99 (d, J=8.0 Hz, 1H), 7.82-7.77 (m, 3H), 7.48-7.38 (m, 3H), 4.02 (s, 3H). LCMS (ESI) m/z: 492.9 (M+H)+.

Compound Example 39

3,5-Dichloro-nitrogen-(4-(nitrogen-(3-chlorophenyl)sulfamoyl) phenyl) benzenesulfonamide $^1$H NMR (400 MHz, DMSO-d6) δ10.82 (s, 1H), 9.32 (s, 1H), 7.95-7.94 (d, J=4.0 Hz, 1H), 7.81-7.79 (m, 1H), 7.49-7.46 (d, J=12.0 Hz, 2H), 7.29-7.22 (m, 3H), 6.85-6.81 (m, 2H), 6.72-6.70 (d, J=8.0 Hz, 1H), 3.93 (s, 3H), 2.19 (s, 3H), 1.73 (s, 3H). LCMS (ESI) m/z: 492.9 (M+H)$^+$.

Compound Example 40

3,5-Dichloro-nitrogen-(4-(nitrogen-(4-chlorophenyl)sulfamoyl) phenyl) benzenesulfonamide $^1$H NMR (400 MHz, DMSO-d6) δ10.86 (s, 1H), 10.11 (s, 1H), 7.94 (s, 1H), 7.79-7.77 (m, 1H), 7.64-7.62 (d, J=8.0 Hz, 2H), 7.24-7.21 (m, 3H), 7.08-7.04 (t, 2H), 6.83-6.81 (m, 3H), 3.90 (s, 3H), 2.16 (s, 3H). LCMS (ESI) m/z: 492.9 (M+H)$^+$.

Compound Example 41

3,5-Dichloro-nitrogen-(4-(nitrogen-(2-bromophenyl)sulfamoyl)enyl) benzenesulfonamide $^1$H NMR (400 MHz, DMSO-d6) δ10.87 (s, 1H), 10.51 (s, 1H), 7.93 (s, 1H), 7.78-7.76 (m, 1H), 7.69-7.67 (d, J=8.0 Hz, 2H), 7.26-7.21 (m, 4H), 6.86-6.82 (m, 3H), 3.90 (s, 3H). LCMS (ESI) m/z: 534.8 (M+H)$^+$.

Compound Example 42

3,5-Dichloro-nitrogen-(4-(nitrogen-(3-methylphenyl)sulfamoyl) phenyl) benzenesulfonamide $^1$H NMR (400 MHz, DMSO-d6) δ 11.06 (s, 1H), 9.48 (s, 1H), 8.03-8.02 (m, 1H), 7.78-7.77 (d, J=4.0 Hz, 1H), 7.53-7.51 (d, J=8.0 Hz, 2H), 7.27-7.25 (d, J=8.0 Hz, 2H), 7.09-7.06 (m, 3H), 6.92-6.90 (m, 1H), 1.77 (s, 3H). LCMS (ESI) m/z: 534.8 (M+H)$^+$.

Compound Example 43

3,5-Dichloro-nitrogen-(4-(nitrogen-(2-chlorophenyl)sulfamoyl) phenyl) benzenesulfonamide $^1$H NMR (400 MHz, DMSO-d6) δ11.06 (s, 1H), 9.48 (s, 1H), 8.03-8.02 (m, 1H), 7.78-7.77 (d, J=4.0 Hz, 1H), 7.53-7.51 (d, J=8.0 Hz, 2H), 7.27-7.25 (d, J=8.0 Hz, 2H), 7.09-7.06 (m, 3H), 6.92-6.90 (m, 1H), 1.77 (s, 3H). LCMS (ESI) m/z: 487.0 (M+H)$^+$.

Compound Example 44

3,5-Dichloro-nitrogen-(4-(nitrogen-(3-tifluoromethoxyphenyl) sulfamoyl) phenyl) benzenesulfonamide $^1$H NMR (400 MHz, DMSO-d6) δ11.15 (s, 1H), 10.50 (s, 1H), 7.94-7.69 (m, 5H), 7.30-7.06 (m, 6H), LCMS (ESI) m/z: 541.0 (M+H)$^+$.

Compound Example 45

3,5-Dichloro-nitrogen-(4-(nitrogen-(4-bromophenyl)sulfamoyl) phenyl) benzenesulfonamide 1H NMR (400 MHz, DMSO-d6) δ11.11 (s, 1H), 10.38 (s, 1H), 7.94-7.93 (m, 1H), 7.75-7.74 (d, J=4.0 Hz, 2H), 7.68-7.66 (d, J=8.0 Hz, 2H), 7.39-7.37 (d, J=8.0 Hz, 2H), 7.28-7.26 (d, J=8.0 Hz, 2H), 6.99-6.97 (d, J=8.0 Hz, 2H) LCMS (ESI) m/z: 534.9 (M+H)$^+$.

Compound Example 46

3,5-Dichloro-nitrogen-(4-(nitrogen-(2-methoxyphenyl) sulfamoyl) phenyl) benzenesulfonamide $^1$H NMR (400 MHz, DMSO-d6) δ11.08 (s, 1H), 9.38 (s, 1H), 8.00-7.99 (t, 1H), 7.81-7.80 (d, J=4.0 Hz, 2H), 7.57-7.55 (d, J=8.0 Hz, 2H), 7.24-7.22 (d, J=8.0 Hz, 2H), 7.17-7.09 (m, 2H), 6.87-6.78 (d, J=8.0 Hz, 2H), 3.24 (s, 3H) LCMS (ESI) m/z: 487.0 (M+H)$^+$.

Compound Example 47

3,5-Dichloro-nitrogen-(4-(nitrogen-(3-trifluoromethoxyphenyl) sulfamoyl) phenyl) benzenesulfonamide $^1$H NMR (400 MHz, DMSO-d6) δ11.16 (s, 1H), 10.62 (s, 1H), 7.89 (s, 1H), 7.75 (s, 2H), 7.72-7.69 (d, J=8.0 Hz, 2H), 7.40-7.27 (m, 3H), 7.05-7.03 (m, 2H), 6.98-6.96 (d, J=8.0 Hz, 2H), 3.67 (s, 3H) LCMS (ESI) m/z: 541.0 (M+H)$^+$

Compound Example 48

2-Bromo-4-trifluoromethyl-nitrogen-(4-(nitrogen-(3-chloro-2-methylphenyl) sulfamoyl) phenyl) benzenesulfonamide $^1$H NMR (400 MHz, DMSO-d6) δ11.53 (s, 1H), 9.71 (s, 1H), 8.31-8.30 (d, J=4.0 Hz, 1H), 8.12-8.10 (d, J=8.0 Hz, 1H), 7.98-7.96 (m, 1H), 7.50-7.48 (d, J=8.0 Hz, 1H), 7.28-7.24 (t, 3H), 7.08-7.04 (t, 1H), 6.85-6.83 (d, J=8.0 Hz, 1H), 1.75 (s, 3H) LCMS (ESI) m/z: 583.0 (M+H)$^+$.

Compound Example 49

3-chloro-5-bromo-nitrogen-(4-(nitrogen-(3-chloro-2-methylphenyl) sulfamoyl) phenyl) benzenesulfonamide $^1$H NMR (400 MHz, DMSO-d6) δ11.15 (s, 1H), 9.76 (s, 1H), 8.37 (s, 1H), 8.25 (s, 1H), 8.09 (s, 1H), 7.53-7.51 (d, J=8.0 Hz, 1H), 7.31-7.26 (t, 3H), 7.09-7.05 (t, 1H), 6.88-6.86 (d, J=8.0 Hz, 1H), 1.75 (s, 3H) LCMS (ESI) m/z: 549.0 (M+H)$^+$.

Compound Example 50

2,5-Dibromo-nitrogen-(4-(nitrogen-(3-chloro-2-methylphenyl) sulfamoyl) phenyl) benzenesulfonamide $^1$H NMR (400 MHz, DMSO-d6) δ11.42 (s, 1H), 9.71 (s, 1H), 8.19 (s, 1H), 7.79 (s, 2H), 7.51-7.49 (d, J=8.0 Hz, 1H), 7.30-7.24 (m, 3H), 7.10-7.06 (t, 1H), 6.84-6.82 (d, J=8.0 Hz, 1H), 1.79 (s, 3H) LCMS (ESI) m/z: 592.9 (M+H)+.

Compound Example 51

2,5-Difluoromethyl-nitrogen-(4-(nitrogen-(3-chloro-2-methylphenyl) sulfamoyl) phenyl) benzenesulfonamide $^1$H NMR (400 MHz, DMSO-d6) δ11.51 (s, 1H), 9.76 (s, 1H), 8.39-8.29 (m, 3H), 7.79 (s, 2H), 7.53-7.51 (d, J=8.0 Hz, 1H), 7.28-7.25 (m, 3H), 7.06-7.02 (t, 1H), 6.87-6.85 (d, J=8.0 Hz, 1H), 1.78 (s, 3H). LCMS (ESI) m/z: 572.9 (M+H)+.

Compound Example 52

3,5-Dibromo-nitrogen-(4-(nitrogen-(3-chloro-2-methylphenyl) sulfamoyl) phenyl) benzenesulfonamide $^1$H NMR (400 MHz, DMSO-d6) δ11.10 (s, 1H), 9.76 (s, 1H), 8.22 (s, 1H), 7.95-7.93 (d, J=8.0 Hz, 1H), 7.51-6.87 (m, 9H), 1.80 (s, 3H). LCMS (ESI) m/z: 592.9 (M+H)+.

Compound Example 53

3,5-Dichloro-nitrogen-(4-(nitrogen-phenylsulfamoyl) phenyl) benzenesulfonamide $^1$H NMR (400 MHz, DMSO-d6) δ11.09 (s, 1H), 10.19 (s, 1H), 7.95-7.94 (t, 1H), 7.75-7.74 (d, J=8.0 Hz, 2H), 7.67-6.65 (d, J=8.0 Hz, 2H), 7.26-7.24 (d, J=8.0 Hz, 2H), 7.21-7.17 (m, 2H), 7.03-6.99 (m, 3H). LCMS (ESI) m/z: 457.0 (M+H)+.

Compound Example 54

3,5-Dichloro-nitrogen-(4-(nitrogen-(3-fluorophenyl) sulfamoyl) phenyl) benzenesulfonamide $^1$H NMR (400 MHz, DMSO-d6) δ11.13 (s, 1H), 10.52 (s, 1H), 7.88 (s, 1H), 7.75-7.70 (m, 4H), 7.29-7.19 (m, 3H), 6.86-6.80 (m, 3H). LCMS (ESI) m/z: 475.0 (M+H)+.

Compound Example 55

3,5-Dichloro-nitrogen-(4-(nitrogen-(2-fluorophenyl) sulfamoyl) phenyl) benzenesulfonamide $^1$H NMR (400 MHz, DMSO-d6) δ11.10 (s, 1H), 10.07 (s, 1H), 7.98-7.97 (t, 1H), 7.77 (s, 2H), 7.63-7.60 (d, J=12.0 Hz, 2H), 7.28-7.26 (d, J=8.0 Hz, 2H), 7.20-7.15 (m, 2H), 7.10-7.06 (t, 2H). LCMS (ESI) m/z: 475.0 (M+H)+.

Compound Example 56

3,5-Dichloro-nitrogen-(4-(nitrogen-(2-trifluoromethylphenyl) sulfamoyl) phenyl) benzenesulfonamide $^1$H NMR (400 MHz, DMSO-d6) δ11.12 (s, 1H), 10.02 (s, 1H), 7.99-7.33 (m, 10H), 7.02 (s, 1H). LCMS (ESI) m/z: 525.0 (M+H)+.

Compound Example 57

3,5-Dichloro-nitrogen-(4-(nitrogen-(4-fluorophenyl) sulfamoyl) phenyl) benzenesulfonamide $^1$H NMR (400 MHz, DMSO-d6) δ11.10 (s, 1H), 10.16 (s, 1H), 7.90-7.89 (t, 1H), 7.75-7.74 (d, J=4.0 Hz, 2H), 7.64-7.62 (d, J=8.0 Hz, 2H), 7.28-7.26 (d, J=8.0 Hz, 2H), 7.04-7.02 (d, J=8.0 Hz, 4H). LCMS (ESI) m/z: 475.0 (M+H)+.

Compound Example 58

3,5-Dichloro-nitrogen-(4-(nitrogen-(2-methyl-3-chlorophenyl) sulfamoyl) phenyl) benzenesulfonamide $^1$H NMR (400 MHz, DMSO-d6) δ10.77 (s, 1H), 9.80 (s, 1H), 7.99-7.88 (m, 5H), 7.69-7.66 (d, J=12.0 Hz, 2H), 7.32-7.30 (d, J=8.0 Hz, 1H), 7.15-7.11 (t, 1H), 6.93-6.91 (t, 1H), 2.10 (s, 3H). LCMS (ESI) m/z: 469.0 (M+H)+.

Compound Example 59

3,5-Dichloro-nitrogen-(4-(nitrogen-(3-trifluoromethylphenyl) sulfamoyl) phenyl) benzenesulfonamide $^1$H NMR (400 MHz, DMSO-d6) δ11.15 (s, 1H), 10.68 (s, 1H), 7.84 (s, 1H), 7.74-7.70 (m, 4H), 7.45-7.41 (t, 1H), 7.34-7.29 (m, 5H). LCMS (ESI) m/z: 525.0 (M+H)+.

Compound Example 60

3,5-Dichloro-nitrogen-(4-(nitrogen-(2-bromo-4-fluorophenyl) sulfamoyl) phenyl) benzenesulfonamide $^1$H NMR (400 MHz, DMSO-d6) δ11.09 (s, 1H), 9.85 (s, 1H), 7.99 (s, 1H), 7.78 (s, 1H), 7.56-7.54 (d, J=8.0 Hz, 2H), 7.46-7.44 (d, J=8.0 Hz, 1H), 7.29-7.20 (m, 4H). LCMS (ESI) m/z: 552.9 (M+H)+.

Compound Example 61

3,5-Dichloro-nitrogen-(4-(nitrogen-(2-chloro-4-fluorophenyl) sulfamoyl) phenyl) benzenesulfonamide $^1$H NMR (400 MHz, DMSO-d6) δ11.09 (s, 1H), 9.93 (s, 1H), 7.98 (s, 1H), 7.78-7.77 (d, J=4.0 Hz, 1H), 7.29-7.25 (m, 4H), 7.19-7.14 (m, 1H). LCMS (ESI) m/z: 508.0 (M+H)+.

Compound Example 62

3,5-Dichloro-nitrogen-(4-(nitrogen-(3-chloro-5-bromophenyl) sulfamoyl) phenyl) benzenesulfonamide $^1$H NMR (400 MHz, DMSO-d6) δ11.18 (s, 1H), 10.81 (s, 1H), 7.88-7.75 (m, 5H), 7.34-7.32 (d, J=8.0, 2H), 7.15 (s, 1H), 7.01-6.70 (t, 1H), 6.88-7.87 (t, 1H). LCMS (ESI) m/z: 568.7 (M+H)+.

Compound Example 63

3,5-Dichloro-nitrogen-(4-(nitrogen-(3-fluoro-5-bromophenyl) sulfamoyl) phenyl) benzenesulfonamide $^1$H NMR (400 MHz, DMSO-d6) δ11.21 (s, 1H), 10.80 (s, 1H), 7.75-7.70 (m, 5H), 7.34-7.32 (d, J=8.0, 2H), 7.20 (s, 1H), 7.15-7.14 (t, 1H), 7.05-7.04 (t, 1H). LCMS (ESI) m/z: 551.8 (M+H)+.

Compound Example 64

3,5-Dichloro-nitrogen-(4-(nitrogen-(3-chloro-4-fluorophenyl) sulfamoyl) phenyl) benzenesulfonamide $^1$H NMR (400 MHz, DMSO-d6) δ11.14 (s, 1H), 10.42 (s, 1H), 7.87 (s, 1H), 7.75-7.66 (m, 4H), 7.30-7.22 (m, 3H), 7.14-7.13 (4, 1H), 7.02-7.00 (m, 1H). LCMS (ESI) m/z: 509.0 (M+H)$^+$.

Compound Example 65

3,5-Dichloro-nitrogen-(4-(nitrogen-(2,3,6-trifluoromethylphenyl) sulfamoyl) phenyl) benzenesulfonamide $^1$H NMR (400 MHz, DMSO-d6) δ11.11 (s, 1H), 10.34 (s, 1H), 7.94-7.93 (t, 1H), 7.77-7.76 (d, J=4.0 Hz, 2H), 7.48-7.41 ((m, 1H), 7.30-7.23 (m, 3H). LCMS (ESI) m/z: 510.9 (M+H)$^+$.

Compound Example 66

3,5-Dichloro-nitrogen-(4-(nitrogen-(2-methyl-4-fluoro-6-bromophenyl) sulfamoyl) phenyl) benzenesulfonamide δ11.14 (s, 1H), 9.71 (s, 1H), 7.97-7.96 (t, 1H), 7.79-7.78 (d, J=4.0 Hz, 2H), 7.55-7.53 (m, 1H), 7.31-7.29 (d, J=8.0 Hz, 2H), 7.14-7.10 (m, 2H), 1.71 (s, 3H). LCMS (ESI) m/z: 566.9 (M+H)$^+$.

Compound Example 67

3,5-Dichloro-nitrogen-(4-(nitrogen-(3-bromo-4-methyl-phenyl) sulfamoyl) phenyl) benzenesulfonamide δ11.15 (s, 1H), 10.32 (s, 1H), 7.84-7.83 (d, J=4.0 Hz, 1H), 7.76-7.75 (d, J=4.0 Hz, 2H), 7.69-7.67 (d, J=8.0 Hz, 2H), 7.30-7.28 (d, J=8.0 Hz, 2H), 7.20-7.19 (d, J=4.0 Hz, 2H), 7.14-7.12 (d, J=8.0 Hz, 2H), 6.97-6.94 (m, 1H), 2.16 (s, 3H). LCMS (ESI) m/z: 549.0 (M+H)$^+$.

Compound Example 68

3,5-Dichloro-nitrogen-(4-(nitrogen-(2-methyl-4-fluoro-5-bromophenyl) sulfamoyl) phenyl) benzenesulfonamide δ11.13 (s, 1H), 9.71 (s, 1H), 8.01-8.00 (t, 1H), 7.79-7.78 (d, J=4.0 Hz, 2H), 7.54-7.52d, J=8.0 Hz, 2H), 7.31-7.28 (d, J=12.0 Hz, 2H), 7.14-7.11 (m, 2H), 1.71 (s, 3H). LCMS (ESI) m/z: 566.9 (M+H)$^+$.

Compound Example 69

3,5-Dichloro-nitrogen-(4-(nitrogen-(2-methyl-4-fluorophenyl) sulfamoyl) phenyl) benzenesulfonamide δ11.09 (s, 1H), 9.51 (s, 1H), 8.00-7.99 (t, 1H), 7.78-7.77 (d, J=4.0 Hz, 2H), 7.53-7.50 (d, J=12.0 Hz, 2H), 7.29-7.27 (d, J=8.0 Hz, 2H), 6.95-6.88 (m, 3H), 1.75 (s, 3H). LCMS (ESI) m/z: 566.9 (M+H)$^+$.

Compound Example 71 tert-butyl4-(5-(3,5-dichlorophenyl) sulfonamide)-2-(nitrogen-(4-fluoro-2-methylphenyl))

δ11.10 (s, 1H), 9.78 (s, 1H), 8.06-8.05 (t, 1H), 7.78-7.77 (d, J=4.0 Hz, 2H), 7.62-7.61 (d, J=4.0 Hz, 1H), 7.54-7.52 (d, J=8.0 Hz, 1H), 7.19-7.11 (m, 2H), 6.97-6.95 (d, J=8.0 Hz, 1H), 3.67 (s, 2H), 3.34 (s, 4H), 2.24 (s, 4H), 1.77 (s, 3H), 1.42 (s, 9H). LCMS (ESI) m/z: 687.0 (M+H)$^+$.

Compound Example 71

4-(3,5-3,5-Dichlorophenyl sulfonamide)-nitrogen-(4-fluoro-2-methylphenyl)-2-(piperazin-1-methyl) phenylsulfonamide δ9.08 (s, 1H), 7.63-7.62 (d, J=4.0 Hz, 2H), 7.27-7.25 (d, J=8.0 Hz, 1H), 7.19-7.17 (m, 2H) 7.01-6.99 (d, J=8.0 Hz, 1H), 6.77-6.75 (d, J=8.0 Hz, 1H), 3.63 (s, 2H), 3.36 (s, 4H), 3.09 (s, 4H), 1.92-1.89 (m, 4H). LCMS (ESI) m/z: 586.9 (M+H)+.

Compound Example 81

(R)-Nitrogen-(5-bromo-4-fluoro-2-methylphenyl)-4-((2-fluorophenyl) sulfonamido)-2-((3-methylmorpholine) methyl) benzenesulfonamide $^1$H-NMR (400 MHz, DMSO-d6) δ11.21 (s, 1H), 9.79 (s, 1H), 8.01 (s, 1H), 7.78 (d, J=7.6 Hz, 1H), 7.64-7.53 (m, 4H), 7.51 (d, J=8.7 Hz, 1H), 7.19 (d, J=9.6 Hz, 1H), 7.03 (d, J=8.7 Hz, 1H), 6.92 (d, J=6.7 Hz, 1H), 3.90 (d, J=16.5 Hz, 1H), 3.58 (d, J=15.3 Hz, 1H), 3.39 (d, J=15.9 Hz, 2H), 3.17-3.07 (m, 1H), 2.45-2.36 (m, 1H), 1.81 (s, 3H), 0.79 (d, J=6.0 Hz, 3H) m/z (ESI) 631.6 (M+H)$^+$.

Compound Example 82

(R)-Nitrogen-(5-bromo-4-fluoro-2-methylphenyl)-2-((3-methylmorpholine) methyl)-(4-(2-(trifluoromethoxy) phenyl) sulfonamido) benzenesulfonamide $^1$H NMR (400 MHz, DMSO-d6) δ11.21 (s, 1H), 9.79 (s, 1H), 8.01 (s, 1H), 7.79 (s, 1H), 7.64-7.46 (m, 4H), 7.18 (s, 1H), 7.03 (s, 1H), 6.92 (s, 1H), 3.90 (s, 1H), 3.59 (s, 2H), 3.39 (s, 2H), 3.12 (s, 1H), 2.41 (s, 1H), 1.81 (s, 3H), 0.79 (d, J=6.2 Hz, 3H) m/z (ESI) 697.6 (M+H)$^+$.

Compound Example 83

(R)-Nitrogen-(5-bromo-4-fluoro-2-methylphenyl))-4-((3-bromophenyl)) sulfonamido)-2-((3-methylmorpholine)

$^1$H NMR (400 MHz, DMSO-d6) δ11.00 (s, 1H), 9.79 (s, 1H), 7.91 (s, 1H), 7.88 (d, J=8.0 Hz, 1H), 7.75 (d, J=8.1 Hz, 1H), 7.67 (s, 1H), 7.56-7.50 (m, 2H), 7.18 (d, J=9.6 Hz, 1H), 7.11-7.03 (m, 1H), 6.95 (d, J=6.7 Hz, 1H), 3.91 (d, J=16.7 Hz, 1H), 3.63 (td, J=9.1, 7.3, 3.3 Hz, 2H), 3.50-3.39 (m, 2H), 3.16 (dd, J=11.2, 8.2 Hz, 1H), 1.79 (s, 3H), 0.82 (d, J=6.2 Hz, 3H). m/z (ESI) 692.6 (M+H)⁺.

Compound Example 84

(R)-Nitrogen-(5-bromo-4-fluoro-2-methylphenyl))-4-((3-chlorophenyl)) sulfonamido)-2-((3-methylmorpholine)

¹H NMR (400 MHz, DMSO-d6) δ11.03 (s, 1H), 9.86 (s, 1H), 7.82-7.78 (m, 2H), 7.72 (s, 1H) 7.69 (d, J=2.2 Hz, 1H), 7.64 (d, J=8.0 Hz, 1H), 7.55 (d, J=8.6 Hz, 1H), 7.21 (d, J=9.6 Hz, 1H), 7.09 (dd, J=8.6, 2.4 Hz, 1H), 6.97 (d, J=6.7 Hz, 1H), 3.93 (d, J=16.8 Hz, 1H), 3.69-3.61 (m, 2H), 3.47 (d, J=11.6 Hz, 2H), 3.18 (dd, J=11.2, 8.4 Hz, 1H), 2.45 (d, J=7.7 Hz, 1H), 1.80 (s, 3H), 0.83 (d, J=6.2 Hz, 3H). m/z (ESI) 648.0 (M+H)⁺.

Compound Example 85

(R)-Nitrogen-(5-bromo-4-fluoro-2-methylphenyl)-4-((3, 5-dibromophenyl) sulfonamido)-2-((3-methylmorpholine) methyl) benzenesulfonamide ¹H NMR (400 MHz, DMSO-d6) δ11.10 (s, 1H), 9.88 (s, 1H), 8.29-8.22 (m, 1H), 8.01 (d, J=1.6 Hz, 1H), 7.91 (d, J=1.8 Hz, 2H), 7.71 (s, 1H), 7.56 (d, J=8.6 Hz, 1H), 7.19 (d, J=9.5 Hz, 1H), 7.11 (dd, J=8.6, 2.3 Hz, 1H), 7.01 (d, J=6.7 Hz, 1H), 3.94 (d, J=16.8 Hz, 1H), 3.67 (dd, J=8.3, 5.4 Hz, 2H), 3.49 (s, 2H), 3.25-3.16 (m, 1H), 2.46 (s, 1H), 1.78 (s, 3H), 0.84 (d, J=6.4 Hz, 3H). m/z (ESI) 771.4 (M+H)⁺.

Compound Example 86

(R)-Nitrogen-(5-bromo-4-fluoro-2-methylphenyl)-2-((3-methylmorpholine) methyl)-4-(benzenesulfonylamino) benzenesulfonamide ¹H NMR (400 MHz, DMSO-d6) δ10.87 (s, 1H), 9.85 (s, 1H), 7.83-7.78 (m, 2H), 7.66 (tq, J=2.9, 1.4 Hz, 2H), 7.58 (dd, J=8.3, 6.8 Hz, 2H), 7.53 (d, J=8.6 Hz, 1H), 7.22 (d, J=9.6 Hz, 1H), 7.08 (dd, J=8.6, 2.4 Hz, 1H), 6.95 (d, J=6.7 Hz, 1H), 3.93 (d, J=16.5 Hz, 1H), 3.64 (td, J=11.6, 3.3 Hz, 2H), 3.49-3.40 (m, 2H), 3.17 (dd, J=11.2, 8.3 Hz, 1H), 2.44 (ddd, J=9.0, 6.6, 3.0 Hz, 1H), 1.84 (s, 3H), 0.83 (d, J=6.3 Hz, 3H). m/z (ESI) 613.5 (M+H)⁺.

Compound Example 87

(R)-Nitrogen-(5-bromo-4-fluoro-2-methylphenyl)-4-((4-isopropylbenzene) sulfonamido)-2-((3-methylmorpholine) methyl) benzenesulfonamide ¹H NMR (400 MHz, DMSO-d6) δ10.89 (s, 1H), 9.81 (s, 1H), 7.74 (d, J=8.5 Hz, 2H), 7.67 (d, J=2.4 Hz, 1H), 7.54 (d, J=8.6 Hz, 1H), 7.46 (d, J=8.4 Hz, 2H), 7.21 (d, J=9.6 Hz, 1H), 7.07 (dd, J=8.6, 2.4 Hz, 1H), 6.97 (d, J=6.7 Hz, 1H), 3.92 (d, J=16.6 Hz, 1H), 3.68-3.58 (m, 2H), 3.48-3.41 (m, 2H), 3.16 (dd, J=11.2, 8.3 Hz, 1H), 2.96 (h, J=6.9 Hz, 1H), 2.43 (ddd, J=9.0, 6.3, 3.0 Hz, 1H), 1.85 (s, 3H), 1.18 (d, J=6.9 Hz, 6H), 0.81 (d, J=6.2 Hz, 3H). m/z (ESI) 654.7 (M+H)⁺.

Compound Example 88

(R)-Nitrogen-(5-bromo-4-fluoro-2-methylphenyl)-2-((3-methylmorpholine) methyl)-(4-(2-(trifluoromethyl) phenyl) sulfonamido) benzenesulfonamide ¹H NMR (400 MHz, DMSO-d6) δ11.04 (s, 1H), 9.82 (s, 1H), 8.12-7.99 (m, 2H), 7.83 (t, J=8.3 Hz, 1H), 7.66 (s, 1H), 7.53 (d, J=8.6 Hz, 1H), 7.15 (d, J=9.6 Hz, 1H), 7.09 (d, J=8.4 Hz, 1H), 6.95 (d, J=6.7 Hz, 1H), 3.89 (d, J=16.8 Hz, 1H), 3.66-3.55 (m, 2H), 3.41 (d, J=17.0 Hz, 2H), 3.12 (d, J=20.1 Hz, 1H), 2.41 (s, 1H), 1.76 (s, 3H), 0.78 (d, J=6.2 Hz, 3H). m/z (ESI) 681.5 (M+H)⁺.

Compound Example 89

(R)-Nitrogen-(5-bromo-4-fluoro-2-methylphenyl) 4 ((4 (tert-butyl) phenyl) sulfonamido)-2-((3-methylmorpholine) methyl) benzenesulfonamide ¹H NMR (400 MHz, DMSO-d6) δ10.94 (s, 1H), 9.82 (s, 1H), 7.75 (d, J=8.6 Hz, 2H), 7.61 (d, J=8.6 Hz, 2H), 7.54 (d, J=8.6 Hz, 1H), 7.20 (d, J=9.5 Hz, 1H), 7.07 (dd, J=8.7, 2.4 Hz, 1H), 6.98 (d, J=6.7 Hz, 1H), 3.91 (d, J=16.6 Hz, 1H), 3.69-3.57 (m, 2H), 3.44 (dd, J=18.7, 11.1 Hz, 2H), 3.16 (dd, J=11.2, 8.4 Hz, 1H), 2.42 (s, 1H), 2.00 (s, 3H), 1.26 (s, 9H), 0.79 (d, J=6.2 Hz, 3H). m/z (ESI) 669.7 (M+H)⁺.

Compound Example 90

(R)-Nitrogen-(5-bromo-4-fluoro-2-methylphenyl)-4-((2-chlorophenyl) sulfonamido)-2-((3-methylmorpholine) methyl) benzenesulfonamide ¹H NMR (400 MHz, DMSO-d6) δ11.24 (s, 1H), 9.79 (s, 1H), 8.09-8.07 (d, J=8.0 Hz, 1H), 7.66-7.64 (d, J=8.0 Hz, 2H), 7.54 (t, 1H), 7.49-7.47 (d, J=8.0 Hz, 1H), 7.18-7.16 (d, J=12.0 Hz, 1H), 7.04-7.02 (d, J=8.0 Hz, 1H), 6.90-6.88 (d, J=8.0 Hz, 1H), 3.89 (s, 1H), 3.67-3.57 (m, 2H), 3.41 (d, J=12.0 Hz, 2H), 3.20-3.11 (m, 1H), 2.41-2.39 (d, J=8.0 Hz, 1H), 1.78 (s, 3H), 0.79 (s, 3H). m/z (ESI) 648.0 (M+H)⁺.

Compound Example 91

Methyl 2-(nitrogen-(5-bromo-4-fluoro-2-methylphenyl)) aminosulfonyl)-5-(3, 5-dichlorophenyl sulfonamido) benzoate ¹H NMR (400 MHz, DMSO-d6) δ11.36 (s, 1H), 9.46 (s, 1H), 8.05 (s, 1H), 7.81-7.80 (d, J=4.0 Hz, 2H), 7.58-7.56 (d, J=8.0 Hz, 1H), 7.42-7.39 (d, J=12.0 Hz, 1H), 3.73 (s, 1H), 1.80 (s, 3H). m/z (ESI) 627.2 (M+H)⁺.

Compound Example 92

(R)-Nitrogen-(5-bromo-4-fluoro-2-methylphenyl)-4-(3,5-dichlorophenyl sulfonamido)-2-((3-hydroxypyrrolidin-1-yl) methyl) benzenesulfonamide ¹H NMR (400 MHz, DMSO-d6) δ7.98 (s, 1H), 7.78-7.77 (d, J=4.0 Hz, 2H), 7.44-7.42 (d, J=8.0 Hz, 1H), 7.36 (s, 1H), 7.22-7.19 (d, J=12.0 Hz, 1H), 7.10-7.07 (m, 1H), 6.78-6.77 (d, J=8.0 Hz, 1H), 4.96 (s, 1H), 4.25 (s, 1H), 4.07-3.95 (m, 2H), 2.08-2.00 (m, 1H), 1.93 (s, 1H), 1.59 (s, 1H). m/z (ESI) 668.3 (M+H)⁺.

Compound Example 93

Nitrogen-(5-bromo-4-fluoro-2-methylphenyl)-4-(3, 5-dichlorophenyl sulfonamide)-2-((ethyl (propyl) amino) methyl) benzenesulfonamide ¹H NMR (400 MHz, DMSO-d6) δ7.96 (s, 1H), 7.73-7.72 (d, J=4.0 Hz, 2H), 7.55-7.53 (d, J=8.0 Hz, 2H), 7.19-7.17 (d, J=8.0 Hz, 1H), 7.08-7.06 (m, 1H), 6.93-6.91 (d, J=8.0 Hz, 1H), 4.75 (s, 2H), 2.45-2.36 (m, 4H), 1.98 (s, 1H), 1.37-1.31 (m, 2H), 0.95-0.93 (m, 4H), 0.80-0.77 (m, 3H). m/z (ESI) 668.3 (M+H)+.

Compound Example 94

Nitrogen-(5-bromo-4-fluoro-2-methylphenyl))-4 (3,5-dichlorophenyl sulfonamide)-2 ((4-(2-ethoxyethyl)) piperazine-1-yl) methyl) benzenesulfonamide ¹H NMR (400 MHz, DMSO-d6) δ7.97-7.96 (t, 1H), 7.75-7.74 (d, J=4.0 Hz, 2H), 7.45-7.43 (d, J=8.0 Hz, 2H), 7.21-7.19 (d, J=8.0 Hz, 1H), 7.04-7.01 (m, 1H), 6.86-6.84 (d, J=8.0 Hz, 1H), 3.70 (s, 2H), 3.54-3.52 (t, 2H), 3.45-3.40 (m, 2H), 2.71-2.43 (m, 8H), 1.87 (s, 1H), 1.12-1.08 (t, 3H). m/z (ESI) 739.4 (M+H)⁺.

Compound Example 95

Nitrogen-(5-bromo-4-fluoro-2-methylphenyl)-2 ((4-cyclopentylpiperazin-1-yl) methyl)-4-(3,5-dichlorophenyl sulfonamido) benzenesulfonamide δ7.88 (s, 1H), 7.71-7.70 (d, J=4.0 Hz, 2H), 7.38-7.36 (d, J=8.0 Hz, 2H), 7.32 (s, 1H), 7.22-7.19 (d, J=8.0 Hz, 1H), 6.94-6.91 (m, 1H), 6.84-6.83 (d, J=4.0 Hz, 1H), 3.67 (s, 2H), 2.75-2.43 (m, 8H), 1.91-1.84 (m, 5H), 1.63-1.40 (m, 6H). m/z (ESI) 739.4 (M+H)⁺.

Compound Example 96

Nitrogen-(5-bromo-4-fluoro-2-methylphenyl)-4-(3, 5-dichlorophenyl sulfonamido)-2-((4-(2-hydroxyethyl) piperazin-1-yl) methyl) benzenesulfonamide ¹H NMR (400 MHz, DMSO-d6) δ7.72-7.71 (t, 1H), 7.63-7.62 (d, J=4.0 Hz, 2H), 7.25-7.18 (m, 2H), 7.08-7.07 (d, J=4.0 Hz, 1H), 6.75-6.72 (m, 1H), 6.58-6.57 (d, J=4.0 Hz, 1H), 4.45 (s, 1H), 3.65 (s, 2H), 3.48-3.47 (m, 8H), 2.07 (s, 3H). m/z (ESI) 711.4 (M+H)⁺.

Compound Example 97

(S)—N-(3-bromo-4-fluorophenyl)-4 (3, 5-dichlorophenyl sulfonamide)-2 ((2-methylpyrrolidin-1-yl) methyl) benzenesulfonamide ¹H NMR (400 MHz, DMSO-d6) δ7.78 (t, 1H), 7.66-7.65 (d, J=4.0 Hz, 2H), 7.37-7.35 (d, J=8.0 Hz, 1H), 7.21-7.19 (d, J=8.0 Hz, 2H), 6.88-6.81 (m, 2H), 4.30-4.26 (d, J=16.0 Hz, 1H), 2.66 (s, 2H), 2.17 (s, 1H), 1.99 (s, 3H), 1.67-1.54 (m, 2H), 1.35 (s, 1H), 1.11-1.09 (m, 3H). m/z (ESI) 652.3 (M+H)⁺.

Compound Example 98

Nitrogen-(3-bromo-4-fluorophenyl)-2 ((4-cyclopropylpiperazin-1-yl)) methyl)-4-(3,5-dichlorophenyl sulfonamido)) benzenesulfonamide ¹H NMR (400 MHz, DMSO-d6) δ7.85 (s, 1H), 7.69-7.68 (d, J=4.0 Hz, 2H), 7.36-7.34 (d, J=8.0 Hz, 1H), 7.30 (s, 1H), 7.22-7.19 (d, J=12.0 Hz, 1H), 6.92-6.89 (m, 1H), 6.83-6.81 (d, J=8.0 Hz, 1H), 3.67 (s, 2H), 2.70-2.43 (m, 1H), 1.92 (s, 3H), 0.87-0.86 (m, 1H), 0.53-0.49 (m, 2H), 0.15-0.14 (m, 2H). m/z (ESI) 693.3 (M+H)⁺.

Compound Example 99

Nitrogen-(3-bromo-4-fluorophenyl)-4 (3,5-dichlorophenyl sulfonamide)-2 ((4-isopropylpiperazin-1-yl) methyl) benzenesulfonamide ¹H NMR (400 MHz, DMSO-d6) δ7.73-7.72 (t, 1H), 7.64-7.63 (d, J=4.0 Hz, 2H), 7.24-7.21 (d, J=12.0 Hz, 2H), 7.09-7.08 (d, J=4.0 Hz, 1H), 6.77-6.74 (m, 1H), 6.67-6.65 (d, J=8.0 Hz, 1H), 3.65 (s, 2H), 2.70-2.64 (m, 1H), 2.50-2.41 (m, 6H), 2.04 (s, 3H), 0.95-0.93 (d, 6H). m/z (ESI) 695.4 (M+H)⁺.

Compound Example 100

Nitrogen-(3-bromo-4-fluorophenyl)-4 (3,5-dichlorophenyl sulfonamide)-2 ((4-(oxyethyl-3-yl) piperazin-1-yl) methyl) benzenesulfonamide ¹H NMR (400 MHz, DMSO-d6) δ7.73-7.72 (t, 1H), 7.64-7.63 (d, J=4.0 Hz, 2H), 7.24-7.18 (t, 2H), 7.10-7.09 (d, J=4.0 Hz, 1H), 6.74-6.72 (m, 1H), 6.59-6.58 (d, J=4.0 Hz, 1H), 4.51-4.48 (t, 2H), 4.39-4.36 (t, 2H), 3.66 (s, 2H), 3.38-3.26 (m, 2H), 2.39-2.05 (m, 10H). m/z (ESI) 709.3 (M+H)⁺.

Example 8. Verification Experiments

Experiment 1: The Verification Experiment of SIRT6 Small-Molecular Activator on the Activation Effect of SIRT6

In the present verification experiment, the SIRT 6 small-molecular activator of the present invention is verified for the activation effect of the SIRT6 deacetylation activity. The SIRT6 small-molecular activator of the present invention is an active ingredient in the compounds listed in Table 1.

In the present embodiment, the deacetylation activity of SIRT 6 is detected by using a fluorescent quantitative method, and the principle is: first labeling fluorescein 7-amino-4-methylcoumarin (AMC) on the C-terminal of the acetylated polypeptide (ε-acetyL); then, after deacetylation of ε-ACELTYLL using SIRT 6, using trypsin to shear to produce free AMC, thereby performing fluorescence quantification on the reaction.

The specific experimental method comprises the following steps: taking 50 µl of reaction liquid for reaction at 37° C. for 2 hours, and adding 40 mmol/L of nicotinamide to terminate the reaction; then adding 6 mg/mL trypsin to carry out chromogenic reaction at 25° C. for 30 minutes; and finally, carrying out fluorescence quantitative detection on the reaction through an enzyme label instrument (Synergy-H 4 Hybrid Reader), wherein the excitation wavelength and the emission wavelength are 360 nm and 460 nm, respectively. The blank group reaction solution comprises 2 5 mmol/L of NAD⁺, 75 μmol/L RHKK-Ac'-AMC, 5 μmol/L of SIRT 6, wherein the reaction buffer consists of 50 mmol/L of Tris-Limonene L, 137 mmol/L of NaCl, 2.7 mM L of KCl, and 1 mmol/L of MgCl2, and the pH value is 8. Experimental Group Reaction Liquid further comprises 100 μmol/L of agonist, wherein the activator is a DMSO solution of the compound of Table 1.

Comparing the blank group to the experimental group SiRT 6 deacetylation activity to obtain the experimental results as shown in FIGS. 1-8, the compounds listed in Table 1 have an activation effect on SIRT 6.

Experiment 2: Half Maximum Effect Concentration Assay for SIRT 6 Small Molecule Allosteric Agonists A half maximum effect concentration ($EC_{50}$) of the SIRT 6 small molecule allosteric activator of the present invention is further determined in this experiment, which is an active ingredient for the compounds listed in Table 1.

Figure 9:
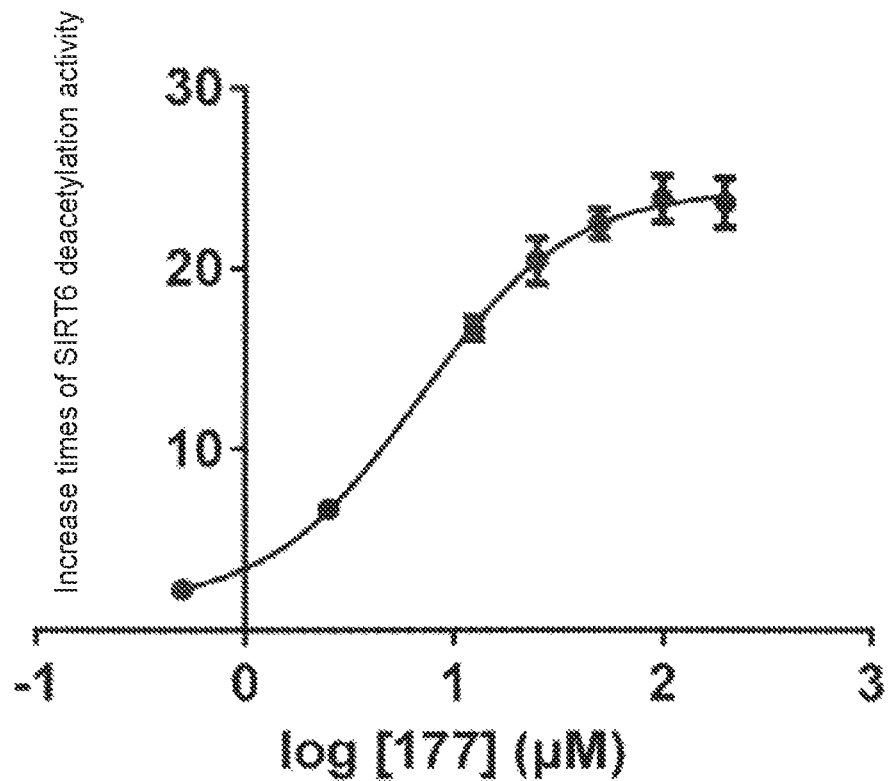
FIG. 9 to FIG. 37 are half maximum effect concentration curves of the SIRT6 small-molecule allosteric activator according to the invention.
Figure 10:
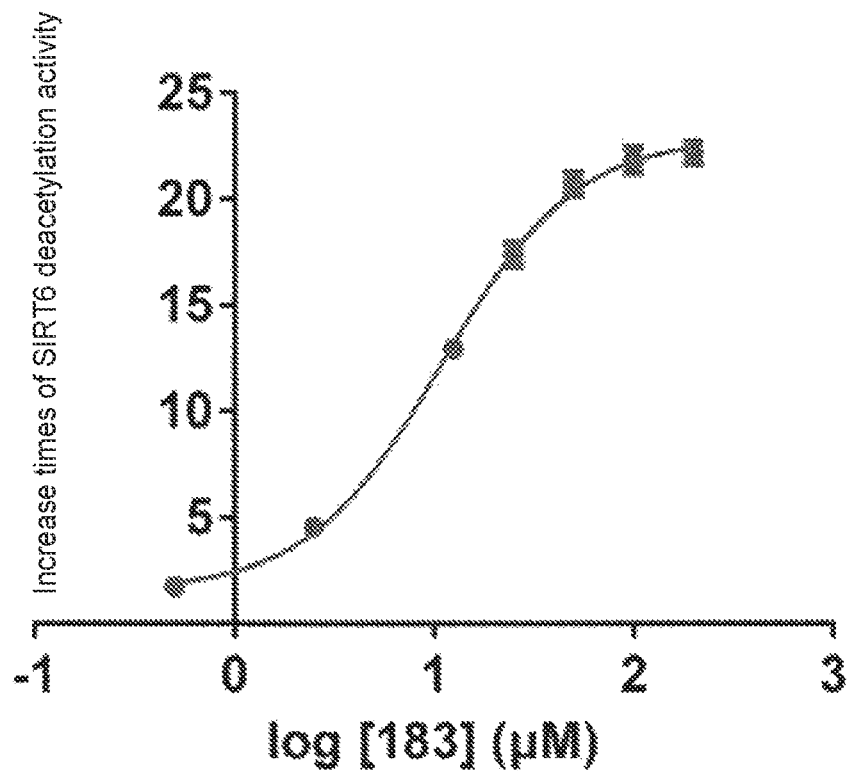

The deacetylation activity of SIRT6 is determined experimentally, the assay data was finally determined by GraphPad Prism 6 software to solve for the $EC_{50}$ activation effect of the agonist at various concentration values, as shown in FIGS. 9 and 10. FIG. 9 and FIG. 10 illustrate the activation of SIRT6 deacetylation activity in a concentration-dependent manner with compound 177 and an activator of compound 183 as an active ingredient.

Figure 11:
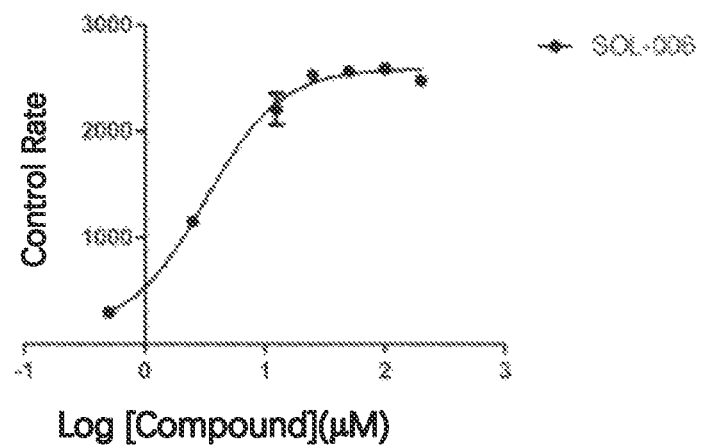
Figure 12:
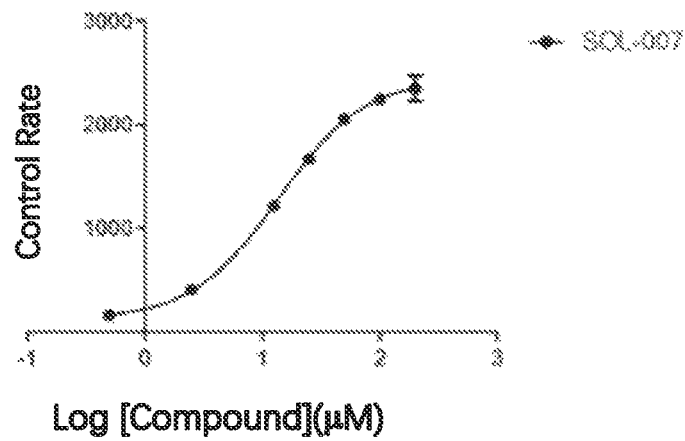
Figure 13:
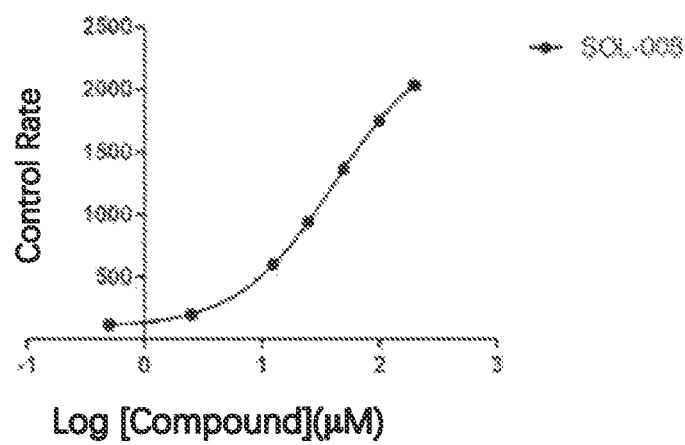
Figure 14:
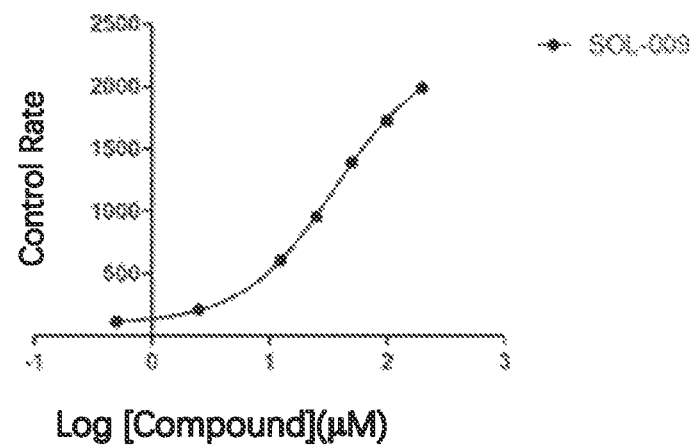
Figure 15:
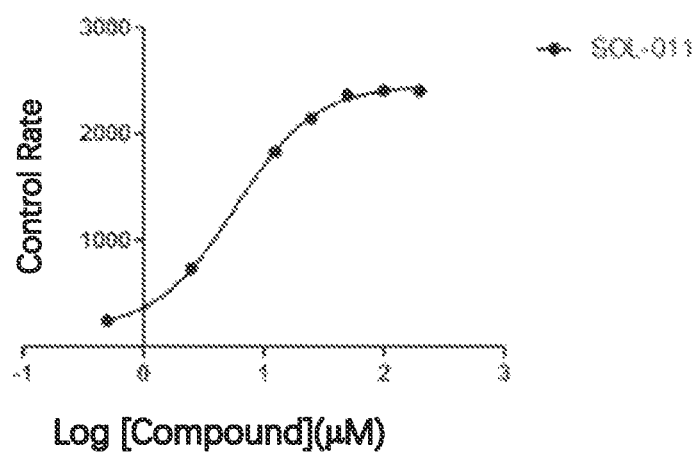
Figure 16:
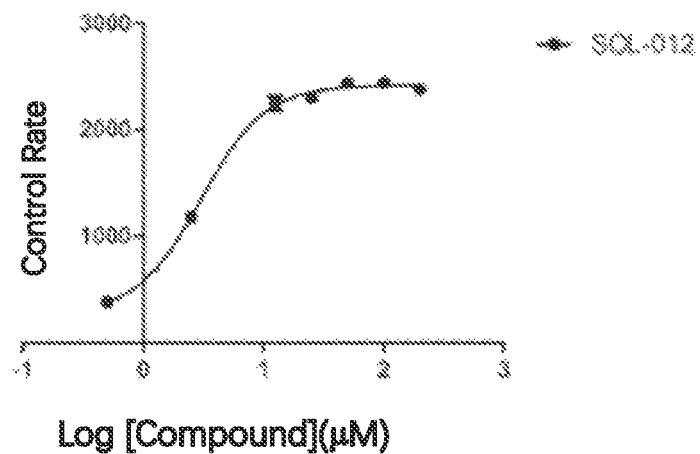
Figure 17:
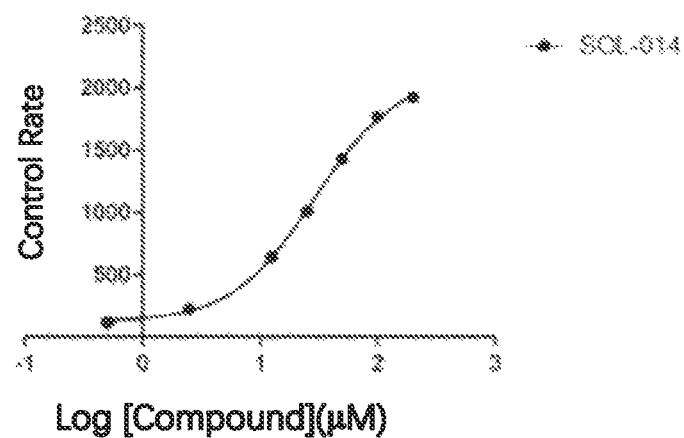
Figure 18:
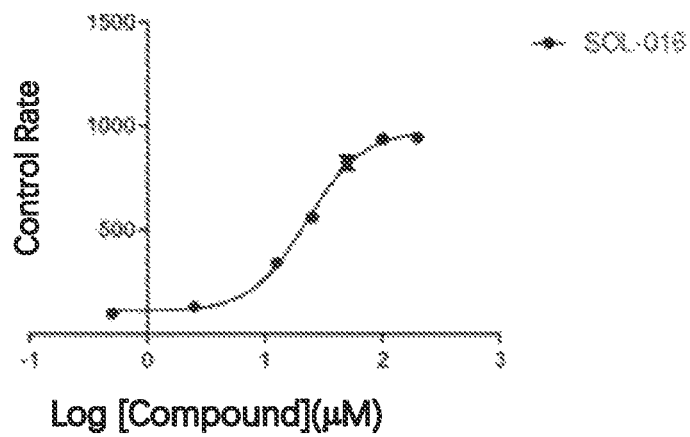
Figure 19:
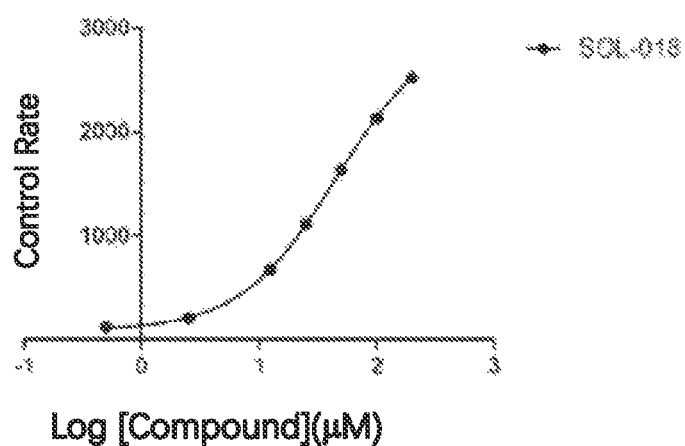
Figure 20:
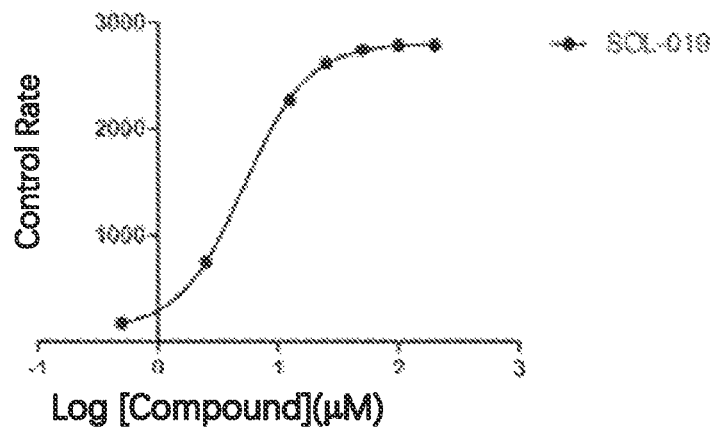
Figure 21:
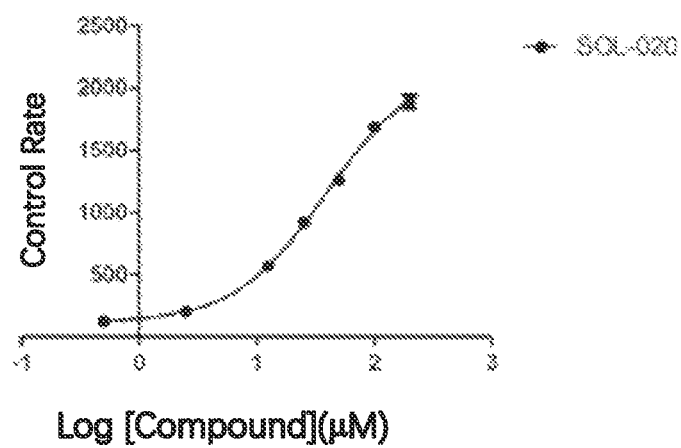
Figure 22:
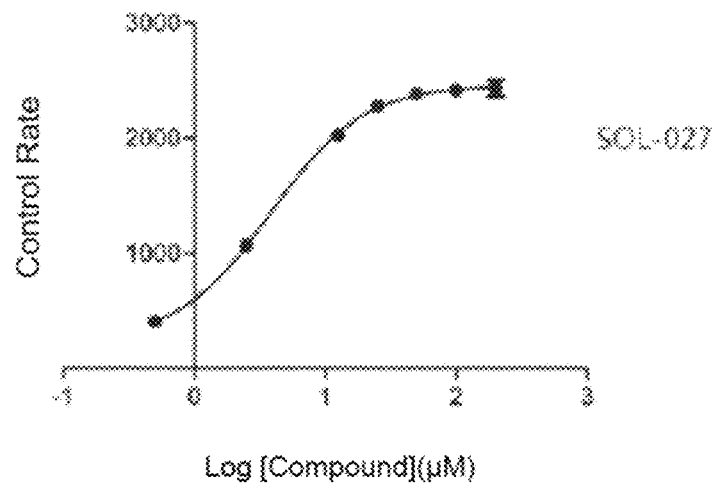
Figure 23:
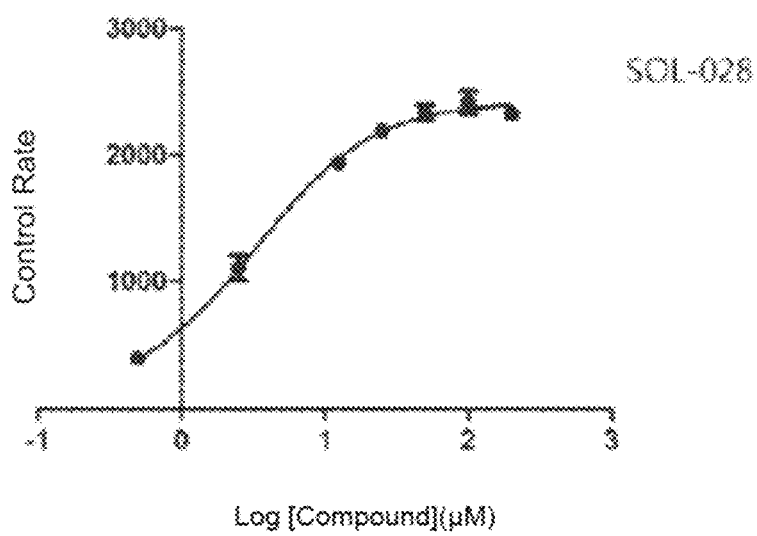
Figure 24:
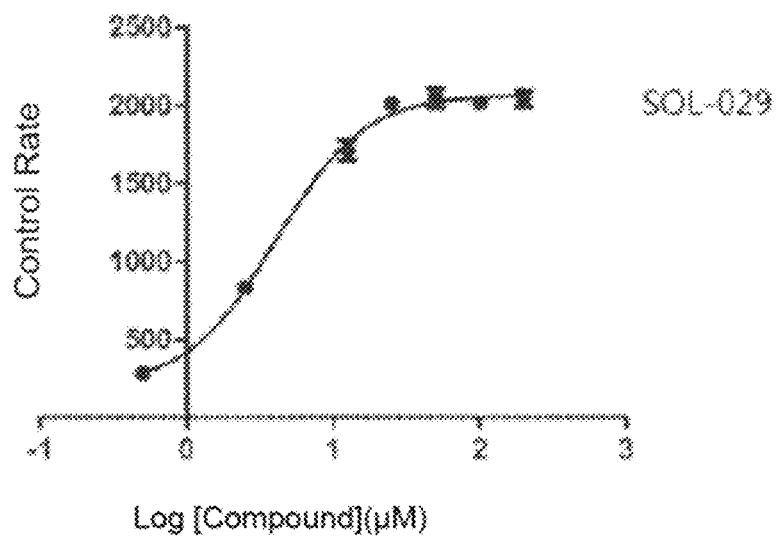
Figure 25:
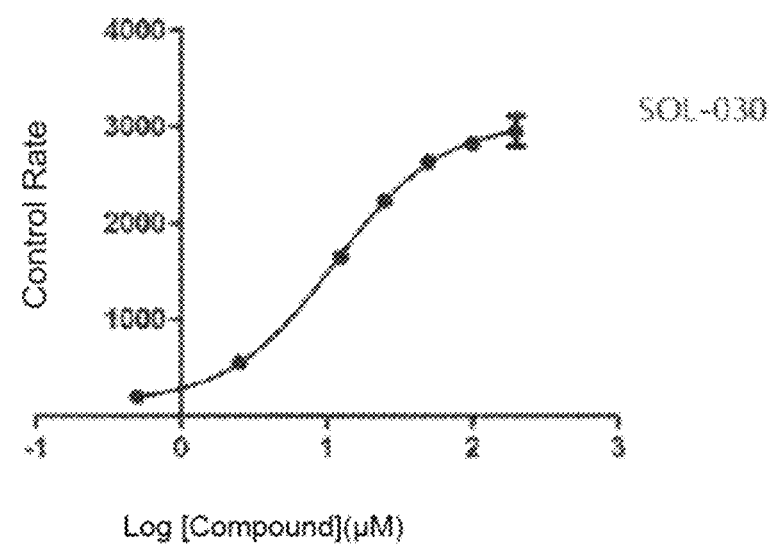
Figure 26:
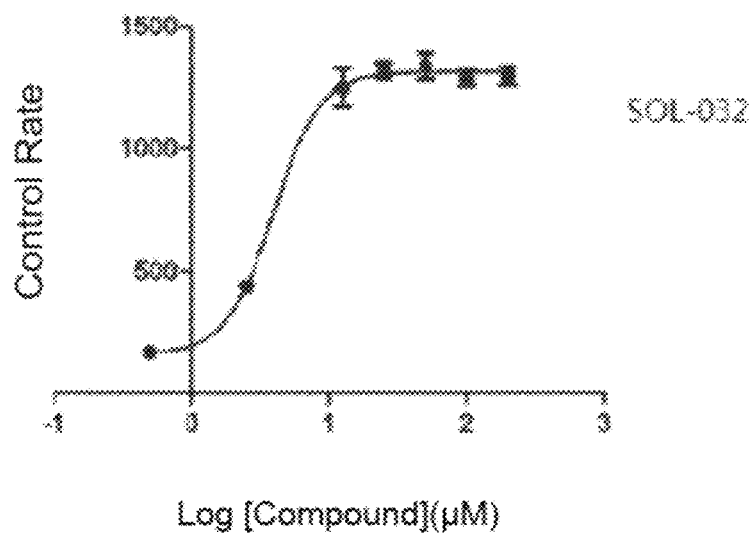
Figure 27:
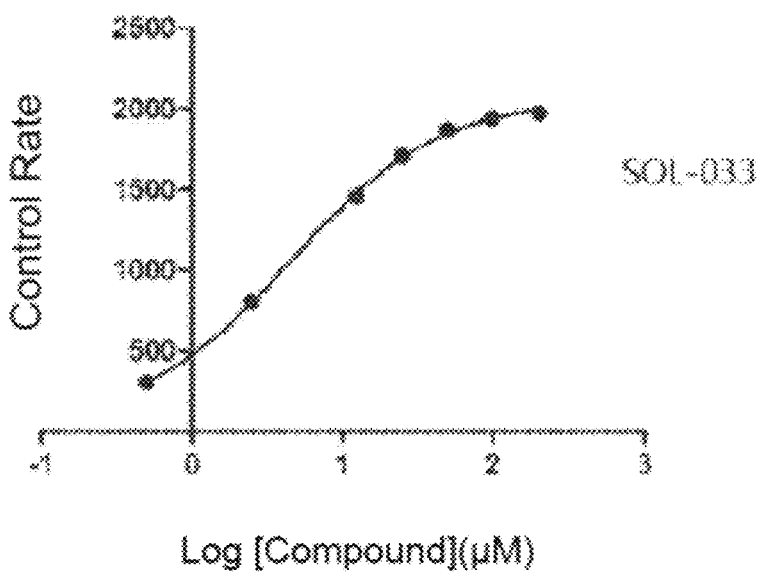
Figure 28:
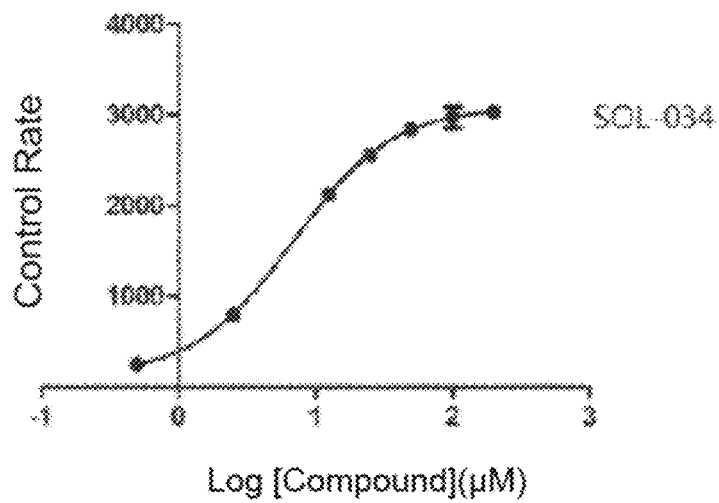
Figure 29:
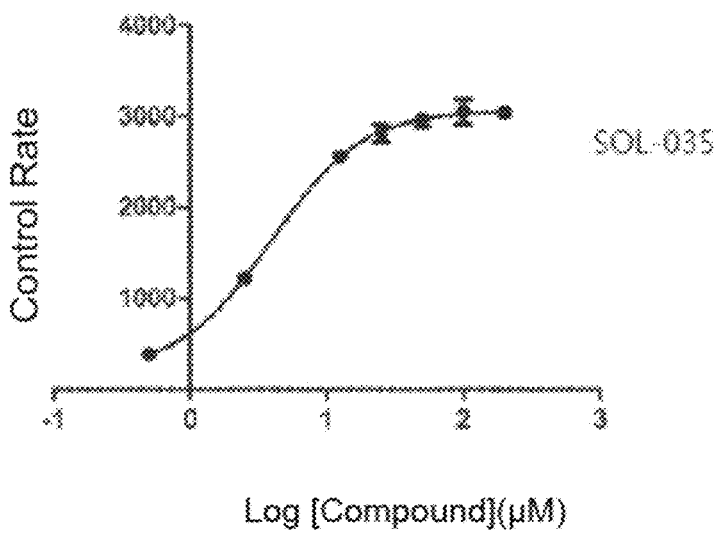
Figure 30:
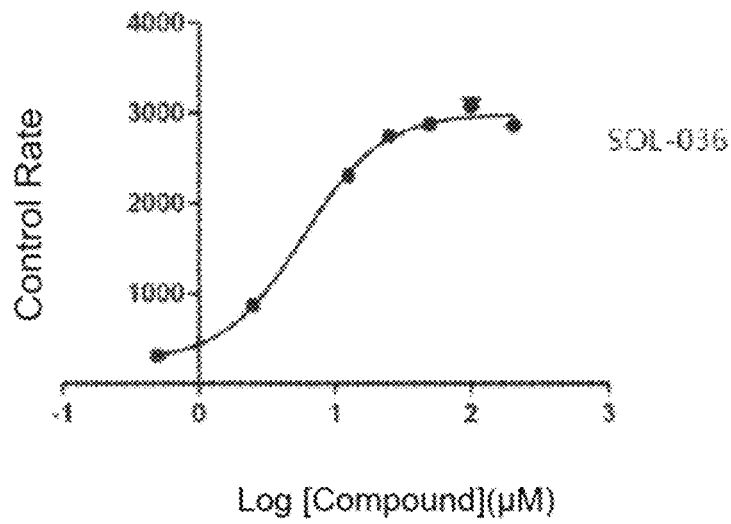
Figure 31:
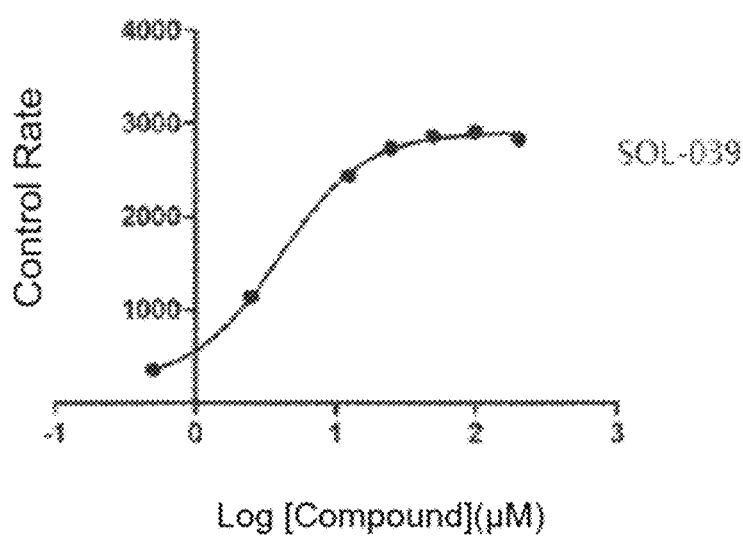
Figure 32:
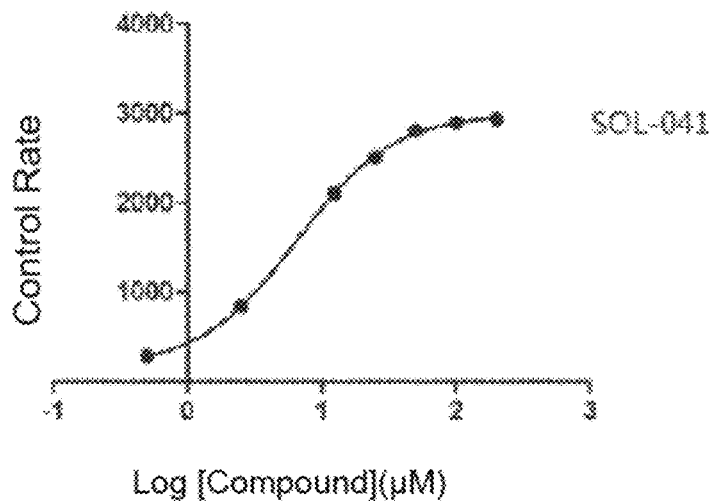
Figure 33:
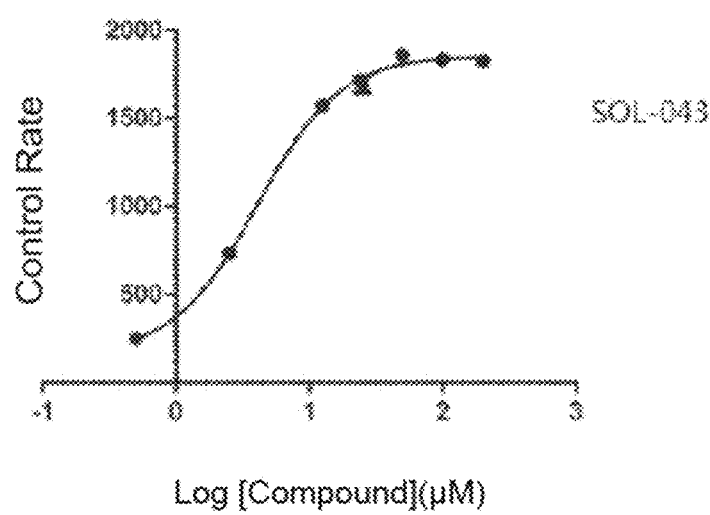
Figure 34:
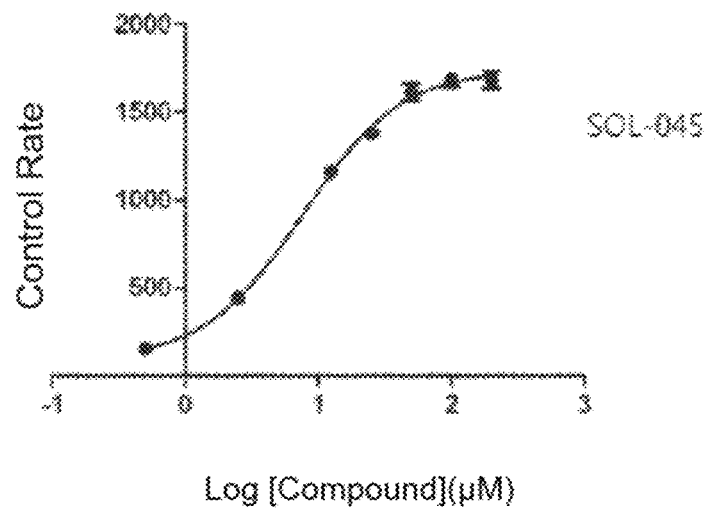
Figure 35:
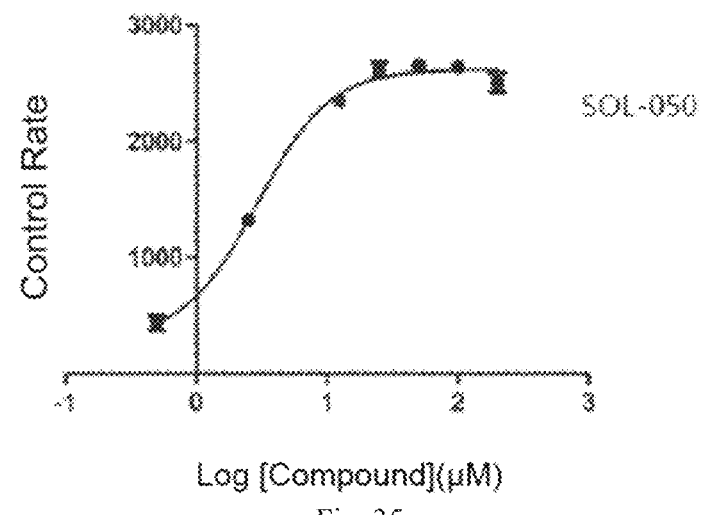
Figure 36:
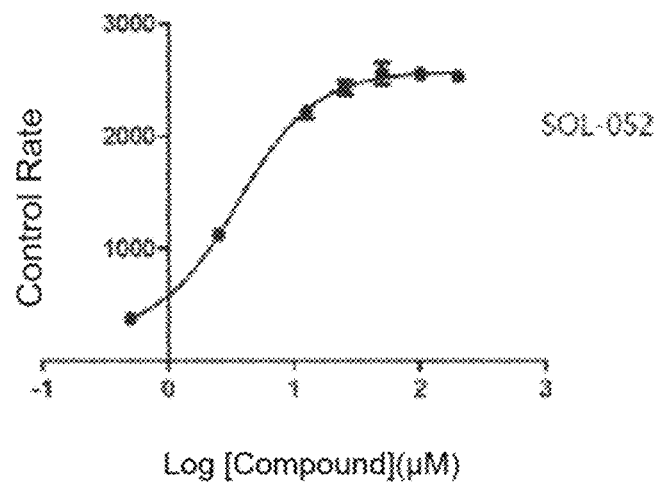
Figure 37:
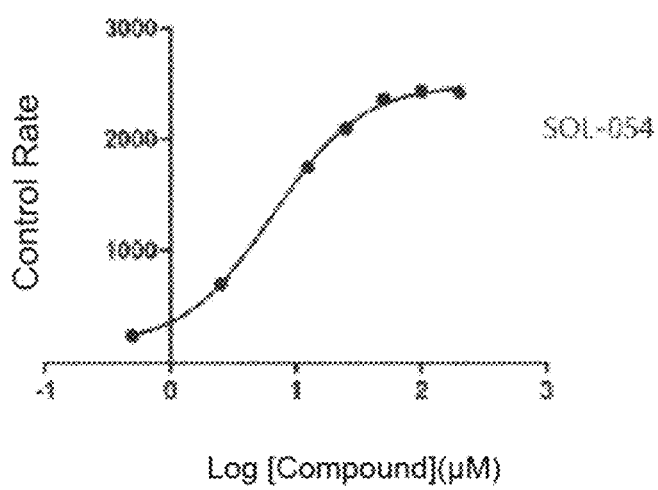

The $EC_{50}$ of the SIRT6 small molecule allosteric activator as an active ingredient in the compounds listed in Table 2 is also further determined in this experiment, as shown in FIGS. 11 and 37. FIGS. 11-37 illustrate the activation of the SIRT6 deacetylation activity in dependence on the activator, respectively, of the compounds listed in Table 2 as the active ingredient.

Experiment 3: Cell Detection

A Western Blot experimental method is used to detect the effect of SIRT6 small molecule allosteric activator as active ingredients in Table 1 and Table 2 for SIRT6 deacetylated active substrates H3K9 AC and H3K56 AC in cell cells.

(i) Cell Culture

HEK-293 T cells, Bel7405 cells, PLC/PFR/5 cells, Bel 7402 cells, HCT116 cells, HT29 cells, SW 480 cells, and HCT116 cells are test objects.

HEK-293 T cells and PLC/PFR/5 cells are cultured in DMEM containing 100 U/ml penicillin, 100 μg/ml streptomycin, and 10% FBS; BEL 7402 cells and BEL 7405 cells were cultured in RPMI-1640 Medium A Medium containing 100 U/ml penicillin, 100 μg/ml streptomycin, and 10% FBS. The above cell lines were analyzed by Short Tandem Repeat Repeat (STR).

(ii) Treatment of Cells

Step 1: the compound mother liquor (solvent is DMSO) listed in Table 1 and Table 2, the gradient concentration comprising 0.5 μmol/L, 1 μmol/L, 5 μmol/L, 10 μmol/L, 25 μmol/L and 50 μmol/L;

Step 2: $3*10^5$ (HEK-293 T cells) or $5*10^5$ (Bel 7405, PLC/PFR/5 and Bel 7402 cells), cultured at 37° C. and 5% $CO_2$ conditions;

Step 3: the cell state was good after 24 hours, the fresh culture solution (2 mL) was replaced, and the mother liquor configured above is added to the cell culture solution of the experimental group according to the ratio of 1:1000; the same volume of DMSO (2 ul) is added to the cell culture solution of the control group;

Step 4: continue to culture for a certain time (12 hours, 24 hours, 48 hours or 60 hours).

(iii) Western Blot Detection 1) for each group of cells at the end of culture, the culture medium in each well is discarded and washed with 1*PBS once;

2) add 150 μl SDS lysate containing bromophenol blue into each well, mix well and transfer to 1.5 ml EP tube respectively;

3) store at 95° C. for 5 min, then on ice for 5 min, repeat three times;

4) the supernatant is centrifuged at 12000×g for 5 min for Western blot detection. The antibody information used in this experiment is shown in Table 3.

TABLE 3

Western blot parameters

| Antibody | Producer | Article No. | Dilution rate |
|---|---|---|---|
| SIRT6 | Cell Signaling | 12486 | 1:2000 |
| Histone H3 (acetyl K9) | Abcam | ab32129 | 1:1000 |
| Histone H3 (acetyl K56) | Active Motif | 39281 | 1:1000 |
| Histone H3 (acetyl K14) | Abcam | ab52946 | 1:1000 |
| Histone H3 | Abcam | ab10799 | 1:2000 |
| beta actin | Proteintech | HRP-6008 | 1:5000 |

The test results are shown in FIGS. 38 to 47.

Figure 38:
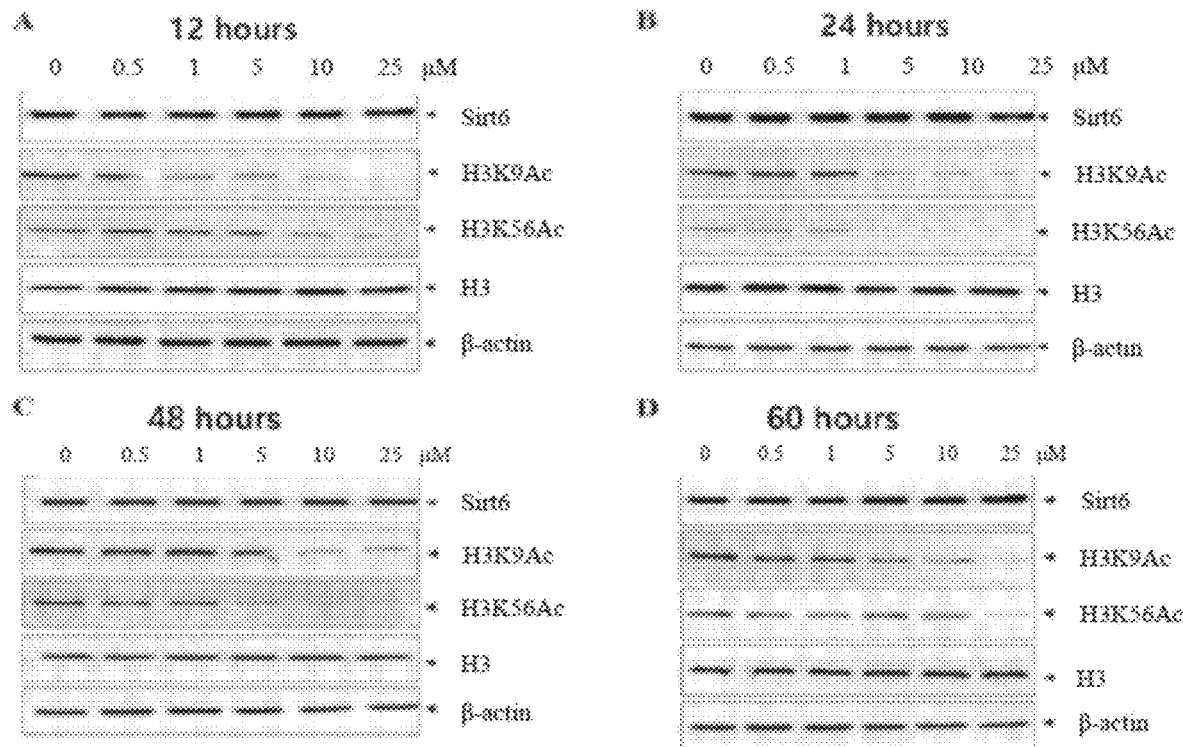
FIG. 38 is a schematic diagram of treating HEK-293T cells for 12 hours, 24 hours, 48 hours or 60 hours with the compound 177 at different concentrations.

Hek-293t cells are treated with different concentrations of compound 177 in Table 1 for 12 hours, 24 hours, 48 hours or 60 hours, H3K9Ac and h3k56ac, which are the active substrates of SIRT6 deacetylation, are detected by blot method as shown in FIG. 38. The results showed that compound 177 could modulate H3K9Ac and h3k56ac in a concentration dependent manner, so compound 177 could activate SIRT6 deacetylation activity in hek-293t cells.

Figure 39:
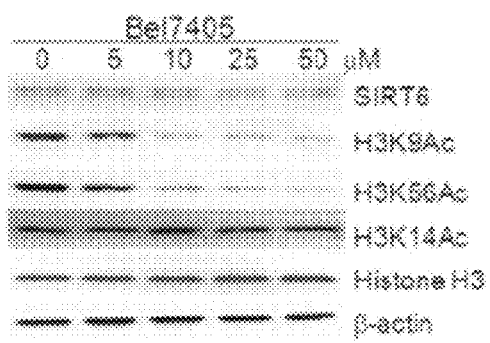
FIG. 39 is a schematic diagram of the SIRT6 deacetylation active substrate H3K9Ac and H3K56Ac in a cell after treatment of Bel7405 cells with the compound 183 at different concentrations for 48 hours.

After treating Bel7405 cells with different concentrations of compound 183 in Table 1 for 48 hours, the intracellular SIRT6 deacetylation active substrates H3K9Ac and H3k56ac are detected by Western blot, as shown in FIG. 39. The results showed that compound 183 could down regulate H3K9Ac and H3k56ac in a concentration dependent manner, and the reactive compound 183 could activate SIRT6 deacetylation activity in bel7405 cells.

Figure 40:
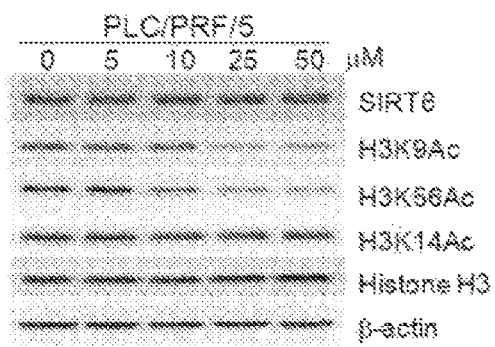
FIG. 40 is a schematic diagram of the SIRT6 deacetylation active substrate H3K9Ac and H3K56Ac in a cell after treatment of PLC/PFR/5 cells with the compound 183 at different concentrations for 48 hours.

After PLC/PRF/5 cells are treated with different concentrations of compound 183 in Table 1 for 48 hours, the intracellular SIRT6 deacetylation active substrates H3K9Ac and H3k56ac are detected by Western blot, as shown in FIG. 40. The results showed that compound 183 could down regulate H3K9Ac and H3k56ac in a concentration dependent manner, and the reactive compound 183 could activate SIRT6 deacetylation activity in PLC/PRF/5 cells.

Figure 41:
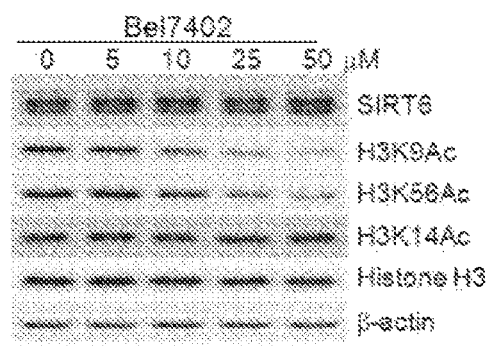
FIG. 41 is a schematic diagram of the SIRT6 deacetylation active substrate H3K9Ac and H3K56Ac in a cell after treatment of Bel7405 cells with the compound 183 at different concentrations for 48 hours.

After Bel7402 cells are treated with different concentrations of compound 183 in Table 1 for 48 hours, the intracellular SIRT6 deacetylation substrates H3K9Ac and H3k56ac are detected by Western blot, as shown in FIG. 41. The results showed that compound 183 could down regulate H3K9Ac and H3k56ac in a concentration dependent manner, and the reactive compound 183 could activate SIRT6 deacetylation activity in Bel7402 cells.

Figure 42:
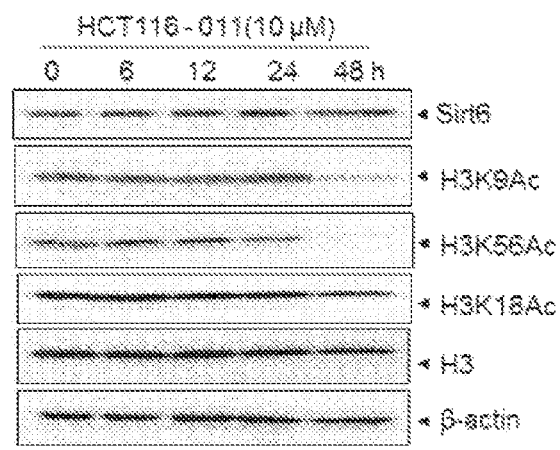
FIG. 42 is a schematic diagram of the SIRT6 deacetylation active substrate H3K9Ac and H3K56Ac in a cell after HCT116 cells are treated with the compound SOL-011 of 10 μmol/L for 24 hours and 48 hours.

After HCT116 cells are treated with 10 μmol/L compound SOL-011 in Table 2 for 24 hours and 48 hours, H3K9Ac and H3k56ac are detected by Western blot. As shown in FIG. 42, compound SOL-011 down regulated H3K9Ac and H3k56ac, which indicated that compound SOL-011 could activate SIRT6 deacetylation activity in HCT116 cells.

Figure 43:
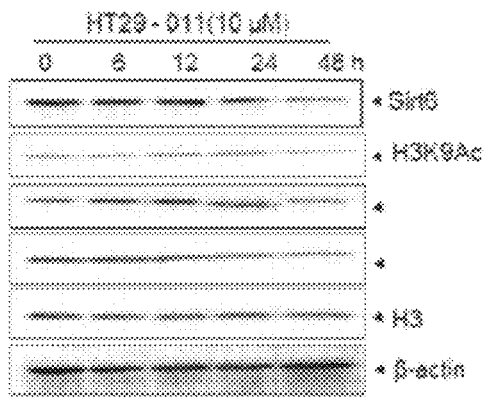
FIG. 43 is a schematic diagram of the SIRT6 deacetylation active substrate H3K9Ac and H3K56Ac in a cell after HT29 cells are treated with the compound SOL-011 of 10 μmol/L for 24 hours and 48 hours.

After HT29 cells are treated with 10 μmol/L compound SIK-011 in Table 2 for 24 hours and 48 hours, the intracellular SIRT6 deacetylation activity substrates H3K9Ac and h3k56ac are detected by Western blot method, as shown in FIG. 43. The results showed that compound SOL-011 down regulated H3K9Ac and H3k56ac, and the reactive compound SOL-011 could activate SIRT6 deacetylation activity in HT29 cells.

Figure 44:
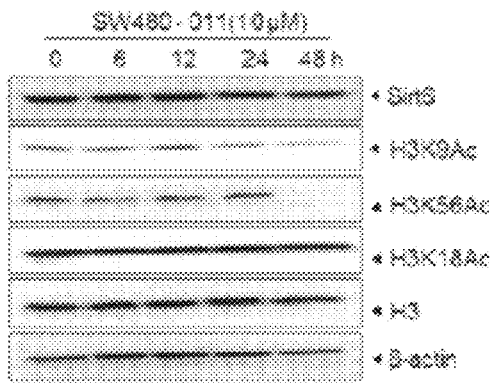
FIG. 44 is a schematic diagram of the SIRT6 deacetylation active substrate H3K9Ac and H3K56Ac in a cell after SW480 cells are treated with the compound SOL-011 of 10 μmol/L for 24 hours and 48 hours.

After SW480 cells are treated with 10 μmol/L compound SOL-011 in Table 2 for 24 hours and 48 hours, H3K9Ac and H3k56ac are detected by Western blot. As shown in FIG. 44, compound SOL-011 can down regulate H3K9Ac and H3k56ac, so compound SOL-011 can activate SIRT6 deacetylation activity in SW480 cells.

Figure 45:
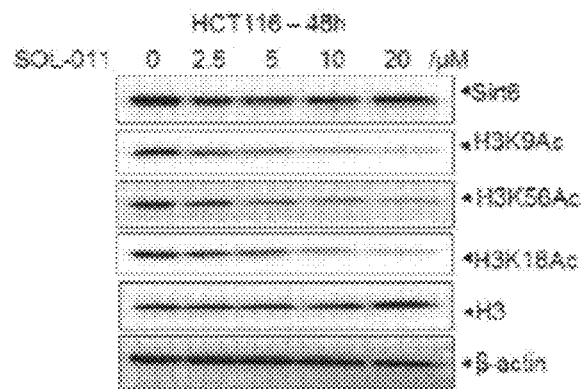
FIG. 45 is a schematic diagram of the SIRT6 deacetylation active substrate H3K9Ac and H3K56Ac in a cell after treatment of CT116 cells with the compound SOL-011 at different concentrations for 48 hours.

After CT116 cells are treated with SOL-011 at different concentrations for 48 hours, the SIRT6 deacetylation active substrates H3K9Ac and H3k56ac are detected by Western blot, as shown in FIG. 45. The results showed that compound SOL-011 down regulated H3K9Ac and h3k56ac, so that compound SOL-011 could significantly deacetylate histone 3 in a concentration dependent manner.

Figure 46:
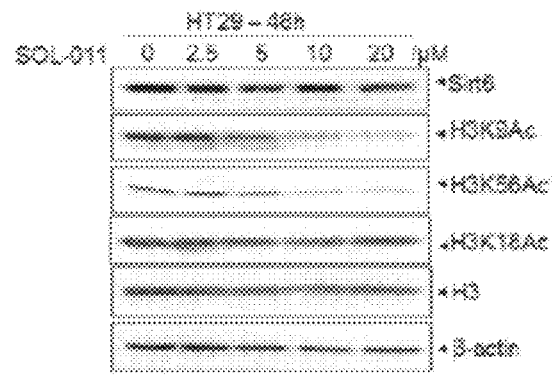
FIG. 46 is a schematic diagram of the SIRT6 deacetylation active substrate H3K9Ac and H3K56Ac in a cell after treatment of HT29 cells with the compound SOL-011 at different concentrations for 48 hours.

After HT29 cells are treated with SOL-011 at different concentrations for 48 hours, the SIRT6 deacetylation active substrates H3K9Ac and H3k56ac are detected by Western blot, as shown in FIG. 46. The results showed that compound SOL-011 down regulated H3K9Ac and H3k56ac, so that compound SOL-011 could significantly deacetylate histone 3 in a concentration dependent manner.

Figure 47:
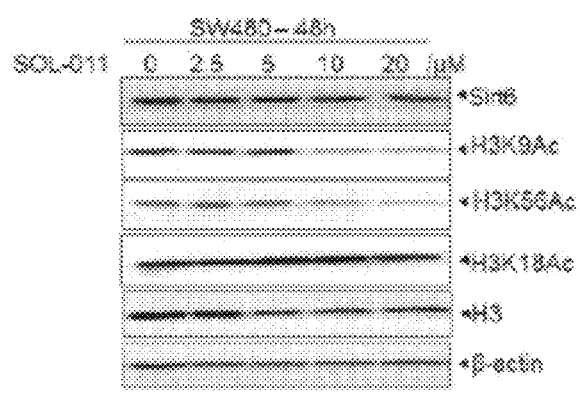
FIG. 47 is a schematic diagram of the SIRT6 deacetylation active substrate H3K9Ac and H3K56Ac in a cell after treatment of SW480 cells with the compound SOL-011 at different concentrations for 48 hours.

After SW480 cells are treated with SOL-011 at different concentrations for 48 hours, the SIRT6 deacetylation active substrates H3K9Ac and H3k56ac are detected by Western blot, as shown in FIG. 47. The results showed that compound SOL-011 down regulated H3K9Ac and H3k56ac, so that compound SOL-011 could significantly deacetylate histone 3 in a concentration dependent manner.

Although a preferred embodiment of the invention has been described for illustrative purposes, it will be understood by those skilled in the art that a variety of modifications, additions or substitutions are feasible without departing from the scope and spirit of the invention as disclosed in the appended claims. The scope of the invention shall be interpreted on the basis of the attached claims in a way that the technical ideas are included in the scope equivalent to the claims belonging to the invention.

What is claimed is:

1. A compound or a pharmacologically acceptable salt thereof, as represented by formula (I):

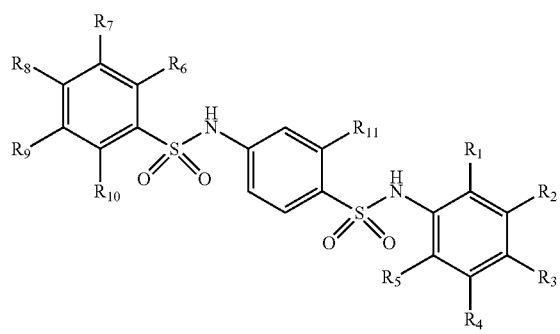

(I)

wherein $R_1$, $R_2$, $R_3$, $R_4$, $R_5$, $R_6$, $R_7$, $R_8$, $R_9$ and $R_{10}$ are independently selected from the group consisting of H, halogen, hydroxyl, nitro, amino, carboxyl, acid ester group, sulfonamide, mercapto, methoxy, ethoxy, benzyloxy, methyl and cyano; $R_1$, $R_2$, $R_3$, $R_4$, $R_5$, $R_6$, $R_7$, $R_9$ and $R_{10}$ is halogen;

$R_{11}$ is

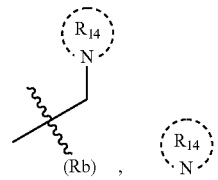

represents substituted or unsubstituted nitrogen-containing heterocyclic ring, and the nitrogen-containing heterocyclic ring is azacyclopropane, azetidine, pyrazole, morpholine, piperidine, piperidine, piperazine, azacycloheptane or azacyclooctane.

2. A compound or a pharmacologically acceptable salt thereof, as represented by formula (I):

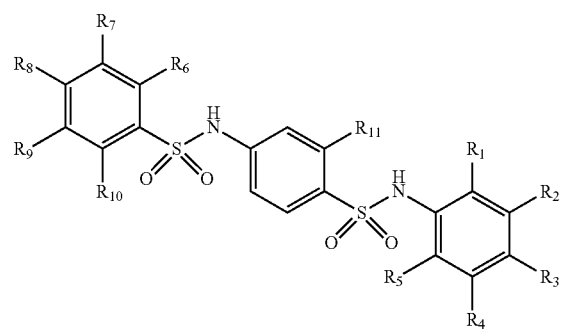

(I)

wherein $R_1$ is methyl;
$R_2$ is H;
$R_3$ is H or halogen;
$R_4$ is H or halogen;
$R_5$ is H or halogen;
$R_6$ is H;
$R_7$ is halogen;
$R_8$ is H;
$R_9$ is halogen;
$R_{10}$ is H; and,
$R_{11}$ is H, Cl, carboxyl, or ester group.

3. The compound as claimed in claim 2, wherein $R_3$ is F;
or, $R_4$ is Br;
or, $R_5$ is Br;
or, $R_7$ is Cl;
or, $R_9$ is Cl;
or, $R_{11}$ is carboxyl, or ester group.

* * * * *